US012576033B2

(12) United States Patent (10) Patent No.: US 12,576,033 B2

Corson et al. (45) Date of Patent: Mar. 17, 2026

(54) SPRAY-DRIED FORMULATION OF A PYRIDAZINONE TRPC5 INHIBITOR

(71) Applicant: GFB (ABC), LLC, Foxboro, MA (US)

(72) Inventors: Donald T. Corson, Erie, CO (US);
Elizabeth Chu Kwong, Lachine (CA);
Thomas E. Stumpfig, Bend, OR (US);
Daniel T. Smithey, Bend, OR (US);
Erica B. Schlesinger, Sisters, OR (US)

(73) Assignee: GFB (ABC), LLC, Foxboro, MA (US)

( * ) Notice: Subject to any disclaimer, the term of this patent is extended or adjusted under 35 U.S.C. 154(b) by 1013 days.

(21) Appl. No.: 17/603,299

(22) PCT Filed: Apr. 10, 2020

(86) PCT No.: PCT/US2020/027673

§ 371 (c)(1),
(2) Date: Oct. 12, 2021

(87) PCT Pub. No.: WO2020/210626

PCT Pub. Date: Oct. 15, 2020

(65) Prior Publication Data

US 2022/0183981 A1 Jun. 16, 2022

Related U.S. Application Data

(60) Provisional application No. 62/991,315, filed on Mar. 18, 2020, provisional application No. 62/832,632, filed on Apr. 11, 2019.

(51) Int. Cl.
*A61K 9/19* (2006.01)
*A61K 9/16* (2006.01)
*A61K 9/20* (2006.01)
*A61K 9/48* (2006.01)

(52) U.S. Cl.
CPC .............. *A61K 9/19* (2013.01); *A61K 9/1652* (2013.01); *A61K 9/1694* (2013.01); *A61K 9/2009* (2013.01); *A61K 9/2013* (2013.01); *A61K 9/2018* (2013.01); *A61K 9/2054* (2013.01); *A61K 9/2095* (2013.01); *A61K 9/4833* (2013.01); *A61K 9/485* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | | |
|---|---|---|---|
| 8,859,547 B2 | 10/2014 | Dorsch et al. | |
| 9,139,573 B2 | 9/2015 | Chong et al. | |
| 10,493,161 B2 | 12/2019 | Warashina et al. | |
| 10,654,850 B2 | 5/2020 | Ledeboer et al. | |
| 11,046,690 B2 | 6/2021 | Ledeboer et al. | |
| 2005/0176722 A1 | 8/2005 | Bono et al. | |
| 2007/0287696 A1 | 12/2007 | Burgey et al. | |
| 2008/0020902 A1 | 1/2008 | Arnold | |
| 2008/0027041 A1 | 1/2008 | Hudkins et al. | |
| 2008/0113966 A1 | 5/2008 | Burgey et al. | |
| 2008/0207902 A1 | 8/2008 | Kohno et al. | |
| 2009/0163545 A1 | 6/2009 | Goldfarb | |
| 2012/0046330 A1 | 2/2012 | Alargova et al. | |
| 2014/0275528 A1 | 9/2014 | Chenard et al. | |
| 2016/0046624 A1 | 2/2016 | Chenard et al. | |
| 2018/0207100 A1* | 7/2018 | Ibrahim ................. A61K 47/12 |
| 2019/0127370 A1 | 5/2019 | KC et al. | |
| 2020/0102301 A1 | 4/2020 | Ledeboer et al. | |
| 2020/0283437 A1 | 9/2020 | Ledeboer et al. | |
| 2022/0024917 A1 | 1/2022 | Ledeboer et al. | |
| 2022/0152031 A1 | 5/2022 | Reilly et al. | |
| 2022/0177455 A1 | 6/2022 | Xue et al. | |
| 2023/0203028 A1 | 6/2023 | Yu et al. | |

FOREIGN PATENT DOCUMENTS

| | | |
|---|---|---|
| CN | 103201277 A | 7/2013 |
| CN | 104718201 A | 6/2015 |
| TW | 200932237 A | 8/2009 |
| WO | WO-2003104225 A1 | 12/2003 |
| WO | 2005115330 A2 | 12/2005 |
| WO | WO-2006044504 A1 | 4/2006 |
| WO | WO-2007106349 A2 | 9/2007 |
| WO | WO-2008115385 A2 | 9/2008 |
| WO | WO-2009006959 A1 | 1/2009 |
| WO | WO-2012177893 A2 | 12/2012 |
| WO | WO-2014058747 A1 | 4/2014 |

(Continued)

OTHER PUBLICATIONS

Meanwell N. Synopsis of Some Recent Tactical Application of Bioisosteres in Drug Design. Mar. 17, 2011. ACS Publications, J. Med. Chem. 2011, 54, 2529-2591. dx.doi.org/10.1021/jm1013693. (Year: 2011).*

Meanwell N. Synopsis of Some Recent Tactical Application of Bioisosteres in Drug Design. Mar. 17, 2011. ACS Publications, J. Med. Chem. 2011, 54, 2529-2591. dx.doi.org/10.1021/jm1013693. (Year: 2011) (Year: 2011).*

Chiang et al., "In Vitro and In Vivo Evaluation of Amorphous Solid Dispersions Generated by Different Bench-Scale Processes, Using Griseofulvin as a Model Compound," AAPS Journal, 15(2):608-617 (2013).

(Continued)

*Primary Examiner* — Ali Soroush
*Assistant Examiner* — Afua Bamfoaa Boateng
(74) *Attorney, Agent, or Firm* — Honigman LLP; Andrew S. Chipouras; Jonathan P. O'Brien

(57) ABSTRACT

Disclosed are spray-dried formulations of 4-chloro-5-(4-(4-fluoro-2-(trifluoromethyl)phenoxy)-5,8-dihydropyrido[3,4-d]pyrimidin-7(6H)-yl)pyridazin-3(2H)-one, methods and compositions for making the same, and solid dosage forms comprising the same. The dosage forms described herein are useful in methods of treating kidney diseases or neuropathies associated with diseases or conditions, and in methods of treating pain, anxiety, or depression.

29 Claims, 55 Drawing Sheets

(56) References Cited

FOREIGN PATENT DOCUMENTS

| WO | 2016022942 A1 | 2/2016 |
|---|---|---|
| WO | WO-2017197051 A1 | 11/2017 |
| WO | WO-2019055966 A2 | 3/2019 |
| WO | WO-2020061162 A1 | 3/2020 |
| WO | WO-2020191056 A1 | 9/2020 |
| WO | WO-2020206623 A1 | 10/2020 |
| WO | WO-2020210626 A1 | 10/2020 |
| WO | WO-2020210639 A1 | 10/2020 |
| WO | WO-2022001767 A1 | 1/2022 |

OTHER PUBLICATIONS

International Preliminary Report on Patentability for International Application No. PCT/US2020/02763 mailed Oct. 21, 2021.
International Search Report and Written Opinion for International Application No. PCT/US20/27673 mailed Jul. 1, 2020.
Alawi et al., "Transient receptor potential canonical 5 channels plays an essential role in hepatic dyslipidemia associated with cholestasis," Scientific Reports, 7: 2338, (9 pages)(2017).
Barbaro et al., "Synthesis, Biological Evaluation, and Pharmacophore Generation of New Pyridazinone Derivatives with Affinity toward a1- and a2-Adrenoceptorst," J. Med. Chem., 44(13): 2118-2132 (2001).
Betti et al., "al-Adrenoceptor Antagonists. 6.1 Structural Optimization of Pyridazinone-Arylpiperazines. Study of the Influence on Affinity and Selectivity of Cyclic Substituents at the Pyridazinone Ring and Alkoxy Groups at the Arylpiperazine Moiety," J. Med. Chem., 46: 35553558 (2003).
CAS Registry No. 1030737-98-4; STN Entry date Jun. 26, 2008.
CAS Registry No. 1147349-21-0; STN Entry Date May 19, 2009.
CAS Registry No. 1354526-97-8; STN Entry Date Jan. 26, 2012.
CAS Registry No. 1427907-65-0; STN Entry Date Apr. 11, 2013.
CAS Registry No. 1593374-28-7; STN Entry Date Apr. 30, 2014.
CAS Registry No. 1602976-93-1; STN Entry Date May 12, 2014.
CAS Registry No. 1866845-79-5; STN Entry Date Feb. 15, 2016.
CAS Registry No. 2092061-72-6; STN Entry Date Apr. 19, 2017.
CAS Registry No. 932140-24-4; STN Entry Date Apr. 24, 2007.
CAS Registry No. 940271-83-0; STN Entry Date Jun. 29, 2007.
CAS Registry No. 940805-31-2; STN Entry Date Jul. 2, 2007.
Castle et al., "Pyridazines. II I. The synthesis of substituted pyridazines," Journal of Heterocyclic Chemistry, 2:463-472 (1965).
Chiang, P. C. et al., In Vitro and In Vivo Evaluation of Amorphous Solid Dispersions Generated by Different Bench-Scale Processes, Using Griseofulvin as a Model Compound. The AAPS Journal 15(2), Mar. 2, 2013; p. 608, second paragraph; p. 609, fifth paragraph.
Corsano et al., "New pyridazinones: synthesis and correlation between structure and a-blocking activity," Eur J Med Chem, 28: 647-651 (1993).
Corsano et al., "Synthesis And Bronchospasmolytic Properties of Some Pyridazinone Derivatives," Bioorganic & Medicinal Chemistry Letters, 3(12): 2713-2716 (1993).
Corsano et al., "Synthesis and pharmacological activity of some new pyridazinones," Eur J Med Chem, 27: 545-549 (1992).
Extended European Search Report for EP Application No. 18857094 dated May 3, 2021.
Extended European Search Report for EP Application No. 19863481.8 dated May 17, 2022.
Friesen, D. T. et al., "Hydroxypropyl Methylcellulose Acetate Succinate-Based Spray-Dried Dispersions: An Overview," Mol. Pharmaceutics, vol. 5, No. 6, pp. 1003-1019 (2008).
Gaunt et al., "Transient receptor potential canonical 4 and 5 proteins as targets in cancer therapeutics," Eur Biophys J, 45: 611-620 (2016).
International Preliminary Report on Patentability for International Application No. PCT/US2018/051465 mailed Apr. 2, 2020.
International Preliminary Report on Patentability for International Application No. PCT/US2020/023369 issued Sep. 16, 2021.

International Preliminary Report on Patentability for International Application No. PCT/US2020/027689 issued Sep. 28, 2021.
International Search Report and Written Opinion for International Application No. PCT/CN2019/081985 mailed Jan. 15, 2020.
International Search Report and Written Opinion for International Application No. PCT/US2018/51465 mailed Feb. 27, 2019.
International Search Report and Written Opinion for International Application No. PCT/US2019/51680 dated Jan. 9, 2020.
International Search Report and Written Opinion for International Application No. PCT/US2020/023369 mailed Aug. 20, 2020.
International Search Report and Written Opinion for International Application No. PCT/US2020/027689 mailed Jun. 15, 2020.
International Search Report and Written Opinion for International Application No. PCT/US2020/27673, mailed Jul. 1, 2020.
Just et al., "Treatment with HC-070, a potent inhibitor of TRPC4 and TRPC5, leads to anxiolytic and antidepressant effects in mice," Plos One, 13(1): e0191225 (32 pages)(2018).
Ma et al., "Transient receptor potential channel TRPC5 is essential for P-glycoprotein induction in drug-resistant cancer cells," PNAS, 109(40): 16282-16287 (2012).
Miller et al., "Identification of ML204, a Novel Potent Antagonist That Selectively Modulates Native TRPC4/C5 Ion Channels," Journal of Biological Chemistry, 286(38):33436-33446 (2011).
Minard et al, "Remarkable Progress with Small-Molecule Modulation of TRPC1/4/5 Channels: Implications for Understanding the Channels in Health and Disease," Cells, 7(52):1-20 (2018).
Pablo et al., "Charting a TRP to Novel Therapeutic Destinations for Kidney Diseases," Trends in Pharmacological Sciences, 40(12):911-918 (2019).
Paudel, A., et al., "Manufacturing of solid dispersions of poorly water soluble drugs by spray drying: Formulation and process considerations," Int. J. Pharmaceut. (2012), <http://dx.doi.org/10.1016/j.ijpharm.2012.07.015>.
PubChem-CID-91009634, Create Date: Mar. 17, 2015 (Mar. 17, 2015), p. 2, Fig.
Pubmed Compound Summary for CID 45834084, "4-Chloro-4[4-(4-methoxyphenoxy)piperidin-1-yl]-2,3-dihydropyridazin-3-one," https://pubchem.ncbi.nlm.nih.gov/compound/45834084, (2015).
Pubmed Compound Summary for CID 75420213, "4-Chloro-2-phenyl-5-{5H,6H,7H,8H-pyrido[3,4-d]pyrimidi n-7-yl}-2,3-dihydropropyridazin-3-one," https://pubchem.ncbi.nlm.nih.gov/compound/75420213 (2014).
Pubmed Compound Summary for CID 86805598, "NRUODMAEBORIK-UHFFFAOYSA-N," https://pubchem.ncbi.nlm.nih.gov/compound/86805598, (2015).
Pubmed Compound Summary for CID 86942850, "YDHFXQRLHBDRHD-UHFFFAOYSA-N," https://pubchem.ncbi.nlm.nih.gov/compound/86942850 (2015).
Sachdeva et al., "TRPC proteins contribute to development of diabetic retinopathy and regulate glyoxalase 1 activity and methylglyoxal accumulation," Molecular Metabolism, 9, 156167 (2018).
Schaldecker et al., "Inhibition of the TRPC5 ion channel protects the kidney filter," J Clin Invest., 123(12):5298-5309 (2013).
Strappaghetti et al., "Adenosine receptors: synthesis, structure-activity relationships and biological activity of new 6-amino purine derivatives" European Journal of Medicinal Chemistry, Jun. 1998, vol. 33, pp. 501-508, p. 504, Figure 3.
Toure, B. B. et al., "The Role of the Acidity of N-Heteroaryl Sulfonamides as Inhibitors of Bcl-2 Family Protein-Protein Interactions," ACS Med. Chem. Lett., 2013, vol. 4, No. 2, pp. 186190.
Wei et al., "Regulation of neuropathic pain behavior by amygdaloid TRPC4/C5 channels," Neuroscience Letters, 608: 12-17 (2015).
Wei et al., "Therapeutic Effects of FK506 on IgA Nephropathy Rat," Kidney & Blood Pressure Research, 42: 983-998 (2017).
Westlund et al., "A Rat Knockout Model Implicates TRPC4 In Visceral Pain Sensation," Neuroscience, 262: 165-175 (2014).
Yu et al., "Discovery of a Potent and Selective TRPC5 Inhibitor, Efficacious in a Focal Segmental Glomerulosclerosis Model," ACS Med Chem Lett, 10:1579-1585 (2019).
Zhou et al., "A small-molecule inhibitor of TRPC5 ion channels suppresses progressive kidney disease in animal models," Science, 358:1332-1336 (2017).

(56) References Cited

OTHER PUBLICATIONS

Zhou et al., "Human relevance of blocking the Rac1-TRPC5 pathway as a podocyte-protective strategy for progressive kidney diseases," *bioRxiv*: 41 pages (2020).

Wang Ruyi et al. "Application of Hydroxypropyl Methyl cellulose Acetate Succinate in the Preparation of Solid Dispersions," 2016, pp. 111-116, vol. 47, No. 1.

Wei Chao and Hou Feiyan, Pharmacology, Henan Science and Technology Press, 2012.

\* cited by examiner

Figure 3
500X
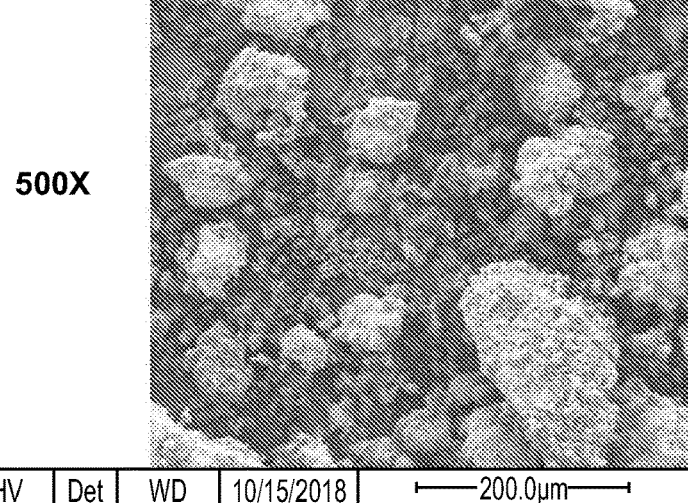
| Mag 500x | Spot 3.0 | HV 10.0kV | Det ETD | WD 10.0mm | 10/15/2018 9:05:11AM | ⊢——200.0µm——⊣ GFB-887, Lot# A05313-058P1 |
1,500X
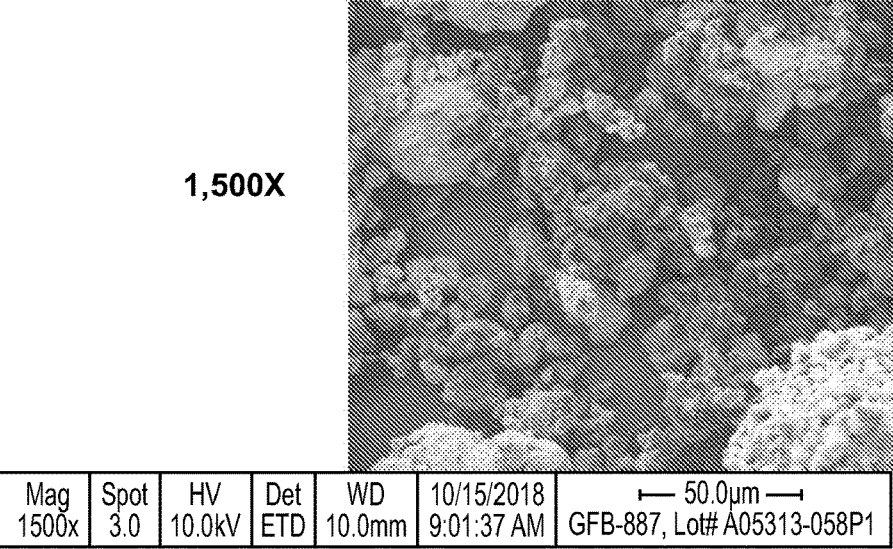
| Mag 1500x | Spot 3.0 | HV 10.0kV | Det ETD | WD 10.0mm | 10/15/2018 9:01:37 AM | ⊢— 50.0µm —⊣ GFB-887, Lot# A05313-058P1 |
5,000X
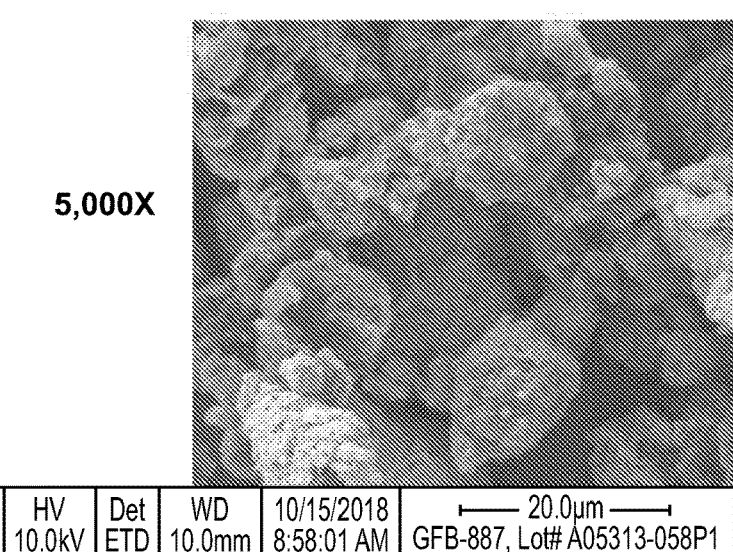
| Mag 5000x | Spot 3.0 | HV 10.0kV | Det ETD | WD 10.0mm | 10/15/2018 8:58:01 AM | ⊢— 20.0µm —⊣ GFB-887, Lot# A05313-058P1 |

Figure 13

ThermoFisher
SCIENTIFIC

CERTIFICATE OF TESTING

Material Description:　25:75 GFB-887:HPMCAS-M SDI
Patheon Lot #:　　　　D-18-078
Date of Manufacture:　12Dec2018
Expiration/Review Date: NA
Storage:　　　　　　　room Temperature
Certificate Rev #:　　1
Page:　　　　　　　　1 of 6

Note: Contains a new drug for investigational use only in laboratory research animals, or for *in vitro* tests. Not for use in humans.

| Test | Procedure/LNB Ref. | Reporting Requirements | Result | | |
|---|---|---|---|---|---|
| Appearance | AM-0002/ G8-852-40 | Report Results | Off-white, tannish powder | | |
| Identification (HPLC, Retention Time Comparsion) | DM-0240 (Draft)/ G8-852-13 | %Agreement Compared to Reference Standard | 100% | | |
| Assay (HPLC) | DM-0240 (Draft)/ G8-852-13 | Report Results (wt%) | 24.5% | | |
| Individual Impurities and Related Substances (HPLC) | DM-0240 (Draft)/ G8-852-13 | Report Results (% peak area) | RRT | %Peak Area | |
| | | | 0.34 | 0.20 | |
| | | | 0.36 | 0.09 | |
| | | | 0.37 | <0.05 | |
| | | | 0.38 | <0.05 | |
| | | | 0.56 | <0.05 | |
| | | | 0.65 | <0.05 | |
| | | | 0.68 | <0.05 | |
| | | | 0.72 | 0.09 | |
| | | | 0.80 | 0.05 | |
| | | | 0.85 | 0.39 | |
| | | | 0.91 | <0.05 | |
| | | | 1.02 | 0.08 | |
| | | | 1.05 | 0.05 | |
| | | | 1.10 | <0.05 | |
| | | | 1.13 | <0.05 | |
| | | | 1.44 | <0.05 | |
| | | | 1.47 | 0.06 | |
| | | | 1.50 | <0.05 | |
| | | | 1.58 | <0.05 | |

Figure 13 (cont.)

ThermoFisher
S C I E N T I F I C

CERTIFICATE OF TESTING

Material Description:     25:75 GFB-887:HPMCAS-M SDI
Patheon Lot #:            D-18-078
Date of Manufacture:      12Dec2018
Expiration/Review Date:   NA
Storage:                  Room Temperature
Certificate Rev #:        1
Page:                     2 of 6

Note: Contains a new drug for investigational use only in laboratory research animals, or for *in vitro* tests. Not for use in humans.

| Test | Procedure/LNB Ref. | Reporting Requirements | Result |
|---|---|---|---|
| Total impurities (HPLC) | DM-0240 (Draft)/ G8-852-13 | Report Results,≥0.05% (%area) | 1.01% |
| Water Content (KF) | AM-0233 (Draft) USP<921>/ G8-852-42 | Report Result (wt%) | 0.20% |
| Residual Solvent (GC) a. Dichloromethane b. Methanol | AM-0021/ G8-852-49 | a. NMT 660 PPM b. NMT 3000 PPM | a. Not Detected b. Not Detected |
| Thermal analysis (MDSC) | DM-0046 USP<891>/ G8-852-39 | Report Results | Tg=93°C±2°C (See Figure 1) |
| Crystallinity (XRPD) | DM-0044 USP<941>/ G8-852-38 | Report Results | Small diffraction peak observed at 26°2θ (See Figure 2) |
| Particle size Distribution by Laser Light Diffraction | DM-0166 USP<429>(n=4)/ G8-852-50 | Report the average results for Dv10,Dv50, Dv90 in µm | d10- 6.3 µm d50- 23.9 µm d90- 69.5 µm |
| Particle Morphology (SEM) | USP<1181>/ G8-852-48 | Report Results | See Figure 3 |

Figure 13 (cont.)

ThermoFisher
S C I E N T I F I C

CERTIFICATE OF TESTING

Material Description:      25:75 GFB-887:HPMCAS-M SDI
Patheon Lot #:            D-18-078
Date of Manufacture:      12Dec2018
Expiration/Review Date:   NA
Storage:                  Room Temperature
Certificate Rev #:        1
Page:                     3 of 6

Note: Contains a new drug for investigational use only in laboratory research animals, or for *in vitro* tests. Not for use in humans.

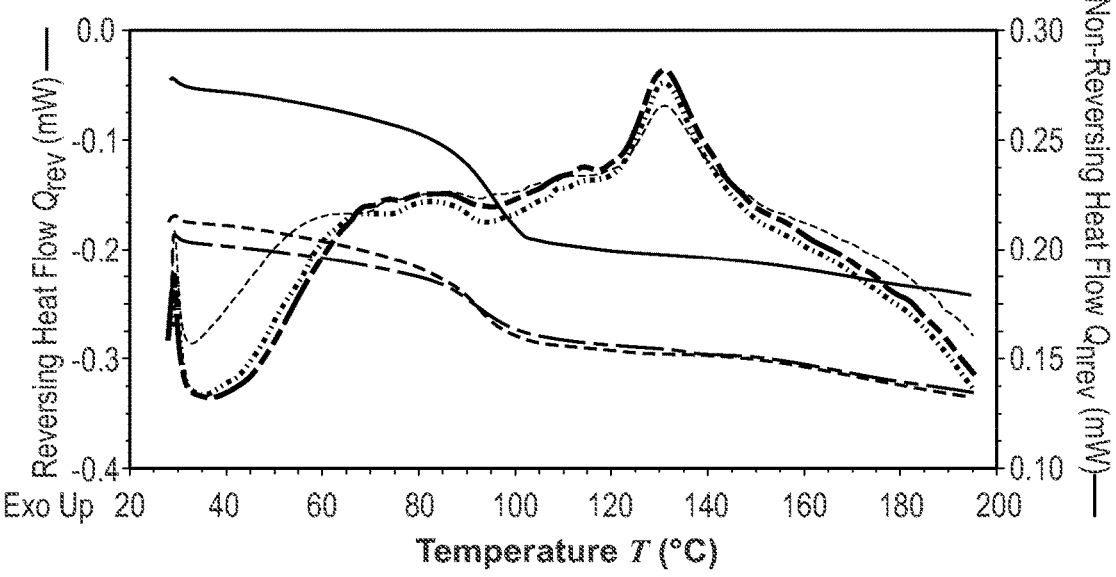

*Figure 1. MDSC of 25:75 GFB-887:HPMCAS-M SDI (Lot: D-18-078)*

Figure 13 (cont.)

ThermoFisher
S C I E N T I F I C

CERTIFICATE OF TESTING

Material Description:    25:75 GFB-887:HPMCAS-M SDI
Patheon Lot #:    D-18-078
Date of Manufacture:    12Dec2018
Expiration/Review Date:   NA
Storage:    room Temperature
Certificate Rev #:    1
Page:    4 of 6

Note: Contains a new drug for investigational use only in laboratory research animals, or for *in vitro* tests. Not for use in humans.

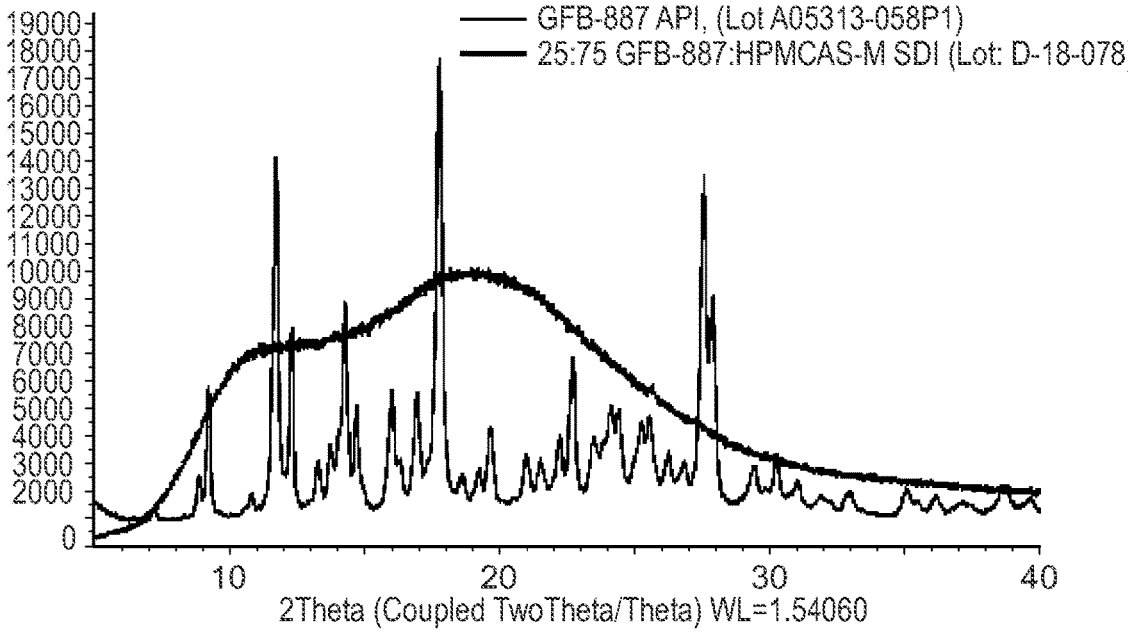

*Figure 2. XRPD of 25:75 GFB-887:HPMCAS-M SDI (Lot: D-18-078)*

Figure 13 (cont.)

ThermoFisher
S C I E N T I F I C

CERTIFICATE OF TESTING

Material Description:    25:75 GFB-887:HPMCAS-M SDI
Patheon Lot #:    D-18-078
Date of Manufacture:    12Dec2018
Expiration/Review Date:  NA
Storage:    room Temperature
Certificate Rev #:    1
Page:    5 of 6

Note: Contains a new drug for investigational use only in laboratory research animals, or for in vitro tests. Not for use in humans.

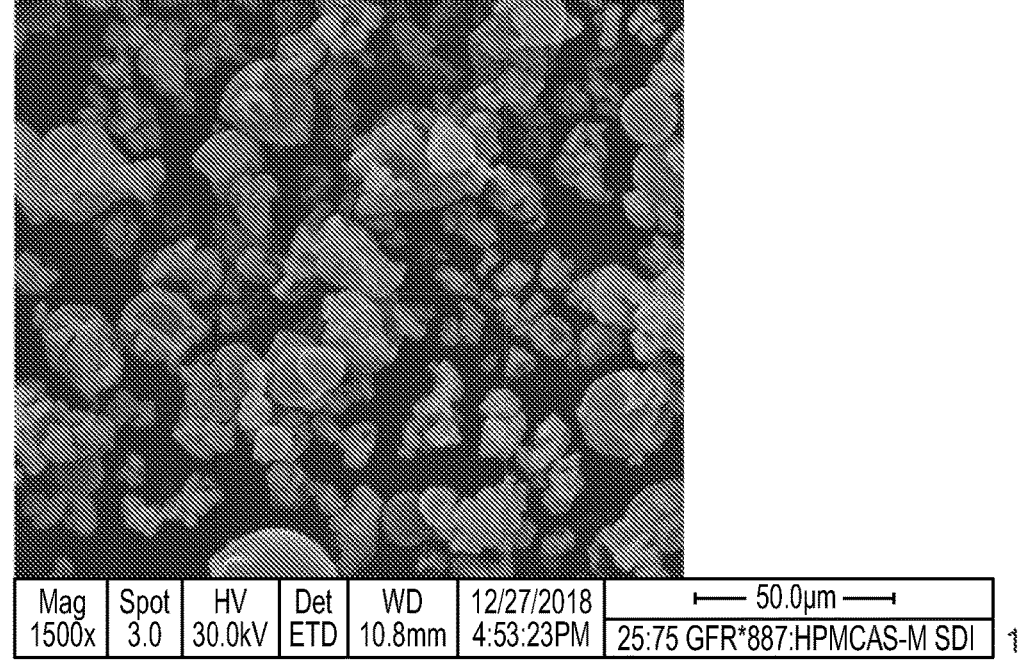

| Mag | Spot | HV | Det | WD | 12/27/2018 | ⊢── 50.0µm ──⊣ | |
|------|------|--------|-----|--------|-----------|--------------------------------|---|
| 1500x | 3.0 | 30.0kV | ETD | 10.8mm | 4:53:23PM | 25:75 GFR*887:HPMCAS-M SDI | 1 |

*Figure 3. SEM of 25:75 GFB-887: HPMCAS-M SDI (Lot: D-18-078)*

Figure 13 (cont.)

ThermoFisher
S C I E N T I F I C

CERTIFICATE OF TESTING

Material Description:    25:75 GFB-887:HPMCAS-M SDI
Patheon Lot #:           D-18-078
Date of Manufacture:     12Dec2018
Expiration/Review Date:  NA
Storage:                 Room Temperature
Certificate Rev #:       1
Page:                    6 of 6

Note: Contains a new drug for investigational use only in laboratory research animals, or for *in vitro* tests. Not for use in humans.

Revision History:

| Revision # | Change | Date |
|---|---|---|
| 00 | New document | 10Jan2019 |
| 01 | Update SEM Figure Title | 09May2019 |

Prepared By/Date:

Ashley Moon
I am the author of this document
2019.05.09 13:31:24-07'00'

Reviewed By/Date:

James, Jamie L
I am approving this document
2019.05.09 14:53:50-07'00'

Figure 14A

| Sample Description | Timepoint | SSID | RRT | 0.35 | 0.37 | 0.38 | 0.39 | 0.56 | 0.65 | 0.68 | 0.80 | 0.85 | 0.91 | 1.00 |
|---|---|---|---|---|---|---|---|---|---|---|---|---|---|---|
| GFB-887 API (Lot: TJ-GDF-9815-0-A-1) | t=0 | 5593 | %Peak Area | 0.19 | 0.06 | 0.03 | 0.02 | 0.04 | 0.02 | 0.05 | 0.07 | 0.42 | 0.04 | 98.83 |
| | | | Reported % Peak Area | 0.19 | 0.06 | <0.05 | <0.05 | <0.05 | <0.05 | 0.05 | 0.07 | 0.42 | <0.05 | N/A |

| Sample Description | Timepoint | SSID | RRT | 1.02 | 1.06 | 1.10 | 1.42 | 1.46 | Total Impurities |
|---|---|---|---|---|---|---|---|---|---|
| GFB-887 API (Lot: TJ-GDF-9815-0-A-1) | t=0 | 5593 | %Peak Area | 0.05 | 0.03 | 0.4 | 0.02 | 0.07 | |
| | | | Reported % Peak Area | 0.05 | <0.05 | <0.05 | <0.05 | 0.07 | 0.91% |

Figure 14B

| Sample Description | Timepoint | SSID | RRT | 0.35 | 0.37 | 0.38 | 0.40 | 0.56 | 0.65 | 0.68 | 0.80 | 0.85 | 0.91 | 1.00 |
|---|---|---|---|---|---|---|---|---|---|---|---|---|---|---|
| 7wt% Solids 25:75 Compund 1 HPMCAS-M in 6:4 DCM:MeOH Spray sol Lot: G8-936-10 | t=1day @40°C | 5593 | %Peak Area | 0.18 | 0.06 | 0.03 | 0.02 | 0.02 | 0.03 | 0.03 | 0.08 | 0.43 | 0.05 | 98.85 |
| | | | Report % Peak Area | 0.18 | 0.06 | <0.05 | <0.05 | <0.05 | <0.05 | <0.05 | 0.08 | 0.43 | 0.05 | N/A |
| | | | Absolute Change in Impurity (%) | 0.01 | 0.00 | 0.00 | 0.00 | 0.01 | 0.02 | 0.02 | 0.01 | 0.02 | 0.02 | N/A |
| | | | % Peak Area | 0.17 | 0.06 | 0.02 | 0.02 | 0.03 | 0.04 | 0.03 | 0.08 | 0.40 | 0.06 | 98.87 |
| | | | Reported % Peak Area | 0.17 | 0.06 | <0.05 | <0.05 | <0.05 | <0.05 | <0.05 | 0.08 | 0.43 | 0.05 | N/A |
| | | | Absolute Change in Impurity (%) | 0.02 | 0.00 | 0.01 | 0.00 | 0.01 | 0.02 | 0.02 | 0.01 | 0.02 | 0.2 | N/A |

| Sample Description | Timepoint | SSID | RRT | 1.02 | 1.06 | 1.10 | 1.42 | 1.46 | Total Impurities |
|---|---|---|---|---|---|---|---|---|---|
| 7wt% Solids 25:75 Compund 1 HPMCAS-M in 6:4 DCM:MeOH Spray sol Lot: G8-936-10 | t=1day @40°C | 5593 | %Peak Area | 0.05 | 0.02 | 0.05 | 0.02 | 0.0 | |
| | | | Report % Peak Area | 0.05 | <0.05 | 0.05 | <0.05 | 0.07 | |
| | | | Absolute Change in Impurity (%) | 0.00 | 0.01 | 0.01 | 0.00 | 0.00 | 0.97% |
| | | | % Peak Area | 0.05 | 0.02 | 0.05 | 0.02 | 0.07 | |
| | | | Reported % Peak Area | 0.05 | <0.05 | 0.05 | <0.05 | 0.07 | |
| | | | Absolute Change in Impurity (%) | 0.00 | 0.01 | 0.01 | 0.00 | 0.00 | 0.94% |

Figure 14C

| Sample Description | Timepoint | SSID | RRT | 0.35 | 0.37 | 0.38 | 0.40 | 0.56 | 0.65 | 0.68 | 0.80 | 0.85 | 0.91 | 0.96 |
|---|---|---|---|---|---|---|---|---|---|---|---|---|---|---|
| 7wt% Solids 25:75 Compund 1 HPCAS-M in 6:4 DCM:MeOH Spray sol Lot. G8-936-10 | t=3day @40°C | 6599 | %Peak Area | 0.16 | 0.07 | 0.02 | 0.03 | 0.03 | 0.03 | 0.03 | 0.07 | 0.41 | 0.07 | |
| | | | Report % Peak Area | 0.16 | 0.07 | <0.05 | <0.05 | <0.05 | <0.05 | <0.05 | 0.07 | 0.41 | 0.07 | <0.05 |
| | | | Absolute Change in Impurity (%) | 0.03 | 0.01 | 0.01 | 0.01 | 0.01 | 0.01 | 0.02 | 0.00 | 0.01 | 0.03 | 0.00 |
| | | | % Peak Area | 0.17 | 0.07 | 0.02 | 0.04 | 0.03 | 0.03 | 0.03 | 0.07 | 0.42 | 0.07 | 0.02 |
| | | | Reported % Peak Area | 0.17 | 0.07 | <0.05 | <0.05 | <0.05 | <0.05 | <0.05 | 0.07 | 0.42 | 0.07 | <0.05 |
| | | | Absolute Change in Impurity (%) | 0.02 | 0.01 | 0.01 | 0.02 | 0.01 | 0.01 | 0.02 | 0.00 | 0.00 | 0.03 | 0.02 |

| Sample Description | Timepoint | SSID | RRT | 1.00 | 1.02 | 1.06 | 1.10 | 1.42 | 1.46 | 1.48 | Total Impurities |
|---|---|---|---|---|---|---|---|---|---|---|---|
| 7wt% Solids 25:75 Compund 1 HPCAS-M in 6:4 DCM:MeOH Spray sol Lot. G8-936-10 | t=3day @40°C | 6599 | %Peak Area | 98.84 | 0.04 | 0.03 | 0.05 | 0.02 | 0.07 | 0.03 | |
| | | | Report % Peak Area | N/A | <0.05 | <0.05 | 0.05 | <0.05 | 0.07 | <0.05 | |
| | | | Absolute Change in Impurity (%) | N/A | 0.01 | 0.00 | 0.01 | 0.00 | 0.00 | 0.03 | 0.90% |
| | | | % Peak Area | 98.87 | 0.04 | 0.02 | 0.02 | 0.02 | 0.08 | | |
| | | | Reported % Peak Area | N/A | <0.05 | <0.05 | <0.05 | <0.05 | 0.08 | | |
| | | | Absolute Change in Impurity (%) | N/A | 0.01 | 0.01 | 0.02 | 0.00 | 0.01 | | 0.88% |

Figure 14D

| Sample Description | Timepoint | SSID | RRT | 0.35 | 0.37 | 0.38 | 0.40 | 0.56 | 0.65 | 0.68 | 0.80 | 0.85 | 0.89 | 0.92 |
|---|---|---|---|---|---|---|---|---|---|---|---|---|---|---|
| 7wt% Solids 25:75 Compund 1 HPMCAS-M in 6:4 DCM:MeOH Spray sol Lot: G8-936-10 | t=6day @40°C | 7188 | Peak Area | 0.17 | 0.06 | 0.02 | 0.02 | 0.03 | 0.02 | 0.02 | 0.04 | 0.38 | 0.03 | 0.14 |
| | | | Report Peak Area | 0.17 | 0.06 | <0.05 | <0.05 | <0.05 | <0.05 | <0.05 | <0.05 | 0.38 | <0.05 | 0.14 |
| | | | Absolute Change in Impurity () | 0.02 | 0.00 | 0.01 | 0.00 | 0.01 | 0.00 | 0.03 | 0.03 | 0.04 | 0.03 | 0.10 |
| | | | Peak Area | 0.17 | 0.06 | 0.03 | 0.02 | 0.03 | 0.03 | 0.03 | 0.05 | 0.38 | 0.02 | 0.15 |
| | | | Reported Peak Area | 0.17 | 0.06 | <0.05 | <0.05 | <0.05 | <0.05 | <0.05 | 0.05 | 0.38 | <0.05 | 0.15 |
| | | | Absolute Change in Impurity () | 0.02 | 0.00 | 0.00 | 0.00 | 0.00 | 0.01 | 0.00 | 0.02 | 0.04 | 0.02 | 0.11 |

| Sample Description | Timepoint | SSID | RRT | 0.96 | 1.00 | 1.02 | 1.05 | 1.10 | 1.43 | 1.46 | 1.48 | 1.49 | 1.51 | 1.56 |
|---|---|---|---|---|---|---|---|---|---|---|---|---|---|---|
| 7wt% Solids 25:75 Compund 1 HPMCAS-M in 6:4 DCM:MeOH Spray sol Lot: G8-936-10 | t=6day @40°C | 7188 | %Peak Area | 0.05 | 98.61 | 0.04 | 0.03 | 0.05 | 0.02 | 0.06 | 0.03 | 0.03 | 0.05 | 0.03 |
| | | | Report % Peak Area | 0.05 | N/A | <0.05 | <0.05 | 0.05 | <0.05 | 0.06 | <0.05 | <0.05 | 0.05 | <0.05 |
| | | | Absolute Change in Impurity (%) | 0.05 | N/A | 0.01 | 0.00 | 0.01 | 0.00 | 0.01 | 0.03 | 0.03 | 0.05 | 0.03 |
| | | | % Peak Area | 0.05 | 98.62 | 0.04 | | 0.05 | 0.02 | 0.07 | 0.03 | 0.05 | 0.05 | 0.04 |
| | | | Reported % Peak Area | 0.05 | N/A | <0.05 | <0.05 | 0.05 | <0.05 | 0.07 | | | 0.05 | |
| | | | Absolute Change in Impurity (%) | 0.05 | N/A | 0.01 | 0.03 | 0.01 | 0.00 | 0.00 | | 0.05 | 0.05 | 0.04 |

Figure 14D (cont.)

| Sample Description | Timepoint | SSID | RRT | | 1.78 | Total Impurities |
|---|---|---|---|---|---|---|
| 7wt% Solids 25:75 Compund 1 HPMCAS-M in 6:4 DCM:MeOH Spray sol Lot: G8-936-10 | t=6day @40°C | 7188 | %Peak Area | | 0.05 | |
| | | | Report % Peak Area | | 0.05 | |
| | | | Absolute Change in Impurity (%) | | 0.05 | 1.01% |
| | | | % Peak Area | | 0.09 | |
| | | | Reported % Peak Area | | 0.09 | |
| | | | Absolute Change in Impurity (%) | | 0.09 | 1.12% |

Figure 14E

Sample Description: 7wt% Solids 25:75 Compound 1 HPMCAS-M in 6:4 DCM:MeOH Spray sol Lot: G8-936-10
Timepoint: t=7day @40°C
SSID: 8039

| RRT | 0.35 | 0.37 | | 0.39 | 0.56 | 0.65 | 0.68 | 0.80 | 0.85 | 0.89 | 0.92 |
|---|---|---|---|---|---|---|---|---|---|---|---|
| %Peak Area | 0.17 | 0.06 | | 0.03 | 0.06 | 0.02 | 0.04 | 0.07 | 0.38 | 0.05 | 0.17 |
| Report % Peak Area | 0.17 | 0.06 | ND | <0.05 | 0.06 | <0.05 | <0.05 | 0.07 | 0.38 | 0.05 | 0.17 |
| Absolute Change in Impurity (%) | 0.02 | 0.00 | 0.03 | 0.01 | 0.02 | 0.00 | 0.01 | 0.00 | 0.04 | 0.05 | 0.13 |
| % Peak Area | 0.17 | 0.06 | | 0.02 | 0.03 | 0.04 | 0.02 | 0.05 | 0.39 | 0.03 | 0.17 |
| Reported % Peak Area | 0.17 | 0.06 | ND | <0.05 | <0.05 | <0.05 | <0.05 | 0.05 | 0.39 | <0.05 | 0.17 |
| Absolute Change in Impurity (%) | 0.02 | 0.00 | 0.03 | 0.00 | 0.01 | 0.02 | 0.01 | 0.02 | 0.03 | 0.03 | 0.13 |

Sample Description: 7wt% Solids 25:75 Compound 1 HPMCAS-M in 6:4 DCM:MeOH Spray sol Lot: G8-936-10
Timepoint: t=7day @40°C
SSID: 8039

| RRT | 0.96 | 1.00 | 1.02 | 1.05 | 1.10 | 1.43 | 1.46 | 1.51 | 1.57 | Total Impurities |
|---|---|---|---|---|---|---|---|---|---|---|
| %Peak Area | 0.06 | 98.56 | 0.04 | 0.02 | 0.05 | 0.04 | 0.08 | 0.07 | 0.04 | |
| Report % Peak Area | 0.06 | N/A | <0.05 | <0.05 | 0.05 | <0.05 | 0.08 | 0.07 | <0.05 | |
| Absolute Change in Impurity (%) | 0.06 | N/A | 0.01 | 0.01 | 0.01 | 0.02 | 0.01 | 0.07 | 0.04 | 1.22% |
| % Peak Area | 0.06 | 98.55 | 0.04 | 0.02 | 0.06 | 0.04 | 0.08 | 0.08 | 0.08 | |
| Reported % Peak Area | 0.06 | N/A | <0.05 | <0.05 | 0.06 | <0.05 | 0.08 | 0.08 | 0.08 | |
| Absolute Change in Impurity (%) | 0.06 | N/A | 0.01 | 0.01 | 0.02 | 0.02 | 0.01 | 0.08 | 0.08 | 1.20% |

Figure 14F

Sample Description: 7wt% Solids 25:75 Compund 1 HPMCAS-M in 6:4 DCM:MeOH Spray sol Lot: G8-936-10  Timepoint: t=9day @40°C  SSID: 8972

| RRT | 0.35 | 0.37 | 0.39 | 0.45 | 0.56 | 0.66 | 0.68 | 0.80 | 0.85 | 0.89 |
|---|---|---|---|---|---|---|---|---|---|---|
| %Peak Area | 0.17 | 0.06 | 0.05 | 0.03 | 0.03 | 0.03 | 0.02 | 0.06 | 0.41 | 0.89 |
| Report % Peak Area | 0.17 | 0.06 | 0.05 | <0.05 | <0.05 | <0.05 | <0.05 | 0.06 | 0.41 | <0.05 |
| Absolute Change in impurity (%) | 0.02 | 0.00 | ND | 0.03 | 0.01 | 0.01 | 0.03 | 0.01 | 0.01 | 0.02 |
| % Peak Area | 0.17 | 0.06 | 0.02 | | 0.03 | 0.02 | 0.03 | 0.05 | 0.41 | 0.02 |
| Reported % Peak Area | 0.17 | 0.06 | <0.05 | | <0.05 | 0.05 | <0.05 | 0.05 | 0.41 | <0.05 |
| Absolute Change in impurity (%) | 0.02 | 0.00 | ND | | 0.01 | 0.00 | 0.02 | 0.02 | 0.01 | 0.02 |

Sample Description: 7wt% Solids 25:75 Compund 1 HPMCAS-M in 6:4 DCM:MeOH Spray sol Lot: G8-936-10  Timepoint: t=9day @40°C  SSID: 8972

| RRT | 0.92 | 0.96 | 1.00 | 1.02 | 1.05 | 1.10 | 1.43 | 1.46 | 1.48 | 1.51 | 1.57 | Total Impurities |
|---|---|---|---|---|---|---|---|---|---|---|---|---|
| %Peak Area | 0.12 | 0.06 | 98.63 | 0.04 | 0.02 | 0.05 | 0.03 | 0.07 | 0.02 | 0.03 | 0.05 | |
| Report % Peak Area | 0.12 | 0.06 | N/A | <0.05 | <0.05 | 0.05 | <0.05 | 0.07 | <0.05 | <0.05 | 0.05 | 1.10% |
| Absolute Change in impurity (%) | 0.08 | 0.06 | N/A | 0.01 | 0.01 | 0.01 | 0.01 | 0.00 | 0.02 | 0.03 | 0.05 | |
| % Peak Area | 0.11 | 0.06 | 98.66 | 0.04 | 0.02 | 0.04 | 0.04 | 0.06 | 0.02 | 0.05 | 0.09 | |
| Reported % Peak Area | 0.11 | 0.06 | N/A | <0.05 | <0.05 | <0.05 | <0.05 | 0.06 | <0.05 | 0.05 | 0.09 | 1.06% |
| Absolute Change in impurity (%) | 0.07 | 0.06 | N/A | 0.01 | 0.01 | 0.00 | 0.02 | 0.01 | 0.02 | 0.05 | 0.09 | |

Figure 14G

| Sample Description | Timepoint | SSID | RRT | 0.34 | 0.36 | 0.37 | 0.38 | 0.56 | 0.66 | 0.68 | 0.78 | 0.80 | 0.85 | 0.86 |
|---|---|---|---|---|---|---|---|---|---|---|---|---|---|---|
| 7wt Solids 25:75 Compund 1 HPMCAS-M in 6:4 DCM:MeOH Spray sol Lot: G8-936-10 | t=13day @40°C | 10085 | Peak Area | 0.22 | 0.11 | 0.04 | 0.07 | 0.06 | 0.02 | | 0.03 | 0.04 | 0.33 | 0.06 |
| | | | Report Peak Area | 0.22 | 0.11 | <0.05 | 0.07 | 0.06 | <0.05 | | <0.05 | <0.05 | 0.33 | 0.06 |
| | | | Absolute Change in impurity (%) | 0.03 | 0.05 | 0.01 | 0.05 | 0.02 | 0 | | 0.02 | 0.03 | 0.09 | 0.06 |
| | | | Peak Area | 0.23 | 0.12 | 0.04 | 0.06 | 0.06 | 0.02 | 0.02 | 0.02 | 0.05 | 0.33 | 0.06 |
| | | | Report Peak Area | 0.23 | 0.12 | <0.05 | 0.06 | 0.06 | <0.05 | <0.05 | <0.05 | 0.05 | 0.33 | 0.06 |
| | | | Absolute Change in impurity (%) | 0.04 | 0.06 | 0.01 | 0.04 | 0.02 | 0 | 0.02 | 0.03 | 0.02 | 0.09 | 0.06 |

| Sample Description | Timepoint | SSID | RRT | 0.88 | 0.92 | 0.94 | 0.96 | 1.00 | 1.02 | 1.10 | 1.43 | 1.47 | 1.52 | 1.56 | 1.58 | Total Impurities |
|---|---|---|---|---|---|---|---|---|---|---|---|---|---|---|---|---|
| 7wt Solids 25:75 Compund 1 HPMCAS-M in 6:4 DCM:MeOH Spray sol Lot: G8-936-10 | t=13day @40°C | 10085 | Peak Area | 0.03 | 1.09 | 0.10 | 0.10 | 96.48 | 0.06 | 0.04 | 0.03 | 0.38 | 0.57 | 0.10 | 0.04 | |
| | | | Report Peak Area | <0.05 | 1.09 | 0.10 | 0.10 | N/A | 0.06 | <0.05 | <0.05 | 0.38 | 0.57 | 0.10 | <0.05 | |
| | | | Absolute Change in Impurity (%) | 0.03 | 1.05 | 0.1 | 0.1 | N/A | 0.01 | 0 | 0.01 | 0.31 | 0.57 | 0.09 | 0.04 | 3.25% |
| | | | Peak Area | 0.03 | 1.08 | 0.1 | 0.1 | 96.44 | 0.06 | 0.05 | 0.03 | 0.39 | 0.57 | 0.09 | 0.04 | |
| | | | Report Peak Area | <0.05 | 1.08 | 0.1 | 0.1 | N/A | 0.06 | 0.05 | <0.05 | 0.39 | 0.57 | 0.09 | <0.05 | |
| | | | Absolute Change in Impurity (%) | 0.03 | 1.04 | 0.1 | 0.1 | N/A | 0.01 | 0.01 | 0.01 | 0.32 | 0.57 | 0.09 | 0.04 | 3.35% |

Figure 15A

Sample Description: GFB-887 API (Lot: TJ-GDF-9815-0-A-I) — Timepoint: t=0

| RRT | 0.85 | 0.91 | 1.00 | 1.02 | 1.05 | 1.10 | ND | 1.44 | 1.47 | ND | 1.58 | Total Impurities |
|---|---|---|---|---|---|---|---|---|---|---|---|---|
| % Peak Area | 0.40% | 0.04% | 98.74% | 0.08% | 0.02% | 0.04% | ND | 0.02% | 0.07% | ND | 0.03% | 0.97% |
| Reported % Peak Area | 0.40% | <0.05% | N/A | 0.08% | <0.05% | <0.05% | ND | <0.05% | 0.07% | ND | <0.05% | |

Sample Description: 25:75 GFB-887:HPMCAS-M Wet SDI Lot: D-18-078 — Timepoint: t=1day

| RRT | 0.85 | 0.91 | 1.00 | 1.02 | 1.05 | 1.10 | ND | 1.43 | 1.47 | ND | 1.58 | Total Impurities |
|---|---|---|---|---|---|---|---|---|---|---|---|---|
| % Peak Area | 0.40% | 0.03% | 98.78% | 0.07% | 0.02% | 0.05% | ND | 0.03% | 0.07% | ND | 0.04% | 0.93% |
| Reported % Peak Area | 0.40% | <0.05% | N/A | 0.07% | <0.05% | 0.05% | ND | <0.05% | 0.07% | ND | <0.05% | |
| Absolute Change in Impurity | 0.00% | 0.01% | N/A | 0.01% | 0.00% | 0.01% | 0.00% | 0.01% | 0.00% | 0.00% | 0.01% | |

Sample Description: 25:75 GFB-887:HPMCAS-M Wet SDI Lot: D-18-078 — Timepoint: t=5day

| RRT | 0.85 | 0.91 | 1.00 | 1.02 | 1.05 | 1.10 | 1.13 | 1.44 | 1.47 | 1.50 | 1.58 | Total Impurities |
|---|---|---|---|---|---|---|---|---|---|---|---|---|
| % Peak Area | 0.39% | 0.03% | 98.72% | 0.08% | 0.02% | 0.05% | 0.06% | 0.02% | 0.07% | 0.04% | 0.06% | 1.04% |
| Reported % Peak Area | 0.39% | <0.05% | N/A | 0.08% | <0.05% | 0.05% | 0.06% | <0.05% | 0.07% | <0.05% | 0.06% | |
| Absolute Change in Impurity | 0.01% | 0.01% | N/A | 0.00% | 0.00% | 0.01% | 0.06% | 0.00% | 0.00% | 0.04% | 0.03% | |

Sample Description: 25:75 GFB-887:HPMCAS-M Wet SDI Lot: D-18-078 — Timepoint: t=9day

| RRT | 0.85 | 0.91 | 1.00 | 1.02 | 1.05 | 1.10 | | ND | 1.47 | 1.50 | 1.58 | Total Impurities |
|---|---|---|---|---|---|---|---|---|---|---|---|---|
| % Peak Area | 0.41% | 0.04% | 98.73% | 0.08% | 0.02% | 0.05% | | ND | 0.07% | 0.03% | 0.06% | 1.02% |
| Reported % Peak Area | 0.41% | <0.05% | N/A | 0.08% | <0.05% | 0.05% | | ND | 0.07% | <0.05% | 0.06% | |
| Absolute Change in Impurity | 0.01% | 0.00% | N/A | 0.00% | 0.00% | 0.01% | 0.00% | 0.02% | 0.00% | 0.03% | 0.03% | |

Sample Description: 25:75 GFB-887:HPMCAS-M Wet SDI Lot: D-18-078 — Timepoint: t=15day

| RRT | 0.85 | 0.91 | 1.00 | 1.02 | 1.05 | 1.10 | ND | 1.43 | 1.47 | 1.49 | 1.58 | Total Impurities |
|---|---|---|---|---|---|---|---|---|---|---|---|---|
| % Peak Area | 0.42% | 0.03% | 98.77% | 0.07% | 0.03% | 0.07% | ND | 0.02% | 0.07% | 0.04% | 0.05% | 1.02% |
| Reported % Peak Area | 0.42% | <0.05% | N/A | 0.07% | <0.05% | 0.07% | ND | <0.05% | 0.07% | <0.05% | 0.05% | |
| Absolute Change in Impurity | 0.02% | 0.01% | N/A | 0.01% | 0.01% | 0.03% | 0.00% | 0.00% | 0.00% | 0.04% | 0.02% | |

Figure 19
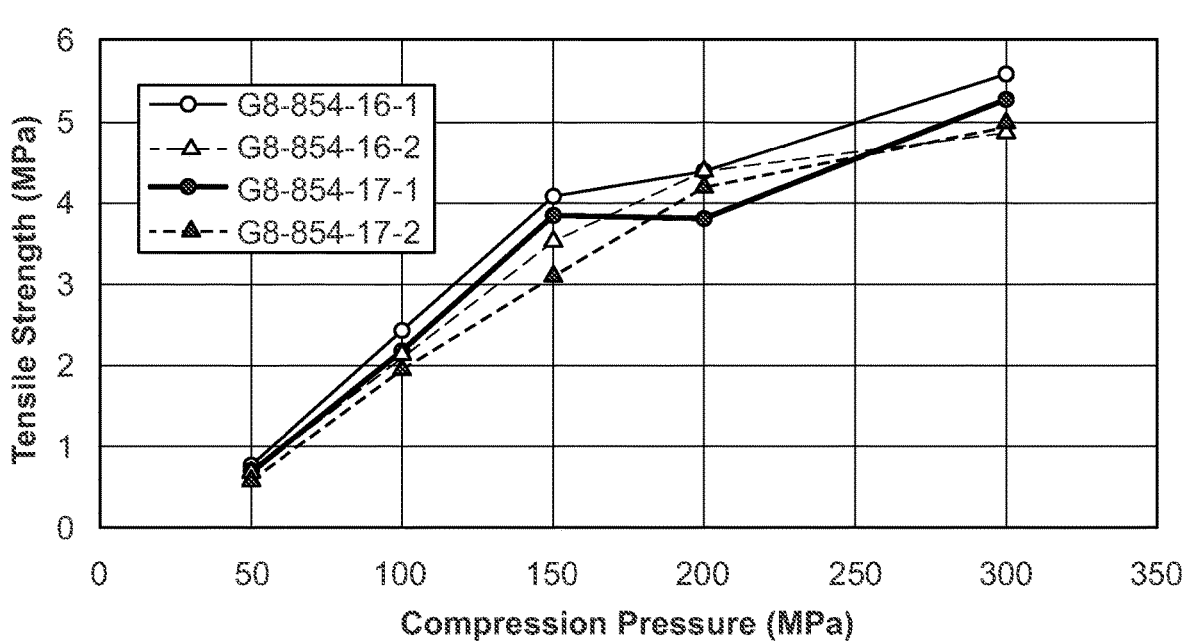
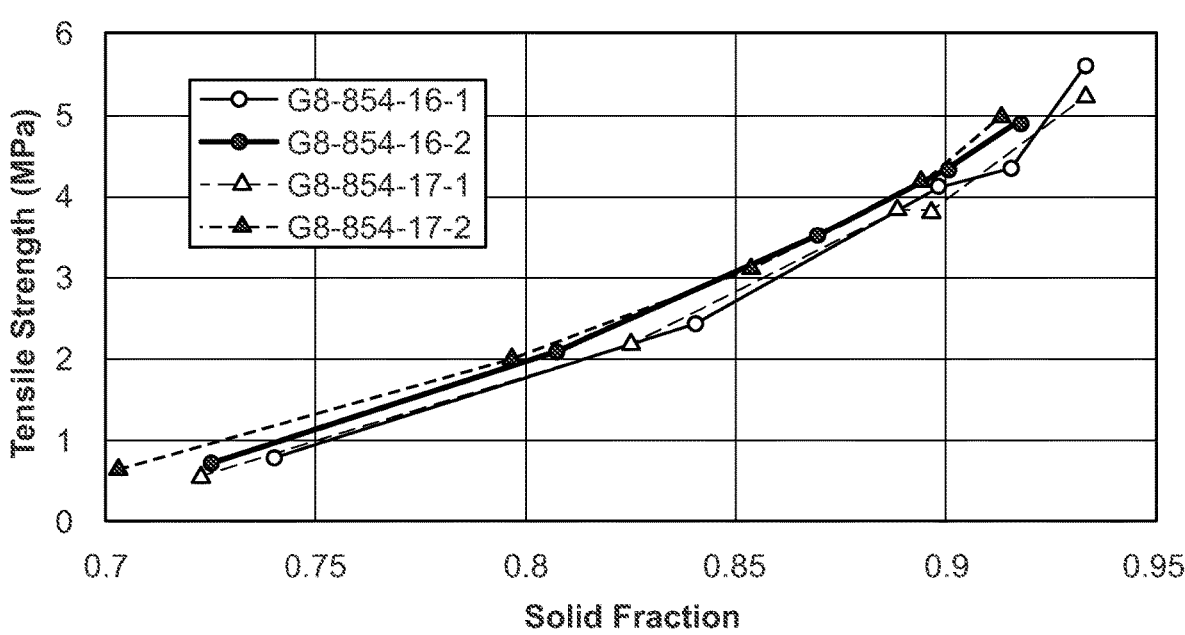

Figure 19 (cont.)
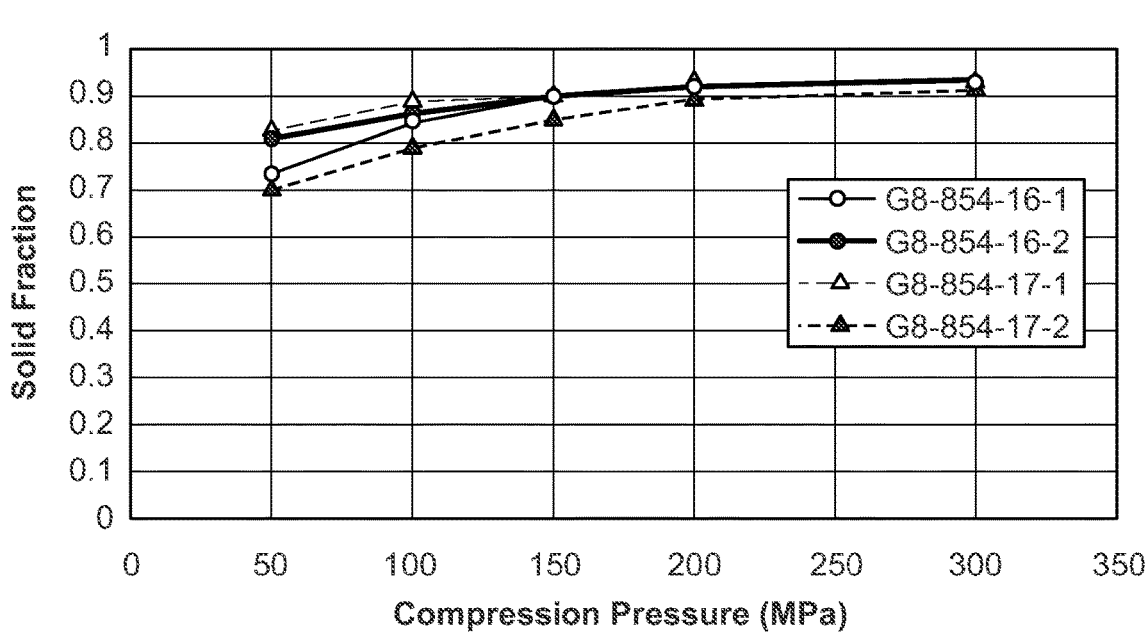
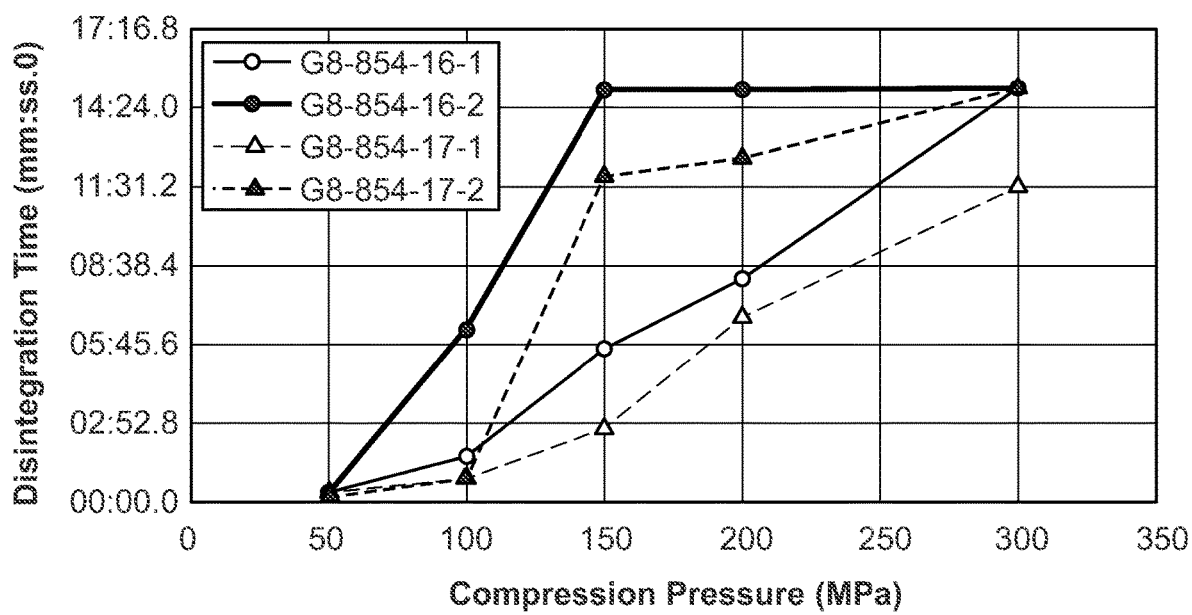

Figure 20 (cont.)

| Sample | Lot# | Drug CmaxGR (µgA/mL) | Drug CmaxFaSSIF (µgA/mL) | Drug AUC35-210 FaSSIF (min*µgA/mL) | Drug Cmin (µgA/mL) |
|---|---|---|---|---|---|
| 50 mgA GFB-887 Tablet/lactose/Ac-Di-Sol, 4 WK/25C/60%RH/CLOSED | G8-854-16-1 | 18 | 36.7 | 4700 | 20.9 |
| 50 mgA GFB-887 Tablet/lactose/Ac-Di-Sol, 4 WK/40C/75%RH/CLOSED | G8-854-16-1 | 19 | 37.7 | 4900 | 21.7 |
| 50 mgA GFB-887 Tablet/lactose/Ac-Di-Sol, 4 WK/25C/60%RH/OPEN | G8-854-16-1 | 21 | 42.3 | 4800 | 22.7 |
| 50 mgA GFB-887 Tablet/lactose/Ac-Di-Sol, 4 WK/40C/75%RH/OPEN | G8-854-16-1 | 16 | 32.4 | 4700 | 19.8 |
| 50 mgA GFB-887 Tablet/lactose/Ac-Di-Sol, 4 WK/25C/60%RH/CLOSED (Free) | G8-854-16-1 | 8 | 25.0 | 3100 | 14.3 |
| 50 mgA GFB-887 Tablet/lactose/Ac-Di-Sol, 4 WK/40C/75%RH/CLOSED (Free) | G8-854-16-1 | 13 | 29.6 | 4100 | 17.7 |
| 50 mgA GFB-887 Tablet/lactose/Ac-Di-Sol, 4 WK/25C/60%RH/OPEN (Free) | G8-854-16-1 | 8 | 28.0 | 3200 | 15.6 |
| 50 mgA GFB-887 Tablet/lactose/Ac-Di-Sol, 4 WK/40C/75%RH/OPEN (Free) | G8-854-16-1 | 7 | 20.6 | 3200 | 15.5 |

Figure 21 (cont.)

| Sample | Lot# | Drug CmaxGR (µgA/mL) | Drug CmaxFaSSIF (µgA/mL) | Drug AUC5-210 FaSSIF (min*µgA/mL) | Drug C2in (µgA/mL) |
|---|---|---|---|---|---|
| 50 mgA GFB-887 Tablet/mannitol/Ac-Di-Sol, 4 WK/25C/60%RH/CLOSED | G8-854-17-1 | 20 | 38.8 | 5300 | 22.4 |
| 50 mgA GFB-887 Tablet/mannitol/Ac-Di-Sol, 4 WK/40C/75%RH/CLOSED | G8-854-17-1 | 19 | 36.0 | 4900 | 20.5 |
| 50 mgA GFB-887 Tablet/mannitol/Ac-Di-Sol, 4 WK/25C/60%RH/OPEN | G8-854-17-1 | 19 | 39.3 | 4500 | 19.3 |
| 50 mgA GFB-887 Tablet/mannitol/Ac-Di-Sol, 4 WK/40C/75%RH/OPEN | G8-854-17-1 | 15 | 36.8 | 5200 | 24.6 |
| 50 mgA GFB-887 Tablet/mannitol/Ac-Di-Sol, 4 WK/25C/60%RH/CLOSED (Free) | G8-854-17-1 | 8 | 23.9 | 3200 | 17.1 |
| 50 mgA GFB-887 Tablet/mannitol/Ac-Di-Sol, 4 WK/40C/75%RH/CLOSED (Free) | G8-854-17-1 | 8 | 22.4 | 3200 | 15.3 |
| 50 mgA GFB-887 Tablet/mannitol/Ac-Di-Sol, 4 WK/25C/60%RH/OPEN (Free) | G8-854-17-1 | 8 | 24.3 | 3000 | 14.5 |
| 50 mgA GFB-887 Tablet/mannitol/Ac-Di-Sol, 4 WK/40C/75%RH/OPEN (Free) | G8-854-17-1 | 5 | 22.4 | 3200 | 15.9 |

Figure 22
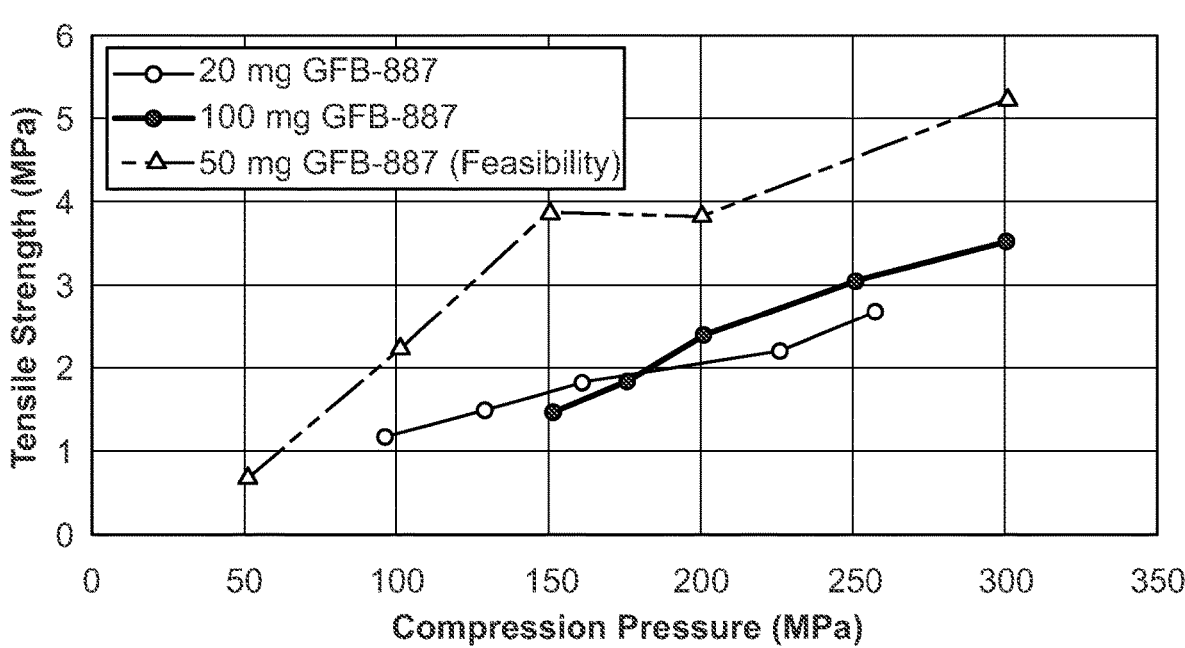
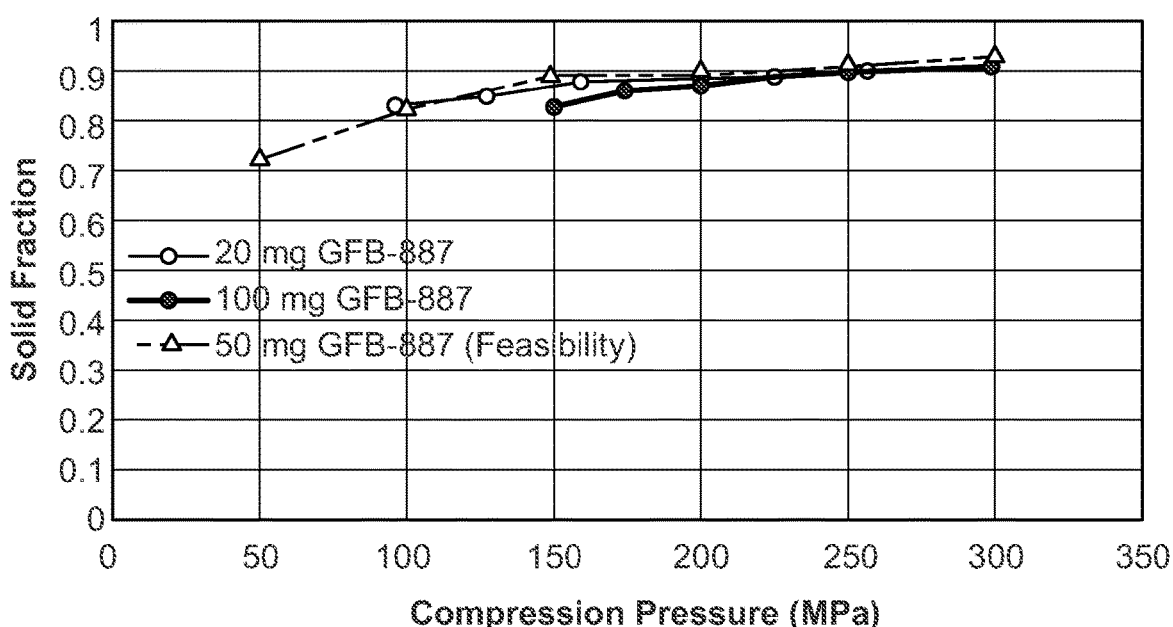

Figure 22 (cont.)
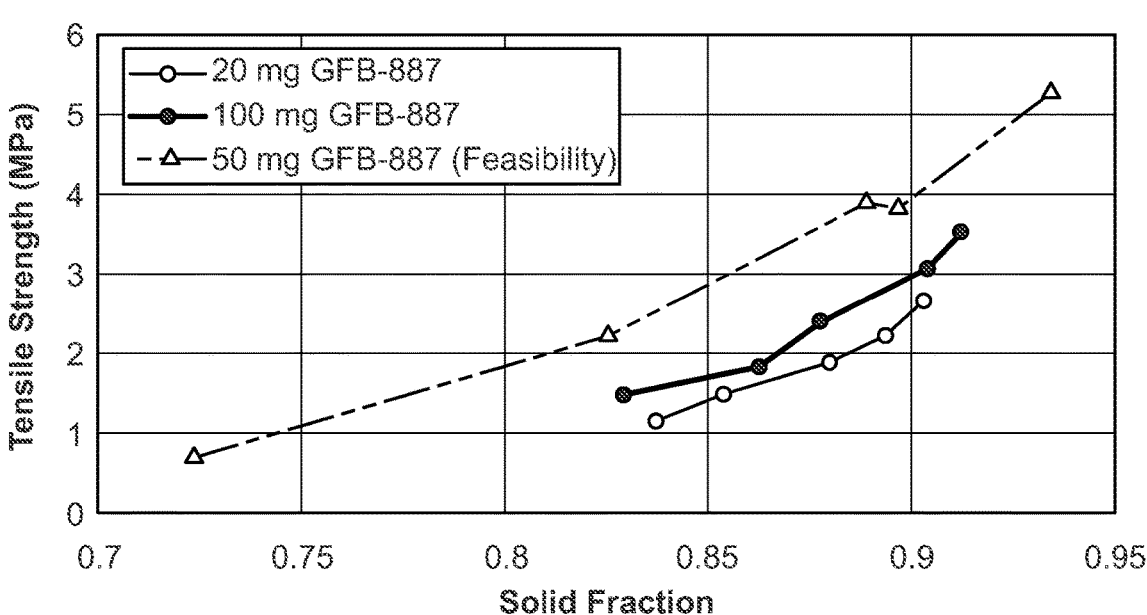
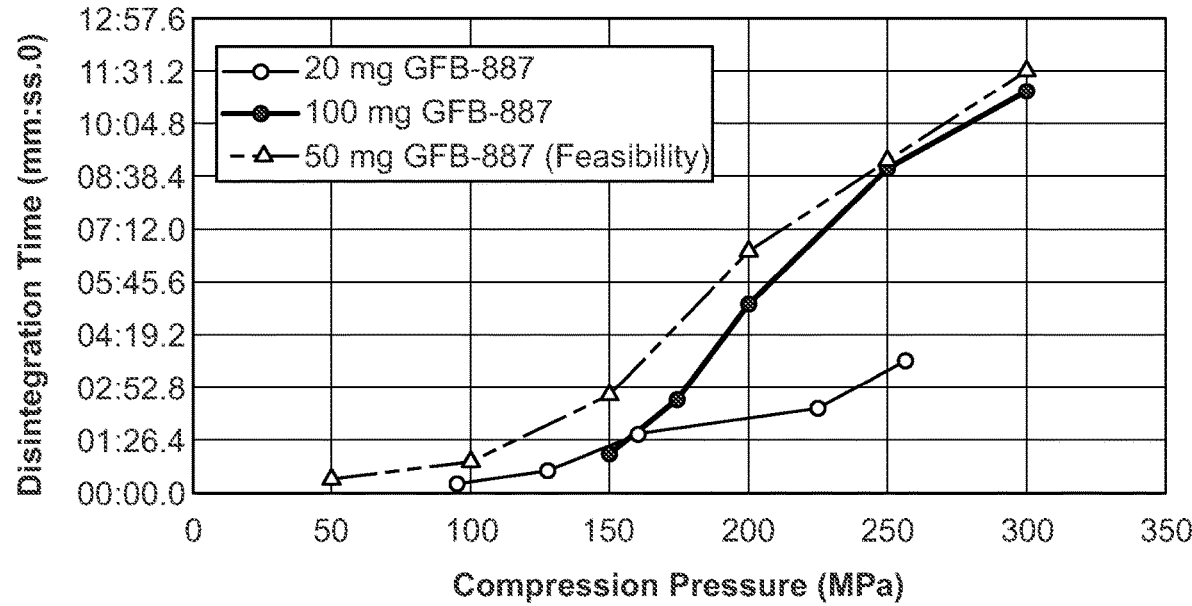

Dissolution Plot: GFB-887

SampleName 200 mPa Tab

Dissolved Percent for Component GFB-887 Channel: DAD .0.0

| | Bath | Vessel | Injection | 5.0 min | 15.0 min | 30.0 min | 45.0 min | 60.0 min | 75.0 min |
|---|---|---|---|---|---|---|---|---|---|
| 1 | A | 1 | 1 | 12 | 40 | 70 | 85 | 93 | 98 |
| 2 | A | 2 | 1 | 16 | 47 | 74 | 85 | 91 | 95 |
| 3 | A | 3 | 1 | 15 | 43 | 72 | 85 | 92 | 95 |
| Mean | | | | 14 | 43 | 72 | 85 | 92 | 96 |
| Max | | | | 16 | 47 | 74 | 85 | 93 | 98 |
| Min | | | | 12 | 40 | 70 | 85 | 91 | 95 |
| %RSD | | | | 12.153 | 8.940 | 2.327 | 0.183 | 1.331 | 1.687 |
| Std. Dev | | | | 1.749 | 3.872 | 1.680 | 0.156 | 1.221 | 1.617 |

Dissolution Plot: GFB-887

SampleName 250 mPa Tab

Dissolved Percent for Component GFB-887 Channel: DAD .0.0

| | Bath | Vessel | Injection | 5.0 min | 15.0 min | 30.0 min | 45.0 min | 60.0 min | 75.0 min |
|---|---|---|---|---|---|---|---|---|---|
| 1 | A | 4 | 1 | 12 | 30 | 61 | 81 | 90 | 98 |
| 2 | A | 5 | 1 | 12 | 30 | 61 | 79 | 89 | 97 |
| 3 | A | 6 | 1 | 11 | 29 | 60 | 79 | 89 | 97 |
| Mean | | | | 11 | 30 | 61 | 80 | 90 | 97 |
| Max | | | | 12 | 30 | 61 | 81 | 90 | 98 |
| Min | | | | 11 | 29 | 60 | 79 | 89 | 97 |
| %RSD | | | | 5.163 | 1.679 | 0.745 | 0.991 | 0.620 | 0.684 |
| Std. Dev | | | | 0.588 | 0.502 | 0.453 | 0.790 | 0.556 | 0.665 |

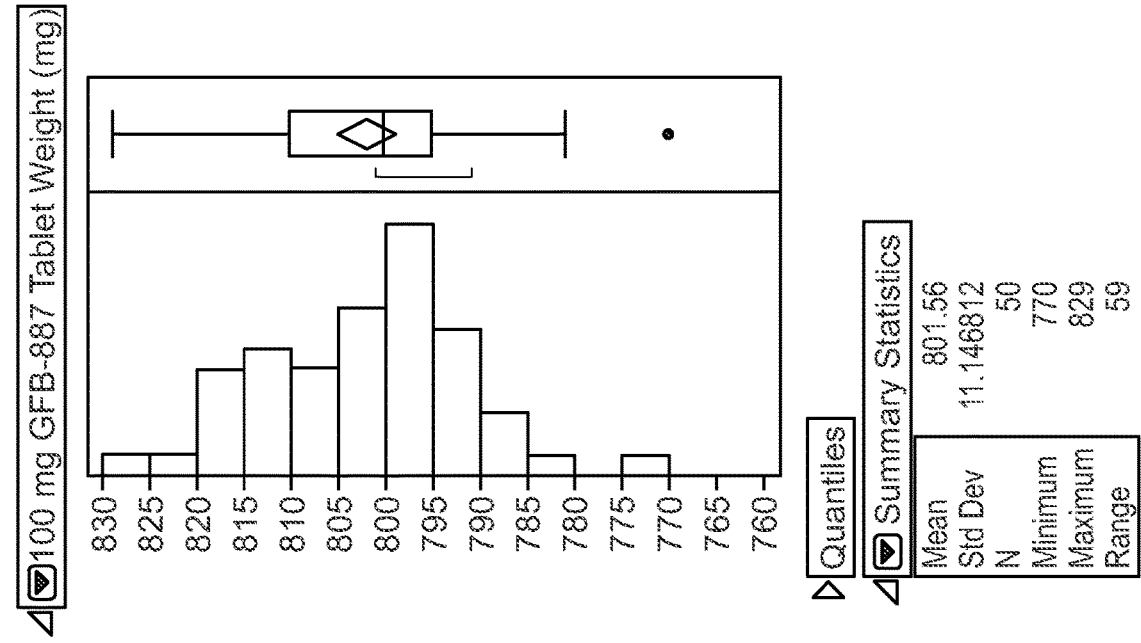
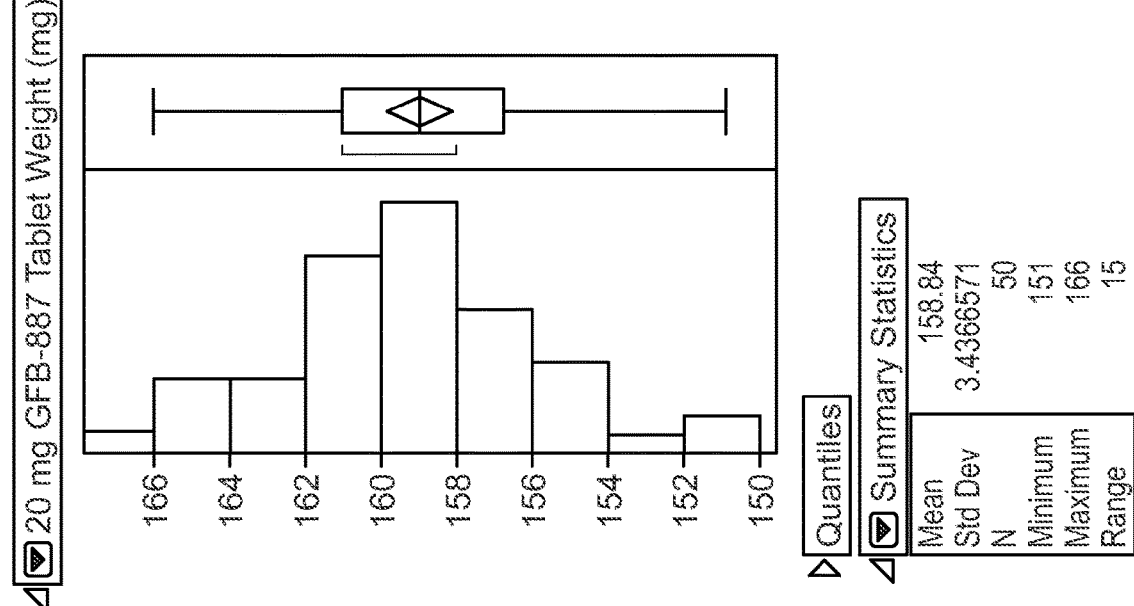
Figure 30

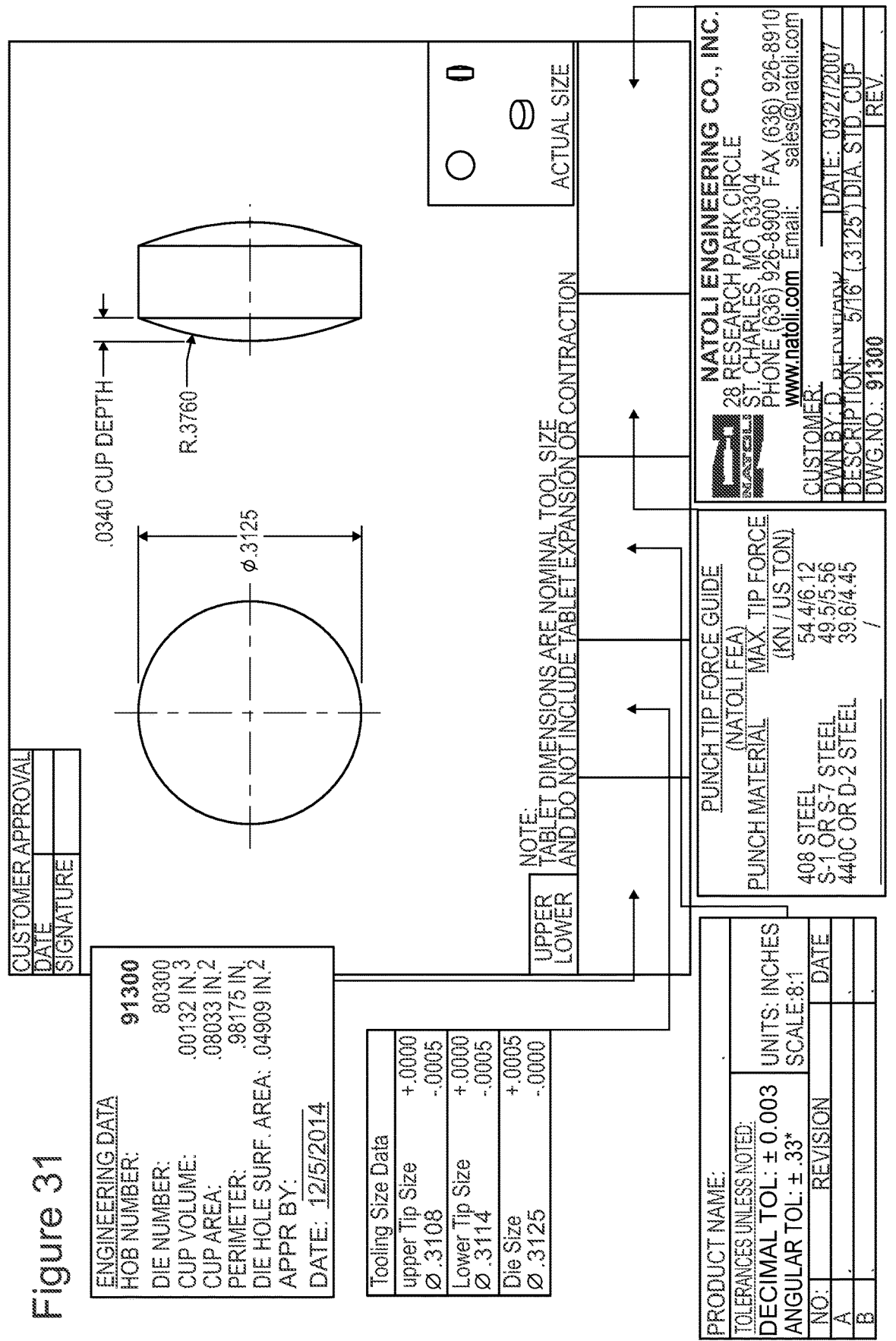

Figure 31

ACTUAL SIZE

.0340 CUP DEPTH

R.3760

Ø.3125

NOTE:
TABLET DIMENSIONS ARE NOMINAL TOOL SIZE
AND DO NOT INCLUDE TABLET EXPANSION OR CONTRACTION

UPPER
LOWER

CUSTOMER APPROVAL
DATE
SIGNATURE

ENGINEERING DATA
HOB NUMBER:              91300
DIE NUMBER:              80300
CUP VOLUME:            .00132 IN.3
CUP AREA:              .08033 IN.2
PERIMETER:            .98175 IN.
DIE HOLE SURF. AREA: .04909 IN.2
APPR BY:
DATE: 12/5/2014

| Tooling Size Data | | |
|---|---|---|
| upper Tip Size | +.0000 | |
| Ø .3108 | -.0005 | |
| Lower Tip Size | +.0000 | |
| Ø .3114 | -.0005 | |
| Die Size | +.0005 | |
| Ø .3125 | -.0000 | |

NATOLI ENGINEERING CO., INC.
28 RESEARCH PARK CIRCLE
ST. CHARLES, MO. 63304
PHONE (636) 926-8900  FAX (636) 926-8910
www.natoli.com  Email:  sales@natoli.com CUSTOMER:
DWN BY: D.                              DATE: 03/27/2007
DESCRIPTION:  5/16" (.3125") DIA STD CUP
DWG.NO.: 91300                          REV.

| PUNCH TIP FORCE GUIDE (NATOLI FEA) | |
|---|---|
| PUNCH MATERIAL | MAX. TIP FORCE (KN / US TON) |
| 408 STEEL | 54.4/6.12 |
| S-1 OR S-7 STEEL | 49.5/5.56 |
| 440C OR D-2 STEEL | 39.6/4.45 |

PRODUCT NAME:
TOLERANCES UNLESS NOTED:
DECIMAL TOL: ± 0.003          UNITS: INCHES
ANGULAR TOL: ±.33°            SCALE:8:1

| REVISION | | | |
|---|---|---|---|
| NO: | | | DATE |
| A | | | |
| B | | | |

Figure 33

CERTIFICATE OF TESTING

ThermoFisher
S C I E N T I F I C

| | |
|---|---|
| Material Description: | GFB-887 Tablets, 20mg |
| Patheon Lot #: | G8-854-34 |
| Date of Manufacture: | 12Dec2018 |
| Expiration/Review Date: | NA |
| Storage: | Room Temperature |
| Certificate Rev #: | 2 |
| Page: | 1 of 3 |

Note: Contains a new drug for investigational use only in laboratory research animals, or for *in vitro* tests. Not for use in humans.

| Test | Procedure/LNB Ref. | Acceptance Criteria | Result | | |
|---|---|---|---|---|---|
| Appearance (Visual) | AM-0002/ G8-936-32 | White to off-white to light brown standard round convex tablet; may or may not be mottled | Biconvex oval tablet, off-white and slightly mottled | | |
| Identification (HPLC, Retention Time Comparsion) | AM-0236 (Draft)/ G8-936-26 | The retention time of sample conforms to the reference standard | Conforms to Reference - 100% | | |
| Assay (HPLC) | AM-0236 (Draft)/ G8-936-26 | 90.0% - 110.0% Label Claim | 98.7% | | |
| Total Impurities and Related Substances (HPLC) | AM-0236 (Draft)/ G8-936-26 | ≤3.0%(% area) | 0.81% | | |
| Individual Impurities and Related Substances (HPLC)1<br><br>a. Individual Specified Impurities<br><br>b. Individual Unspecified Impurities or Related Substances | AM-0236 (Draft)/ G8-936-26 | Report Results (RRT and % area)<br>a.<br>Individual Specified Impurities or Related Substances<br>GDF-9815-IMP1 Peak 1 (RRT 0.35): ≤0.2%<br>GDF-9815-IMP1 Peak 2 (RRT 0.36): ≤0.5%<br>RRT 0.40: ≤0.2%<br>GDF-9815-IMP4 (RRT 0.85): ≤1.0%<br>RRT 1.02: ≤0.2%<br>RRT 1.10: ≤0.2%<br>RRT 1.48: ≤0.3%<br>b.<br>Individual Unspecified Impirities or Related Substances: ≤0.2% | RRT | %Peak Area | |
| | | | GDF-9815-IMP1 peak 1: 0.34 | 0.18% | |
| | | | GDF-9815-IMP1 peak 2: 0.36 | 0.10% | |
| | | | 0.37 | <0.05% | |
| | | | 0.38 | <0.05% | |
| | | | 0.56 | <0.05% | |
| | | | 0.66 | <0.05% | |
| | | | 0.80 | <0.05% | |
| | | | GDF-9815-IMP4: 0.85 | 0.40% | |
| | | | 0.91 | 0.05% | |
| | | | 1.02 | 0.08% | |
| | | | 1.44 | <0.05% | |
| | | | 1.50 | <0.05% | |
| | | | 1.59 | <0.05% | |

Figure 33 (cont.)

ThermoFisher
S C I E N T I F I C

CERTIFICATE OF TESTING

| | |
|---|---|
| Material Description: | GFB-887 Tablets, 20mg |
| Patheon Lot #: | G8-854-34 |
| Date of Manufacture: | 12Dec2018 |
| Expiration/Review Date: | NA |
| Storage: | Room Temperature |
| Certificate Rev #: | 2 |
| Page: | 2 of 3 |

Note: Contains a new drug for investigational use only in laboratory research animals, or for *in vitro* tests. Not for use in humans.

| Test | Procedure/LNB Ref. | Acceptance Criteria | Result | | |
|---|---|---|---|---|---|
| Uniformity of Dosage (HPLC) | AM-0236 (Draft)/ USP<905>/ G8-936-50 | Meet USP <905>criteria (Report acceptance Value [AV]) | | Mean % LC | AV |
| | | | Beginning | 98.0 | 5.7 |
| | | | Middle | 96.9 | 5.5 |
| | | | End | 93.3 | 14.5 |
| Dissolution | AM-0235 (Draft)/ USP<711>/ G8-936-38 | Report Results (Average and %RSD of %Dissolved at each time point) | Timepoint (min) | Dissolved % | %RSD |
| | | | 5 | 15 | 13 |
| | | | 10 | 33 | 22 |
| | | | 15 | 48 | 11 |
| | | | 30 | 71 | 4 |
| | | | 45 | 84 | 3 |
| | | | 60 | 91 | 2 |
| | | | 75 | 96 | 3 |
| Water Content (KF) | AM-0233 (Draft)/ USP<921>/ G8-936-30 | NMT 7% (wt%) | 1.54% | | |

Figure 33 (cont.)

ThermoFisher
S C I E N T I F I C

CERTIFICATE OF TESTING

Material Description:    GFB-887 Tablets, 20mg
Patheon Lot #:    G8-854-34
Date of Manufacture:    12Dec2018
Expiration/Review Date:   NA
Storage:    Room Temperature
Certificate Rev #:    2
Page:    3 of 3

Note: Contains a new drug for investigational use only in laboratory research animals, or for *in vitro* tests. Not for use in humans.

Revision History:

| Revision # | Change | Date |
|---|---|---|
| 00 | New document | 08Mar2019 |
| 01 | Omit RRT 1.76 SSF peak | 14May2019 |
| 02 | Update SEM Figure Title | 09May2019 |

Prepared By/Date:     Ashley Moon
I am the author of this document
2019.05.09 13:35:14-07'00'

Reviewed By/Date:     Kevin Carman
I am approving this document
2019.05.09 13:45:17-07'00'

Figure 34

ThermoFisher
SCIENTIFIC

CERTIFICATE OF TESTING

Material Description:  GFB-887 Tablets, 100mg
Patheon Lot #:  G8-854-36
Date of Manufacture:  12Dec2018
Expiration/Review Date:  NA
Storage:  Room Temperature
Certificate Rev #:  2
Page:  1 of 3

Note: Contains a new drug for investigational use only in laboratory research animals, or for *in vitro* tests. Not for use in humans.

| Test | Procedure/LNB Ref. | Acceptance Criteria | Result | | |
|---|---|---|---|---|---|
| Appearance(Visual) | AM-0002/ G8-936-32 | White to off-white to light brown standard round convex tablet; may or may not be mottled | Biconvex oval tablet, off-white and slightly mottled | | |
| Identification (HPLC, Retention Time Comparsion) | AM-0236 (Draft)/ G8-936-26 | The retention time of ample conforms to the reference standard | Conforms to Reference - 100% | | |
| Assay (HPLC) | AM-0236 (Draft)/ G8-936-26 | 90.0%-110.0% Label Claim | 99.2% | | |
| Total Impurities and Related Substances (HPLC) | AM-0236 (Draft)/ G8-936-26 | ≤3.0%(% area) | 0.81% | | |
| Individual Impurities and Related Substances (HPLC)1<br><br>a. Individual Specified Impurities<br><br>b. Individual Unspecified Impurities or Related Substances | AM-0236 (Draft)/ G8-936-26 | Report Results (RRT and % area)<br>a.<br>Individual Specified Impurities or Related Substances<br>GDF-9815-IMP1 Peak 1 (RRT 0.35): ≤0.2%<br>GDF-9815-IMP1 Peak 2 (RRT 0.36): ≤0.5%<br>RRT 0.40: ≤0.2%<br>GDF-9815-IMP4 (RRT 0.85): ≤1.0%<br>RRT 1.02: ≤0.2%<br>RRT 1.10: ≤0.2%<br>RRT 1.48: ≤0.3%<br>b.<br>Individual Unspecified Impirities or Related Substances: ≤0.2% | RRT | %Peak Area | |
| | | | GDF-9815-IMP1 peak 1: 0.34 | 0.18% | |
| | | | GDF-9815-IMP1 peak 2: 0.36 | 0.10% | |
| | | | 0.37 | <0.05% | |
| | | | 0.38 | <0.05% | |
| | | | 0.56 | <0.05% | |
| | | | 0.66 | <0.05% | |
| | | | 0.80 | <0.05% | |
| | | | GDF-9815-IMP4: 0.85 | 0.40% | |
| | | | 0.91 | 0.05% | |
| | | | 1.02 | 0.08% | |
| | | | 1.44 | <0.05% | |
| | | | 1.50 | <0.05% | |
| | | | 1.59 | <0.05% | |

Figure 34 (cont.)

ThermoFisher
S C I E N T I F I C

CERTIFICATE OF TESTING

Material Description:      GFB-887 Tablets, 100mg
Patheon Lot #:             G8-854-36
Date of Manufacture:       12Dec2018
Expiration/Review Date:    NA
Storage:                   Room Temperature
Certificate Rev #:         2
Page:                      2 of 3

Note: Contains a new drug for investigational use only in laboratory research animals, or for *in vitro* tests. Not for use in humans.

| Test | Procedure/LNB Ref. | Acceptance Criteria | Result | | |
|---|---|---|---|---|---|
| Uniformity of Dosage (HPLC) | AM-0236 (Draft)/ USP<905>/ G8-936-50 | Meet USP<905> criteria (Report acceptance Value [AV]) | | Mean % LC | AV |
| | | | Beginning | 98.9 | 2.0 |
| | | | Middle | 98.8 | 3.7 |
| | | | End | 95.4 | 7.1 |
| Dissolution | AM-0235 (Draft)/ USP<711>/ G8-936-38 | Report Results (Average and %RSD of %Dissolved at each time point) | Timepoint (min) | Dissolved % | %RSD |
| | | | 5 | 15 | 8 |
| | | | 10 | 28 | 7 |
| | | | 15 | 44 | 8 |
| | | | 30 | 71 | 3 |
| | | | 45 | 84 | 2 |
| | | | 60 | 91 | 2 |
| | | | 75 | 96 | 2 |
| Water Content (KF) | AM-0233 (Draft)/ USP<921>/ G8-936-30 | NMT 7% (wt%) | 1.47% | | |

Figure 34 (cont.)

ThermoFisher
SCIENTIFIC

CERTIFICATE OF TESTING

Material Description:      GFB-887 Tablets, 100mg
Patheon Lot #:             G8-854-36
Date of Manufacture:       12Dec2018
Expiration/Review Date:    NA
Storage:                   Room Temperature
Certificate Rev #:         2
Page:                      3 of 3

Note: Contains a new drug for investigational use only in laboratory research animals, or for *in vitro* tests. Not for use in humans.

Revision History:

| Revision # | Change | Date |
|---|---|---|
| 00 | New document | 08Mar2019 |
| 01 | Omit RRT 1.76 SSF peak | 14May2019 |
| 02 | Updated Material Description | 09May2019 |

Prepared By/Date:

Ashley Moon
I am the author of this document
2019.05.09 13:38:25-07'00'

Reviewed By/Date:

Kevin Carman
I am approving this document
2019.05.09 13:44:32-07'00'

SPRAY-DRIED FORMULATION OF A PYRIDAZINONE TRPC5 INHIBITOR

RELATED APPLICATIONS

This application is a National Stage Entry of International Application No. PCT/US20/027673, filed Apr. 10, 2020; which claims the benefit of priority to U.S. Provisional Application No. 62/832,632, filed Apr. 11, 2019; and U.S. Provisional Application No. 62/991,315, filed Mar. 18, 2020.

BACKGROUND

Proteinuria is a condition in which an excessive amount of protein in the blood leaks into the urine. Proteinuria can progress from a loss of 30 mg of protein in the urine over a 24-hour period (called microalbuminuria) to >300 mg/day (called macroalbuminuria), before reaching levels of 3.5 grams of protein or more over a 24-hour period, or 25 times the normal amount. Proteinuria occurs when there is a malfunction in the kidney's glomeruli, causing fluid to accumulate in the body (edema). Prolonged protein leakage has been shown to result in kidney failure. Nephrotic Syndrome (NS) disease accounts for approximately 12% of prevalent end stage renal disease cases at an annual cost in the United States of more than $3 billion. Approximately 5 out of every 100,000 children are diagnosed with NS every year and 15 out of every 100,000 children are living with it today. For patients who respond positively to treatment, the relapse frequency is extremely high. Ninety % of children with Nephrotic Syndrome will respond to treatment, however, an estimated 75% will relapse. There is a need for more effective methods of treating, or reducing risk of developing, kidney disease, e.g., proteinuria.

Mammalian TRP channel proteins form six-transmembrane cation-permeable channels which may be grouped into six subfamilies on the basis of amino acid sequence homology (TRPC, TRPV, TRPM, TRPA, TRPP, and TRPML). Recent studies of TRP channels indicate that they are involved in numerous fundamental cell functions and are considered to play an important role in the pathophysiology of many diseases. Many TRPs are expressed in kidney along different parts of the nephron and growing evidence suggest that these channels are involved in hereditary, as well as acquired kidney disorders. TRPC6, TRPM6, and TRPP2 have been implicated in hereditary focal segmental glomerulosclerosis (FSGS), hypomagnesemia with secondary hypocalcemia (HSH), and polycystic kidney disease (PKD), respectively.

The non-selective $Ca^{2+}$-permeable Transient Receptor Potential (TRP) channels act as sensors that transduce extracellular cues to the intracellular environment in diverse cellular processes, including actin remodeling and cell migration (Greka et al., Nat Neurosci 6, 837-845, 2003; Ramsey et al., Annu Rev Physiol 68, 619-647, 2006; Montell, Pflugers Arch 451, 19-28, 2005; Clapham, Nature 426, 517-524, 2003). Dynamic rearrangement of the actin cytoskeleton relies on spatiotemporally regulated $Ca^{2+}$ influx (Zheng and Poo, Annu Rev Cell Dev Biol 23, 375-404, 2007); Brandman and Meyer, Science 322, 390-395, 2008); Collins and Meyer, Dev Cell 16, 160-161, 2009) and the small GTPases RhoA and Rac1 serve as key modulators of these changes (Etienne-Manneville and Hall, Nature 420, 629-635, 2002); Raftopoulou and Hall, Dev Biol 265, 23-32, 2004). RhoA induces stress fiber and focal adhesion formation, while Rac1 mediates lamellipodia formation (Etienne- Manneville and Hall, Nature 420, 629-635, 2002). The Transient Receptor Potential Cation Channel, subfamily C, member 5 (TRPC5) acts in concert with TRPC6 to regulate $Ca^{2+}$ influx, actin remodeling, and cell motility in kidney podocytes and fibroblasts. TRPC5-mediated $Ca^{2+}$ influx increases Rac1 activity, whereas TRPC6-mediated $Ca^{2+}$ influx promotes RhoA activity. Gene silencing of TRPC6 channels abolishes stress fibers and diminishes focal contacts, rendering a motile, migratory cell phenotype. In contrast, gene silencing of TRPC5 channels rescues stress fiber formation, rendering a contractile cell phenotype. The results described herein unveil a conserved signaling mechanism whereby TRPC5 and TRPC6 channels control a tightly regulated balance of cytoskeletal dynamics through differential coupling to Rac1 and RhoA.

$Ca^{2+}$-dependent remodeling of the actin cytoskeleton is a dynamic process that drives cell migration (Wei et al., Nature 457, 901-905, 2009). RhoA and Rac1 act as switches responsible for cytoskeletal rearrangements in migrating cells (Etienne-Manneville and Hall, Nature 420, 629-635, 2002); Raftopoulou and Hall, Dev Biol 265, 23-32, 2004). Activation of Rac1 mediates a motile cell phenotype, whereas RhoA activity promotes a contractile phenotype (Etienne-Manneville and Hall, Nature 420, 629-635, 2002). $Ca^{2+}$ plays a central role in small GTPase regulation (Aspenstrom et al., Biochem J 377, 327-337, 2004). Spatially and temporally restricted flickers of $Ca^{2+}$ are enriched near the leading edge of migrating cells (Wei et al., Nature 457, 901-905, 2009). $Ca^{2+}$ microdomains have thus joined local bursts in Rac1 activity (Gardiner et al., Curr Biol 12, 2029-2034, 2002; Machacek et al., Nature 461, 99-103, 2009) as critical events at the leading edge. To date, the sources of $Ca^{2+}$ influx responsible for GTPase regulation remain largely elusive. TRP (Transient Receptor Potential) channels generate time and space-limited $Ca^{2+}$ signals linked to cell migration in fibroblasts and neuronal growth cones0. Specifically, TRPC5 channels are known regulators of neuronal growth cone guidance1 and their activity in neurons is dependent on PI3K and Rac1 activity (Bezzerides et al., Nat Cell Biol 6, 709-720, 2004).

Podocytes are neuronal-like cells that originate from the metanephric mesenchyme of the kidney glomerulus and are essential to the formation of the kidney filtration apparatus (Somlo and Mundel, Nat Genet. 24, 333-335, 2000; Fukasawa et al., J Am Soc Nephrol 20, 1491-1503, 2009). Podocytes possess an exquisitely refined repertoire of cytoskeletal adaptations to environmental cues (Somlo and Mundel, Nat Genet 24, 333-335, 2000; Garg et al., Mol Cell Biol 27, 8698-8712, 2007; Verma et al., J Clin Invest 116, 1346-1359, 2006; Verma et al., J Biol Chem 278, 20716-20723, 2003; Barletta et al., J Biol Chem 278, 19266-19271, 2003; Holzman et al., Kidney Int 56, 1481-1491, 1999; Ahola et al., Am J Pathol 155, 907-913, 1999; Tryggvason and Wartiovaara, N Engl J Med 354, 1387-1401, 2006; Schnabel and Farquhar, J Cell Biol 111, 1255-1263, 1990; Kurihara et al., Proc Natl Acad Sci USA 89, 7075-7079, 1992). Early events of podocyte injury are characterized by dysregulation of the actin cytoskeleton (Faul et al., Trends Cell Biol 17, 428-437, 2007; Takeda et al., J Clin Invest 108, 289-301, 2001; Asanuma et al., Nat Cell Biol 8, 485-491, 2006) and $Ca^{2+}$ homeostasis (Hunt et al., J Am Soc Nephrol 16, 1593-1602, 2005; Faul et al., Nat Med 14, 931-938, 2008). These changes are associated with the onset of proteinuria, the loss of albumin into the urinary space, and ultimately kidney failure (Tryggvason and Wartiovaara, N Engl J Med 354, 1387-1401, 2006). The vasoactive hormone Angiotensin II induces $Ca^{2+}$ influx in podocytes, and prolonged treatment results in loss of stress fibers (Hsu et al., J Mol Med 86, 1379-1394, 2008). While there is a recognized link between $Ca^{2+}$ influx and cytoskeletal reorganization, the mechanisms by which the podocyte senses and transduces extracellular cues that modulate cell shape and motility remain elusive. TRP Canonical 6 (TRPC6) channel mutations have been linked to podocyte injury (Winn et al., Science 308, 1801-1804, 2005; Reiser et al., Nat Genet 37, 739-744, 2005; Moller et al., J Am Soc Nephrol 18, 29-36, 2007; Hsu et al., Biochim Biophys Acta 1772, 928-936, 2007), but little is known about the specific pathways that regulate this process. Moreover, TRPC6 shares close homology with six other members of the TRPC channel family (Ramsey et al., Annu Rev Physiol 68, 619-647, 2006; Clapham, Nature 426, 517-524, 2003). TRPC5 channels antagonize TRPC6 channel activity to control a tightly regulated balance of cytoskeletal dynamics through differential coupling to distinct small GTPases.

Hence, there is a need for additional inhibitors of TRPC5.

SUMMARY

One aspect of the invention is compositions for manufacturing a spray-dried dispersion, the composition comprising 4-chloro-5-(4-(4-fluoro-2-(trifluoromethyl)phenoxy)-5,8-dihydropyrido[3,4-d]pyrimidin-7(6H)-yl)pyridazin-3(2H)-one ("Compound 1"); a solvent; and a polymer; wherein the polymer is dissolved in the solvent.

In one aspect, the invention features a method of manufacturing a spray-dried dispersion, comprising the step of spray-drying a composition of the invention.

In one aspect, the invention features spray-dried dispersions comprising 4-chloro-5-(4-(4-fluoro-2-(trifluoromethyl)phenoxy)-5,8-dihydropyrido[3,4-d]pyrimidin-7(6H)-yl)pyridazin-3(2H)-one; a solvent; and a polymer; wherein the polymer is dissolved in the solvent.

In one aspect, the invention features solid dosage forms comprising a spray-dried dispersion of the invention and one or more of a filler, a disintegrant, a lubricant, a glidant, and a stabilizer.

In one aspect, the invention features methods of manufacturing a solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of:

- a. blending a spray-dried dispersion disclosed herein with one or more of: a first filler, a first disintegrant, a first lubricant, a first glidant, and a first stabilizer to form a first solid mixture;
- b. roller compacting and milling the first solid mixture; and
- c. optionally blending the roller compacted and milled first solid mixture with one or more of a second filler, a second disintegrant, a second lubricant, a second glidant, and a second stabilizer to form a second solid mixture; and
- d. converting the first or the second solid mixture into the solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one.

In one aspect, the invention relates to methods of treating a disease or a nephropathy associated with a disease or condition, comprising administering to a subject in need thereof a solid dosage form of the invention.

In some embodiments, the kidney disease or the nephropathy associated with a disease or condition is Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, IgA nephropathy, IgG4 nephropathy, proteinuric kidney disease, microalbuminuria, macroalbuminuria kidney disease, transplant-related FSGS, transplant-related nephrotic syndrome, transplant-related proteinuria, nodular glomerulonephritis, NASR disease (proliferative glomerulonephritis with monoclonal IgG deposits), polycystic kidney disease, autosomal dominant polycystic kidney disease (ADPKD), or an nephropathy associated with any one of obesity, insulin resistance, Type II diabetes, prediabetes, metabolic syndrome, dyslipidemia, pulmonary arterial hypertension, cancer, cholestatic liver disease, non-alcoholic fatty liver disease (NAFLD), non-alcoholic steatohepatitis (NASH) or Fabry's disease).

In one aspect, the invention relates to methods of treating pain, anxiety, or depression, comprising administering to a subject in need thereof a solid dosage form of the invention.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a human.

The invention provides several advantages. The prophylactic and therapeutic methods described herein are effective in treating kidney disease, e.g., proteinuria, and have minimal, if any, side effects. Further, methods described herein are effective to identify compounds that treat or reduce risk of developing a kidney disease, anxiety, depression, or cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

BRIEF DESCRIPTION OF THE DRAWINGS

FIG. 3 shows an SEM Micrograph of crystalline Compound 1 Free Base Form H at 5000× magnification.

FIG. 13 shows a Certificate of Testing (CoT) for 25:75 Compound 1:HPMCAS-M SDI Certificate of Testing, Lot: D-17-078.

FIGS. 14A-14G show the retention times and relative peak heights of impurities after a spray solution of Compound 1 was held for various times at 40° C.

FIG. 15A shows assay and related substances of Compound 1 wet SDI when being held up to 15 days at room temperature.

FIG. 19. Tabletability, Compressibility, Compactability, and Disintegration profiles for 50 mg Compound 1 prototype tablets.

FIG. 22. Tabletability, Compressibility, Compactability, and Disintegration profiles for 20 and 100 mg Compound 1 Demonstration Batch tablets compared with prototype 50 mg Compound 1 tablet.

FIG. 30. Weight distributions of 20 and 100 mg Compound 1 Demonstration Batch tablets. Composite sample of 50 tablets was used.

FIG. 31 shows a 0.3125" SRC tablet tooling drawing according to some embodiments of the invention.

FIG. 33 shows a Certificate of Testing for a batch of 20 mg Compound 1 tablets.

FIG. 34 shows a Certificate of Testing for a batch of 100 mg Compound 1 tablets.

DETAILED DESCRIPTION

Figure 1A:
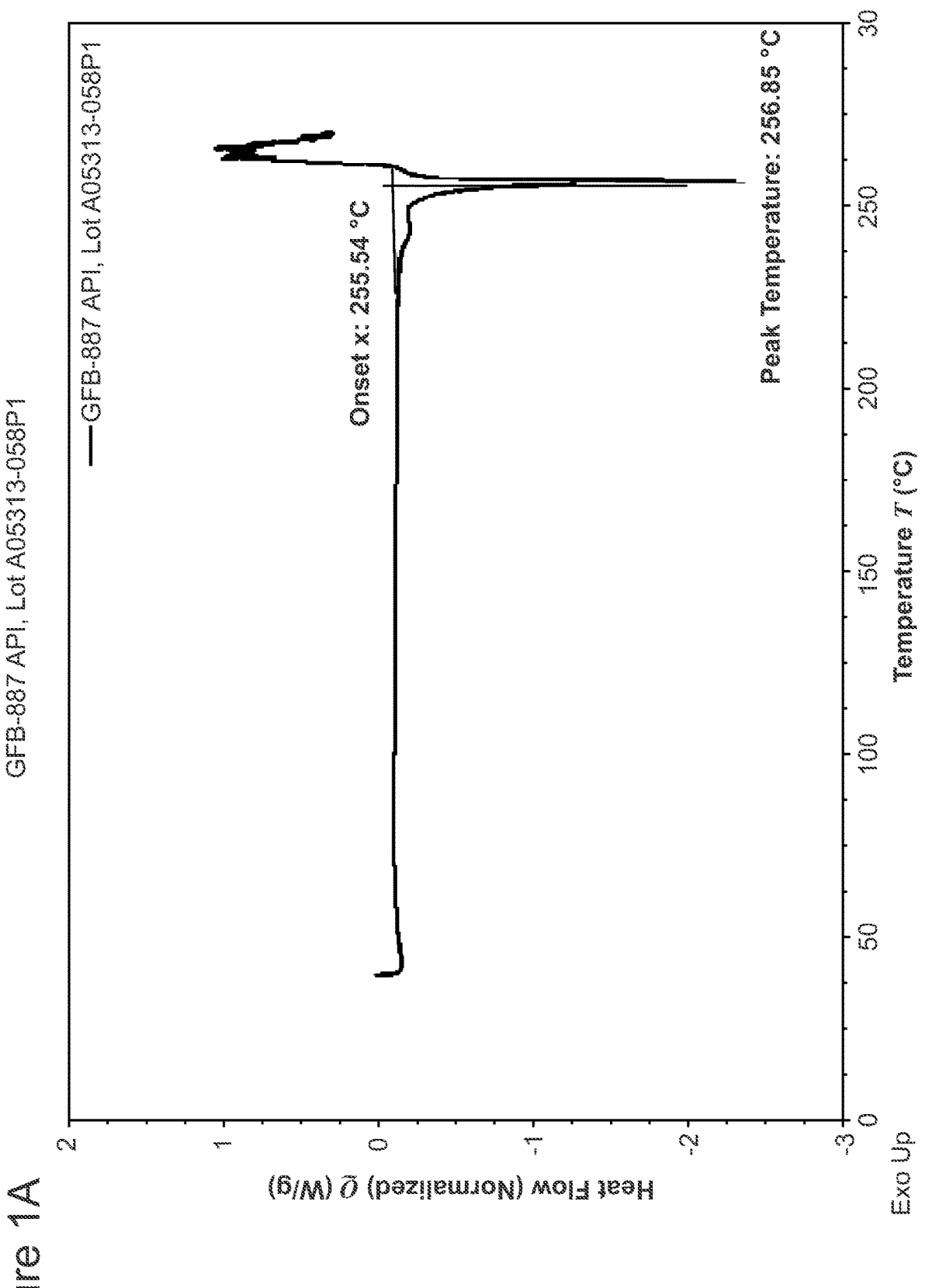
FIG. 1A shows a Thermogram for Crystalline Compound 1 Free Base Form H.

As used herein, a therapeutic that "prevents" or "reduces the risk of developing" a disease, disorder, or condition refers to a compound that, in a statistical sample, reduces the occurrence of the disease, disorder, or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Compounds of the Invention

In some embodiments, the compound is 4-chloro-5-(4-(4-fluoro-2-(trifluoromethyl)phenoxy)-5,8-dihydropyrido[3,4-d]pyrimidin-7(6H)-yl)pyridazin-3(2H)-one (a/k/a Compound 1), or a pharmaceutically acceptable salt thereof.

In some embodiments, the invention relates to a pharmaceutical composition, comprising the compound of the invention, or a pharmaceutically acceptable salt thereof; and a pharmaceutically acceptable carrier.

Pharmaceutical Compositions

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

"Pharmaceutically acceptable salt" is used herein to refer to an acid addition salt or a basic addition salt which is suitable for or compatible with the treatment of patients.

The term "pharmaceutically acceptable acid addition salt" as used herein means any non-toxic organic or inorganic salt of the disclosed compounds. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, bitartaric, citric, ascorbic, maleic, benzoic, phenylacetic, cinnamic, salicylic, and sulfosalicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds disclosed herein are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds disclosed herein for laboratory use, or for subsequent conversion to a pharmaceutically acceptable acid addition salt.

The term "pharmaceutically acceptable basic addition salt" as used herein means any non-toxic organic or inorganic base addition salt of any acid compounds disclosed herein. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) surfactants and co-surfactants, such as Vitamin E TPGS, Solutol® HS 15, and various polyethylene glycols; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896 (all incorporated by reference), as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules, gelatin capsules and HPMC capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, hydroxypropylcellulose gelatin, polyvinyl pyrrolidone, and starch; (3) humectants, such as glycerol; (4) disintegrating agents, such as agar-agar, calcium carbonate, potato or tapioca starch, alginic acid, certain silicates, microcrystalline cellulose, crospovidone, sodium carboxymethylcellulose and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as calcium stearate, magnesium stearate, solid polyethylene glycols, sodium lauryl sulfate, sodium stearyl fumarate, compritol and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, hydroxypropyl cellulose, povidone or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as taste masking coatings, enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, Vitamin E TPGS (D-α-tocopheryl polyethylene glycol succinate), Solutol® HS 15 (Macrogol (15)-hydroxystearate, Polyethylene glycol (15)-hydroxystearate, Polyoxyethylated 12-hydroxystearic acid), and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, microcrystalline cellulose, aluminum metahydroxide, bentonite, agar-agar, tragacanth, hydroxypropyl cellulose, sodium carboxymethylcullose, povidone and mixtures thereof. Suspensions may also contain surfactants and wetting agents, such as ethoxylated isostearyl alcohols, polyoxyethylene sorbitol and sorbitan esters.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, intraocular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, about 0.1 to about 99.5% (more preferably, about 0.5 to about 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subjects condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In certain embodiments, the active compound will be administered once daily.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In some embodiments, the pharmaceutical composition is a spray-dried dispersion.

In some embodiments, the invention is directed to a composition for manufacturing a spray-dried dispersion, the composition comprising 4-chloro-5-(4-(4-fluoro-2-(trifluoromethyl)phenoxy)-5,8-dihydropyrido[3,4-d]pyrimidin-7(6H)-yl)pyridazin-3(2H)-one; a solvent; and a polymer; wherein the polymer is dissolved in the solvent.

In some embodiments, the 4-chloro-5-(4-(4-fluoro-2-(trifluoromethyl)phenoxy)-5,8-dihydropyrido[3,4-d]pyrimidin-7(6H)-yl)pyridazin-3(2H)-one is in an amorphous form.

Polymers suitable for use in the compositions of the present invention include, but are not limited to, hypromellose acetate succinate, polyvinylpyrrolidone (PVP), Polyvinylpyrrolidone/vinyl acetate copolymers (PVP-VA, PVP-VA64), Eudragit®, hydroxypropylmethylcellulose (HPMC), Methocel, hypromellose phthalate, and soluplus. Eudragit® polymers are polymethacrylate-based copolymers. Suitable Eudragit® polymers include those for immediate release (e.g., Eudragit® E 10, Eudragit® E 12.5, Eudragit® E PO, Eudragit® E PO ReadyMix), delayed release (such as for small intestine delivery (e.g., Eudragit® L 30 D-55, Eudragit® L 100-55, Eudragit® FL 30 D-55, Eudragit® L 100, Eudragit® L 12.5; optionally in conjunction with PlasACRYL HTP20) or for colonic delivery (e.g., Eudragit® S 100, Eudragit® S 12.5 Eudragit® FS 30D, Eudragit® FS 100; optionally in conjunction with PlasACRYL T20)), sustained release (e.g., Eudragit® RL PO, Eudragit® RL 100, Eudragit® RL 30 D, Eudragit® RL 12.5, Eudragit® RS PO, Eudragit® RS 100, Eudragit® RS 30 D, Eudragit® RS 12.5, Eudragit® NM 30 D), and for solubility and bioavailability enhancement (e.g., Eudragit® E 100, Eudragit® E PO, Eudragit® E 12.5, Eudragit® FS 100, Eudragit® S 100, Eudragit® L 100, Eudragit® L 100-55, Eudragit® L 12.5); release profiles can be customized by combining Eudragit® polymers at different ratios, as will be known to those of skill in the art (see, e.g., healthcare.evonik.com/product/health-care/downloads/evonik-eudragit-brochure.pdf). Eudragit® L 100 is an anionic copolymer based on methacrylic acid and methyl methacrylic acid that dissolves at pH above 6. In some embodiments, the polymer is hypromellose acetate succinate, HPMCAS, PVP-VA64, or Eudragit®. In some embodiments, the polymer is hypromellose acetate succinate.

In some embodiments, the ratio of 4-chloro-5-(4-(4-fluoro-2-(trifluoromethyl)phenoxy)-5,8-dihydropyrido[3,4-d]pyrimidin-7(6H)-yl)pyridazin-3(2H)-one to hypromellose acetate succinate is between about 1:9 and about 2:1. In some embodiments, the ratio of 4-chloro-5-(4-(4-fluoro-2-(trifluoromethyl)phenoxy)-5,8-dihydropyrido[3,4-d]pyrimidin-7(6H)-yl)pyridazin-3(2H)-one to hypromellose acetate succinate is about 1:3.

Hypomellose acetate succinate (HPMCAS) products suitable for use with embodiments of the invention include, but are not limited to, AquaSolve™ products, such as those of grades L, M, and H:

| Grade | Acetyl Content (%) | Succinoyl Conent (%) | Methoxyl Content (%) | Hydroxypropoxy Content (%) |
|---|---|---|---|---|
| L | 5-9 | 14-18 | 20-24 | 5-9 |
| M | 7-12 | 7-15 | 21-25 | 5-9 |
| H | 10-14 | 4-8 | 22-26 | 6-10 |

In some embodiments, the hypromellose acetate succinate has an acetyl content of about 5-14%, a succinoyl content of about 4-18%, a methoxyl content of about 20-26%, and a hydroxypropoxy content of about 5-10%. In some embodiments, the hypromellose acetate succinate has an acetyl content of about 7-12%, a succinoyl content of about 7-15%, a methoxyl content of about 21-25%, and a hydroxypropoxy content of about 5-9%.

In some embodiments, the solvent is acetone, methyl ethlyketone, ethyl acetate, isopropyl alcohol, dioxane, acetonitrile, ethanol, water, methanol, dichloromethane, tetrahydrofuran, or a combination of any of them. In some embodiments, the solvent is a combination of methanol and dichloromethane. In some embodiments, the ratio of dichloromethane to methanol is about 30:70 to about 60:40. In some embodiments, the ratio of dichloromethane to methanol is about a 60:40.

In one aspect, the invention is directed to a method of manufacturing a spray-dried dispersion, comprising the step of spray-drying the composition of the invention.

In some embodiments, the temperature of a nozzle through which the composition is spray-dried is between about 20° C. and about 60° C. In some embodiments, the temperature of the nozzle is between about 35° C. and about 40° C.

In some embodiments, the step of spray drying is performed at an atomization pressure of between about 1.0 and about 10.0 bars. In some embodiments, the step of spray drying is performed at an atomization pressure of between about 2.0 and about 4.0 bars.

In one aspect, the invention relates to spray-dried dispersions comprising 4-chloro-5-(4-(4-fluoro-2-(trifluoromethyl)phenoxy)-5,8-dihydropyrido[3,4-d]pyrimidin-7(6H)-yl)pyridazin-3(2H)-one; a solvent; and a polymer; wherein the polymer is dissolved in the solvent.

In some embodiments, the 4-chloro-5-(4-(4-fluoro-2-(trifluoromethyl)phenoxy)-5,8-dihydropyrido[3,4-d]pyrimidin-7(6H)-yl)pyridazin-3(2H)-one is in an amorphous form.

In some embodiments, the polymer is hypromellose acetate succinate.

In some embodiments, the ratio of 4-chloro-5-(4-(4-fluoro-2-(trifluoromethyl)phenoxy)-5,8-dihydropyrido[3,4-d]pyrimidin-7(6H)-yl)pyridazin-3(2H)-one to hypromellose acetate succinate is between about 1:9 and about 2:1. In some embodiments, the ratio of 4-chloro-5-(4-(4-fluoro-2-

(trifluoromethyl)phenoxy)-5,8-dihydropyrido[3,4-d]pyrimi-din-7(6H)-yl)pyridazin-3(2H)-one to hypromellose acetate succinate is about 1:3.

In some embodiments, the hypromellose acetate succinate has an acetyl content of about 5-14%, a succinoyl content of about 4-18%, a methoxyl content of about 20-26%, and a hydroxypropoxy content of about 5-10%. In some embodiments, the hypromellose acetate succinate has an acetyl content of about 5-11%, a succinoyl content of about 10-18%, a methoxyl content of about 20-25%, and a hydroxypropoxy content of about 5-9%. In some embodiments, the hypromellose acetate succinate has an acetyl content of about 7-12%, a succinoyl content of about 7-15%, a methoxyl content of about 21-25%, and a hydroxypropoxy content of about 5-9%. Different grades of hypromellose acetate succinate are commercially available, e.g., Aqua-Solve™ hydroxypropylmehylcellulose acetate succinate gades L, M, and H from Ashland.

In some embodiments, the solvent is acetone, methyl ethlyketone, ethyl acetate, isopropyl alcohol, dioxane, acetonitrile, ethanol, water, methanol, dichloromethane, tetrahydrofuran, or a combination of any of them. In some embodiments, the solvent is a combination of methanol and dichloromethane. In some embodiments, the ratio of dichloromethane to methanol is about 30:70 to about 60:40. In some embodiments, the ratio of dichloromethane to methanol is about 60:40.

In one aspect, the invention relates to solid dosage forms comprising a spray-dried dispersion of the invention, and one or more of a filler, a disintegrant, a lubricant, a glidant, and a stabilizer.

In some embodiments, the filler comprises one or more of mannitol, lactose, or microcrystalline cellulose. In some embodiments, the filler comprises mannitol and microcrystalline cellulose. In some embodiments, the ratio of mannitol to microcrystalline cellulose is between about 1:3 and about 3:1. In some embodiments, the ratio of mannitol to microcrystalline cellulose is about 1:1.3, about 1:1.25, or about 1:1. In some embodiments, the ratio of mannitol to microcrystalline cellulose is between about 1:1.3 to about 1:1. In some embodiments, the ratio of mannitol to microcrystalline cellulose is about 1:1 to about 1:3. In some embodiments, the ratio of mannitol to microcrystalline cellulose is about 1:1 to about 1:1.3. In some embodiments, the ratio of mannitol to microcrystalline cellulose is about 1:1 or about 1:1.3. In some embodiments, the ratio of mannitol to microcrystalline cellulose is about 1:1, about 1:1.3, or about 1:3.

In some embodiments, the average particle size of the microcrystalline cellulose is between about 5 μm and about 80 μm. In some embodiments, the average particle size of the microcrystalline cellulose is between about 10 μm and about 50 μm.

In some embodiments, the disintegrant is croscarmellose sodium. In some embodiments, the croscarmellose sodium is present at between about 3% and about 15% w/w. In some embodiments, the croscarmellose sodium is present at about 6% w/w.

In some embodiments, the lubricant is stearyl fumarate sodium. In some embodiments, the stearyl fumarate sodium is present at between about 0.5 and about 5% w/w. In some embodiments, the stearyl fumarate sodium is present at about 1% w/w. In some embodiments, the stearyl fumarate sodium is present at about 0.95% w/w.

In some embodiments, the glidant is colloidal silicon dioxide. In some embodiments, the silicon dioxide is present at between about 0.1 to about 5% w/w. In some embodiments, the silicon dioxide is present at between about 1% w/w.

In some embodiments, the spray-dried dispersion is present at between about 3% to about 60% w/w. In some embodiments, the spray-dried dispersion is present at about 50% w/w. In some embodiments, the spray-dried dispersion is present at about 16.7% w/w. In some embodiments, the spray-dried dispersion is present at about 3.33% w/w.

In some embodiments, the 4-chloro-5-(4-(4-fluoro-2-(trifluoromethyl)phenoxy)-5,8-dihydropyrido[3,4-d]pyrimidin-7(6H)-yl)pyridazin-3(2H)-one is present at about 0.75%-15% w/w. For example, the compound may be present at about 0.75%, about 0.8%, about 0.85%, about 0.9%, about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% w/w.

In some embodiments, the solid dosage form consists essentially of:
a. 4-chloro-5-(4-(4-fluoro-2-(trifluoromethyl)phenoxy)-5,8-dihydropyrido[3,4-d]pyrimidin-7(6H)-yl) pyridazin-3(2H)-one;
b. hypromellose acetate succinate;
c. mannitol;
d. microcrystalline cellulose;
e. croscarmellose sodium;
f. stearyl fumarate sodium; and
g. colloidal silicon dioxide.
In some embodiments, the solid dosage form consists essentially of:
a. 0.75%-40.0% (w/w) 4-chloro-5-(4-(4-fluoro-2-(trifluoromethyl)phenoxy)-5,8-dihydropyrido[3,4-d]pyrimidin-7(6H)-yl)pyridazin-3(2H)-one;
b. 2.0%-54.0% (w/w) hypromellose acetate succinate;
c. 3.75%-42.3% (w/w) mannitol;
d. 3.75%%-50.0% (w/w) microcrystalline cellulose;
e. 3.0%-15% (w/w) croscarmellose sodium;
f. 0.5%-5.0% (w/w) stearyl fumarate sodium; and
g. 0.1%-5.0% (w/w) colloidal silicon dioxide,
wherein:
the ratio of 4-chloro-5-(4-(4-fluoro-2-(trifluoromethyl) phenoxy)-5,8-dihydropyrido[3,4-d]pyrimidin-7 (6H)-yl)pyridazin-3(2H)-one to hypromellose acetate succinate is between 1:9 and 2:1;
the sum of the amounts of 4-chloro-5-(4-(4-fluoro-2-(trifluoromethyl)phenoxy)-5,8-dihydropyrido[3,4-d] pyrimidin-7(6H)-yl)pyridazin-3(2H)-one and hypromellose acetate succinate is between 3% and 60% w/w of the solid dosage form;
the ratio of mannitol to microcrystalline cellulose is between 1:3 and 3:1; and
the sum of the amounts of mannitol and microcrystalline cellulose is between 15.0% and 90% w/w of the solid dosage form.
In some embodiments, the solid dosage form consists essentially of:
a. 20 mg of 4-chloro-5-(4-(4-fluoro-2-(trifluoromethyl) phenoxy)-5,8-dihydropyrido[3,4-d]pyrimidin-7(6H)-yl)pyridazin-3(2H)-one;
b. 60 mg of hypromellose acetate succinate;
c. 33.6 mg of mannitol;
d. 33.6 mg of microcrystalline cellulose;
e. 9.6 mg of croscarmellose sodium;

f. 1.6 mg stearyl fumarate sodium; and g. 1.6 mg colloidal silicon dioxide.

In some embodiments, the solid dosage form consists essentially of:

a. 100 mg of 4-chloro-5-(4-(4-fluoro-2-(trifluoromethyl) phenoxy)-5,8-dihydropyrido[3,4-d]pyrimidin-7(6H)-yl)pyridazin-3(2H)-one;

b. 300 mg of hypromellose acetate succinate;

c. 168 mg of mannitol;

d. 168 mg of microcrystalline cellulose;

e. 48 mg of croscarmellose sodium;

f. 8 mg stearyl fumarate sodium; and g. 8 mg colloidal silicon dioxide.

In some embodiments, the solid dosage form consists essentially of:

a. 5 mg of 4-chloro-5-(4-(4-fluoro-2-(trifluoromethyl) phenoxy)-5,8-dihydropyrido[3,4-d]pyrimidin-7(6H)-yl)pyridazin-3(2H)-one;

b. 15 mg of hypromellose acetate succinate;

c. 39.2 mg of mannitol;

d. 51.2 mg of microcrystalline cellulose;

e. 7.2 mg of croscarmellose sodium;

f. 1.1 mg of stearyl fumarate sodium; and g. 1.2 mg of colloidal silicon dioxide.

In some embodiments, the solid dosage form consists of:

a. 1 mg of 4-chloro-5-(4-(4-fluoro-2-(trifluoromethyl) phenoxy)-5,8-dihydropyrido[3,4-d]pyrimidin-7(6H)-yl)pyridazin-3(2H)-one;

b. 3 mg of hypromellose acetate succinate;

c. 47.2 mg of mannitol;

d. 59.2 mg of microcrystalline cellulose;

e. 7.2 mg of croscarmellose sodium;

f. 1.1 mg of stearyl fumarate sodium; and g. 1.2 mg of colloidal silicon dioxide.

In some embodiments, the solid dosage form is a tablet. In some embodiments, the solid dosage form is a capsule. In some embodiments, the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 1-200 mg.

In some embodiments, the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 5 mg.

In some embodiments, the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 20 mg.

In some embodiments, the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 100 mg.

In some embodiments, the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 1 mg.

In one aspect, the invention relates to a method of manufacturing a solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of:

a. blending a spray-dried dispersion of any one of claims 17-27 with one or more of: a first filler, a first disintegrant, a first lubricant, a first glidant, and a first stabilizer to form a first solid mixture;

b. roller compacting and milling the first solid mixture; and c. optionally blending the roller compacted and milled first solid mixture with one or more of a second filler, a second disintegrant, a second lubricant, a second glidant, and a second stabilizer to form a second solid mixture; and d. converting the first or the second solid mixture into the solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one.

In some embodiments, the first and second filler are selected from mannitol, microcrystalline cellulose of a combination thereof; the first and second disintegrant is croscarmellose sodium; the first and second lubricant is sodium stearyl fumarate; and the first and second glidant is silicon dioxide.

In some embodiments, in step c. the roller compacted and milled solid mixture is blended with a second filler, a second disintegrant, and a second lubricant.

In some embodiments, the solid dosage form is a tablet formed by compressing the first solid mixture or the second solid mixture. In some embodiments, the solid dosage form is a filled capsule formed by filling a capsule with the first solid mixture or the second solid mixture.

Methods of Treatment

Proteinuria

Proteinuria is a pathological condition wherein protein is present in the urine. Albuminuria is a type of proteinuria. Microalbuminuria occurs when the kidney leaks small amounts of albumin into the urine. In a properly functioning body, albumin is not normally present in urine because it is retained in the bloodstream by the kidneys. Microalbuminuria is diagnosed either from a 24-hour urine collection (20 to 200 µg/min) or, more commonly, from elevated concentrations (30 to 300 mg/L) on at least two occasions. Microalbuminuria can be a forerunner of diabetic nephropathy. An albumin level above these values is called macroalbuminuria. Subjects with certain conditions, e.g., diabetic nephropathy, can progress from microalbuminuria to macroalbuminuria and reach a nephrotic range (>3.5 g/24 hours) as kidney disease reaches advanced stages.

Causes of Proteinuria

Proteinuria can be associated with a number of conditions, including focal segmental glomerulosclerosis, IgA nephropathy, diabetic nephropathy, lupus nephritis, membranoproliferative glomerulonephritis, progressive (crescentic) glomerulonephritis, and membranous glomerulonephritis.

A. Focal Segmental Glomerulosclerosis (FSGS)

Focal Segmental Glomerulosclerosis (FSGS) is a disease that attacks the kidney's filtering system (glomeruli) causing serious scarring. FSGS is one of the many causes of a disease known as Nephrotic Syndrome, which occurs when protein in the blood leaks into the urine (proteinuria). Primary FSGS, when no underlying cause is found, usually presents as nephrotic syndrome. Secondary FSGS, when an underlying cause is identified, usually presents with kidney failure and proteinuria. FSGS can be genetic; there are currently several known genetic causes of the hereditary forms of FSGS.

Very few treatments are available for patients with FSGS. Many patients are treated with steroid regimens, most of which have very harsh side effects. Some patients have shown to respond positively to immunosuppressive drugs as well as blood pressure drugs which have shown to lower the level of protein in the urine. To date, there is no commonly accepted effective treatment or cure and there are no FDA approved drugs to treat FSGS. Therefore, more effective methods to reduce or inhibit proteinuria are desirable.

B. IgA Nephropathy

IgA nephropathy (also known as IgA nephritis, IgAN, Berger's disease, and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus. There are other diseases associated with glomerular IgA deposits, the most common being Henoch-Schonlein purpura (HSP), which is considered by many to be a systemic form of IgA nephropathy. Henoch-Schonlein purpura presents with a characteristic purpuric skin rash, arthritis, and abdominal pain and occurs more commonly in young adults (16-35 yrs old). HSP is associated with a more benign prognosis than IgA nephropathy. In IgA nephropathy there is a slow progression to chronic renal failure in 25-30% of cases during a period of 20 years.

C. Diabetic Nephropathy

Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and diffuse glomerulosclerosis. It is due to long-standing diabetes mellitus and is a prime cause for dialysis. The earliest detectable change in the course of diabetic nephropathy is a thickening in the glomerulus. At this stage, the kidney may start allowing more serum albumin than normal in the urine. As diabetic nephropathy progresses, increasing numbers of glomeruli are destroyed by nodular glomerulosclerosis and the amount of albumin excreted in the urine increases.

D. Lupus Nephritis

Lupus nephritis is a kidney disorder that is a complication of systemic lupus erythematosus. Lupus nephritis occurs when antibodies and complement build up in the kidneys, causing inflammation. It often causes proteinuria and may progress rapidly to renal failure. Nitrogen waste products build up in the bloodstream. Systemic lupus erythematosus causes various disorders of the internal structures of the kidney, including interstitial nephritis. Lupus nephritis affects approximately 3 out of 10,000 people.

E. Membranoproliferative Glomerulonephritis I/II/III

Membranoproliferative glomerulonephritis is a type of glomerulonephritis caused by deposits in the kidney glomerular mesangium and basement membrane thickening, activating complement and damaging the glomeruli. There are three types of membranoproliferative glomerulonephritis. Type I is caused by immune complexes depositing in the kidney and is believed to be associated with the classical complement pathway. Type II is similar to Type I, however, it is believed to be associated with the alternative complement pathway. Type III is very rare and it is characterized by a mixture of subepithelial deposits and the typical pathological findings of Type I disease.

There are two major types of MPGN, which are based upon immunofluorescence microscopy: immune complex-mediated and complement-mediated. Hypocomplement-emia is common in all types of MPGN. In immune complex-mediated MPGN, complement activation occurs via the classic pathway and is typically manifested by a normal or mildly decreased serum C3 concentration and a low serum C4 concentration. In complement-mediated MPGN, there are usually low serum C3 and normal C4 levels due to activation of the alternate pathway. However, complement-mediated MPGN is not excluded by a normal serum C3 concentration, and it is not unusual to find a normal C3 concentration in adults with dense deposit disease (DDD) or C3 glomerulonephritis (C3GN).

C3 glomerulonephritis (C3GN) shows a glomerulonephritis on light microscopy (LM), bright C3 staining and the absence of C1q, C4 and immunoglobulins (Ig) on immunofluorescence microscopy (IF), and mesangial and/or subendothelial electron dense deposits on electron microscopy (EM). Occasional intramembranous and subepithelial deposits are also frequently present. The term 'C3 glomerulopathy' is often used to include C3GN and Dense Deposit Disease (DDD), both of which result from dysregulation of the alternative pathway (AP) of complement. C3GN and DDD may be difficult to distinguish from each other on LM and IF studies. However, EM shows mesangial and/or subendothelial, intramembranous and subepithelial deposits in C3GN, while dense osmiophilic deposits are present along the glomerular basement membranes (GBM) and in the mesangium in DDD. Both C3GN and DDD are distinguished from immune-complex mediated glomerulonephritis by the lack of immunoglobulin staining on IF. (Sethi et al., Kidney Int. (2012) 82(4):465-473).

F. Progressive (Crescentic) Glomerulonephritis

Progressive (crescentic) glomerulonephritis (PG) is a syndrome of the kidney that, if left untreated, rapidly progresses into acute renal failure and death within months. In 50% of cases, PG is associated with an underlying disease such as Goodpasture's syndrome, systemic lupus erythematosus, or Wegener granulomatosis; the remaining cases are idiopathic. Regardless of the underlying cause, PG involves severe injury to the kidney's glomeruli, with many of the glomeruli containing characteristic crescent-shaped scars. Patients with PG have hematuria, proteinuria, and occasionally, hypertension and edema. The clinical picture is consistent with nephritic syndrome, although the degree of proteinuria may occasionally exceed 3 g/24 hours, a range associated with nephrotic syndrome. Untreated disease may progress to decreased urinary volume (oliguria), which is associated with poor kidney function.

G. Membranous Glomerdonephritis

Membranous glomerulonephritis (MGN) is a slowly progressive disease of the kidney affecting mostly patients between ages of 30 and 50 years, usually Caucasian. It can develop into nephrotic syndrome. MGN is caused by circulating immune complex. Current research indicates that the majority of the immune complexes are formed via binding of antibodies to antigens in situ to the glomerular basement membrane. The said antigens may be endogenous to the basement membrane, or deposited from systemic circulation.

H. Alport Syndrome

Alport syndrome is a genetic disorder affecting around 1 in 5,000-10,000 children, characterized by glomerulonephritis, end-stage kidney disease, and hearing loss. Alport syndrome can also affect the eyes, though the changes do not usually affect sight, except when changes to the lens occur in later life. Blood in urine is universal. Proteinuria is a feature as kidney disease progresses.

I. Hypertensive Kidney Disease

Hypertensive kidney disease (Hypertensive nephrosclerosis (HN or HNS) or hypertensive nephropathy (HN)) is a medical condition referring to damage to the kidney due to chronic high blood pressure. HN can be divided into two types: benign and malignant. Benign nephrosclerosis is common in individuals over the age of 60 while malignant nephrosclerosis is uncommon and affects 1-5% of individuals with high blood pressure, that have diastolic blood pressure passing 130 mm Hg. Signs and symptoms of chronic kidney disease, including loss of appetite, nausea, vomiting, itching, sleepiness or confusion, weight loss, and an unpleasant taste in the mouth, may develop. Chronic high blood pressure causes damages to kidney tissue; this includes the small blood vessels, glomeruli, kidney tubules and interstitial tissues. The tissue hardens and thickens which is known as nephrosclerosis. The narrowing of the blood vessels means less blood is going to the tissue and so less oxygen is reaching the tissue resulting in tissue death (ischemia).

J. Nephrotic Syndrome

Nephrotic syndrome is a collection of symptoms due to kidney damage. This includes protein in the urine, low blood albumin levels, high blood lipids, and significant swelling. Other symptoms may include weight gain, feeling tired, and foamy urine. Complications may include blood clots, infections, and high blood pressure. Causes include a number of kidney diseases such as focal segmental glomerulosclerosis, membranous nephropathy, and minimal change disease. It may also occur as a complication of diabetes or lupus. The underlying mechanism typically involves damage to the glomeruli of the kidney. Diagnosis is typically based on urine testing and sometimes a kidney biopsy. It differs from nephritic syndrome in that there are no red blood cells in the urine. Nephrotic syndrome is characterized by large amounts of proteinuria (>3.5 g per 1.73 m2 body surface area per day, or >40 mg per square meter body surface area per hour in children), hypoalbuminemia (<2.5 g/dl), hyperlipidaemia, and edema that begins in the face. Lipiduria (lipids in urine) can also occur, but is not essential for the diagnosis of nephrotic syndrome. Hyponatremia also occur with a low fractional sodium excretion. Genetic forms of nephrotic syndrome are typically resistant to steroid and other immunosuppressive treatment. Goals of therapy are to control urinary protein loss and swelling, provide good nutrition to allow the child to grow, and prevent complications. Early and aggressive treatment are used to control the disorder.

K. Minimal Change Disease

Minimal change disease (also known as MCD, minimal change glomerulopathy, and nil disease, among others) is a disease affecting the kidneys which causes a nephrotic syndrome. The clinical signs of minimal change disease are proteinuria (abnormal excretion of proteins, mainly albumin, into the urine), edema (swelling of soft tissues as a consequence of water retention), weight gain, and hypoalbuminaemia (low serum albumin). These signs are referred to collectively as nephrotic syndrome. The first clinical sign of minimal change disease is usually edema with an associated increase in weight. The swelling may be mild but patients can present with edema in the lower half of the body, periorbital edema, swelling in the scrotal/labial area and anasarca in more severe cases. In older adults, patients may also present with acute kidney injury (20-25% of affected adults) and high blood pressure. Due to the disease process, patients with minimal change disease are also at risk of blood clots and infections.

L. Membranous Nephropathy

Membranous nephropathy refers to the deposition of immune complexes on the glomerular basement membrane (GBM) with GBM thickening. The cause is usually unknown (idiopathic), although secondary causes include drugs, infections, autoimmune disorders, and cancer. Manifestations include insidious onset of edema and heavy proteinuria with benign urinary sediment, normal renal function, and normal or elevated blood pressure. Membranous nephropathy is diagnosed by renal biopsy. Spontaneous remission is common. Treatment of patients at high risk of progression is usually with corticosteroids and cyclophosphamide or chlorambucil.

M. Postinfectious Glomerulonephritis

Acute proliferative glomerulonephritis is a disorder of the glomeruli (glomerulonephritis), or small blood vessels in the kidneys. It is a common complication of bacterial infections, typically skin infection by *Streptococcus* bacteria types 12, 4 and 1 (impetigo) but also after streptococcal pharyngitis, for which it is also known as postinfectious or poststreptococcal glomerulonephritis. It can be a risk factor for future albuminuria. In adults, the signs and symptoms of infection may still be present at the time when the kidney problems develop, and the terms infection-related glomerulonephritis or bacterial infection-related glomerulonephritis are also used. Acute glomerulonephritis resulted in 19,000 deaths in 2013 down from 24,000 deaths in 1990 worldwide. Acute proliferative glomerulonephritis (post-streptococcal glomerulonephritisis) is caused by an infection with *streptococcus* bacteria, usually three weeks after infection, usually of the pharynx or the skin, given the time required to raise antibodies and complement proteins. The infection causes blood vessels in the kidneys to develop inflammation, this hampers the renal organs ability to filter urine.[citation needed] Acute proliferative glomerulonephritis most commonly occurs in children.

N. Thin Basement Membrane Disease

Thin basement membrane disease (TBMD, also known as benign familial hematuria and thin basement membrane nephropathy or TBMN) is, along with IgA nephropathy, the most common cause of hematuria without other symptoms. The only abnormal finding in this disease is a thinning of the basement membrane of the glomeruli in the kidneys. Its importance lies in the fact that it has a benign prognosis, with patients maintaining a normal kidney function throughout their lives. Most patients with thin basement membrane disease are incidentally discovered to have microscopic hematuria on urinalysis. The blood pressure, kidney function, and the urinary protein excretion are usually normal. Mild proteinuria (less than 1.5 g/day) and hypertension are seen in a small minority of patients. Frank hematuria and loin pain should prompt a search for another cause, such as kidney stones or loin pain-hematuria syndrome. Also, there are no systemic manifestations, so presence of hearing impairment or visual impairment should prompt a search for hereditary nephritis such as Alport syndrome. Some individuals with TBMD are thought to be carriers for genes that cause Alport syndrome.

O. Mesangial Proliferative Glomerulonephritis

Mesangial proliferative glomerulonephritis is a form of glomerulonephritis associated primarily with the mesangium. There is some evidence that interleukin-10 may inhibit it in an animal model.[2] It is classified as type II lupus nephritis by the World Health Organization (WHO). Mesangial cells in the renal glomerulus use endocytosis to take up and degrade circulating immunoglobulin. This normal process stimulates mesangial cell proliferation and matrix deposition. Therefore, during times of elevated circulating immunoglobulin (i.e. lupus and IgA nephropathy) one would expect to see an increased number of mesangial cells and matrix in the glomerulus. This is characteristic of nephritic syndromes.

P. Amyloidosis (Primary)

Amyloidosis is a group of diseases in which abnormal protein, known as amyloid fibrils, builds up in tissue.[4] Symptoms depend on the type and are often variable.[2]

They may include diarrhea, weight loss, feeling tired, enlargement of the tongue, bleeding, numbness, feeling faint with standing, swelling of the legs, or enlargement of the spleen.[2] There are about 30 different types of amyloidosis, each due to a specific protein misfolding.[5] Some are genetic while others are acquired.[3] They are grouped into localized and systemic forms.[2] The four most common types of systemic disease are light chain (AL), inflammation (AA), dialysis (Ap2M), and hereditary and old age (ATTR). Primary amyloidosis refers to amyloidosis in which no associated clinical condition is identified.

Q. c1q Nephropathy

C1q nephropathy is a rare glomerular disease with characteristic mesangial C1q deposition noted on immunofluorescence microscopy. It is histologically defined and poorly understood. Light microscopic features are heterogeneous and comprise minimal change disease (MCD), focal segmental glomerulosclerosis (FSGS), and proliferative glomerulonephritis. Clinical presentation is also diverse, and ranges from asymptomatic hematuria or proteinuria to frank nephritic or nephrotic syndrome in both children and adults. Hypertension and renal insufficiency at the time of diagnosis are common findings. Optimal treatment is not clear and is usually guided by the underlying light microscopic lesion. Corticosteroids are the mainstay of treatment, with immunosuppressive agents reserved for steroid resistant cases. The presence of nephrotic syndrome and FSGS appear to predict adverse outcomes as opposed to favorable outcomes in those with MCD. (Devasahayam, et al., "C1q Nephropathy: The Unique Underrecognized Pathological Entity," Analytical Cellular Pathology, vol. 2015, Article ID 490413, 5 pages, 2015. doi.org/10.1155/2015/490413.)

R. Anti-GBM Disease

Anti-glomerular basement membrane (GBM) disease, also known as Goodpasture's disease, is a rare condition that causes inflammation of the small blood vessels in the kidneys and lungs. The antiglomerular basement membrane (GBM) antibodies primarily attack the kidneys and lungs, although, generalized symptoms like malaise, weight loss, fatigue, fever, and chills are also common, as are joint aches and pains. 60 to 80% of those with the condition experience both lung and kidney involvement; 20-40% have kidney involvement alone, and less than 10% have lung involvement alone. Lung symptoms usually antedate kidney symptoms and usually include: coughing up blood, chest pain (in less than 50% of cases overall), cough, and shortness of breath. Kidney symptoms usually include blood in the urine, protein in the urine, unexplained swelling of limbs or face, high amounts of urea in the blood, and high blood pressure. GPS causes the abnormal production of anti-GBM antibodies, by the plasma cells of the blood. The anti-GBM antibodies attack the alveoli and glomeruli basement membranes. These antibodies bind their reactive epitopes to the basement membranes and activate the complement cascade, leading to the death of tagged cells. T cells are also implicated. It is generally considered a type II hypersensitivity reaction.

Measurement of Urine Protein Levels

Protein levels in urine can be measured using methods known in the art. Until recently, an accurate protein measurement required a 24-hour urine collection. In a 24-hour collection, the patient urinates into a container, which is kept refrigerated between trips to the bathroom. The patient is instructed to begin collecting urine after the first trip to the bathroom in the morning. Every drop of urine for the rest of the day is to be collected in the container. The next morning, the patient adds the first urination after waking and the collection is complete.

More recently, researchers have found that a single urine sample can provide the needed information. In the newer technique, the amount of albumin in the urine sample is compared with the amount of creatinine, a waste product of normal muscle breakdown. The measurement is called a urine albumin-to-creatinine ratio (UACR). A urine sample containing more than 30 milligrams of albumin for each gram of creatinine (30 mg/g) is a warning that there may be a problem. If the laboratory test exceeds 30 mg/g, another UACR test should be performed 1 to 2 weeks later. If the second test also shows high levels of protein, the person has persistent proteinuria, a sign of declining kidney function, and should have additional tests to evaluate kidney function.

Tests that measure the amount of creatinine in the blood will also show whether a subject's kidneys are removing wastes efficiently. Too much creatinine in the blood is a sign that a person has kidney damage. A physician can use the creatinine measurement to estimate how efficiently the kidneys are filtering the blood. This calculation is called the estimated glomerular filtration rate, or eGFR. Chronic kidney disease is present when the eGFR is less than 60 milliliters per minute (mL/min).

The transient receptor potential channel 5 (TRPC5) is a calcium-permeable nonspecific cation channel predominantly expressed in the brain where it can form heterotetrameric complexes with TRPC1 and TRPC4 channel subunits. TRPC5 is also expressed in the kidney, more specifically in podocytes where it is involved in the regulation of the podocyte actin cytoskeleton.

Accordingly, in certain embodiments, the invention provides methods for treating, or the reducing risk of developing, a kidney disease or a nephropathy associated with a disease or condition, comprising administering to a subject in need thereof a solid dosage form of the invention. In some embodiments, the kidney disease or the nephropathy associated with a disease or condition is Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, IgA nephropathy, IgG4 nephropathy, proteinuric kidney disease, microalbuminuria, macroalbuminuria kidney disease, transplant-related FSGS, transplant-related nephrotic syndrome, transplant-related proteinuria, nodular glomerulonephritis, NASR disease (proliferative glomerulonephritis with monoclonal IgG deposits), polycystic kidney disease, autosomal dominant polycystic kidney disease (ADPKD), or an nephropathy associated with any one of obesity, insulin resistance, Type II diabetes, prediabetes, metabolic syndrome, dyslipidemia, pulmonary arterial hypertension, cancer, cholestatic liver disease, non-alcoholic fatty liver disease (NAFLD), non-alcoholic steatohepatitis (NASH) or Fabry's disease).

In some embodiments, the kidney disease or the nephropathy associated with a disease or condition is Focal Segmental Glomerulosclerosis (FSGS), Diabetic nephropathy, Alport syndrome, hypertensive kidney disease, obesity-related nephropathy, nephrotic syndrome, steroid-resistant nephrotic syndrome, minimal change disease, membranous nephropathy, membranoproliferative glomerulonephritis (MPGN), Lupus nephritis, postinfectious glomerulonephritis, thin basement membrane disease, mesangial proliferative glomerulonephritis, amyloidosis (primary), c1q nephropathy, anti-GBM disease, C3 glomerulonephritis, hypertensive nephrosclerosis, IgA nephropathy, IgG4 nephropathy, dyslipidemia-associated nephropathy, nodular glomerulonephritis, NASR disease (proliferative glomerulonephritis with monoclonal IgG deposits), polycystic kidney disease, or kidney complications due to Fabry's disease.

In some embodiments, the kidney disease is hypertensive nephropathy, a nephropathy associated with metabolic syndrome, a nephropathy associated with obesity, a nephropathy associated with dyslipidemia, diabetic nephropathy, nephrotic syndrome, FSGS, or minimal change disease. In some embodiments, the kidney disease is diabetic nephropathy, FSGS, or minimal change disease.

In one aspect, the invention relates to a method of treating pain, anxiety, or depression, comprising administering to a subject in need thereof a solid dosage form of the invention. Subjects to be Treated In one aspect of the invention, a subject is selected on the basis that they have, or are at risk of developing, a kidney disease, pulmonary arterial hypertension, anxiety, depression, cancer, diabetic retinopathy, or pain. In another aspect, a subject is selected on the basis that they have, or are at risk of developing, kidney disease, anxiety, depression, cancer, or diabetic retinopathy. In another aspect of the invention, a subject is selected on the basis that they have, or are at risk of developing, pain, neuropathic pain, visceral pain, transplant-related FSGS, transplant-related nephrotic syndrome, transplant-related proteinuria, cholestatic liver disease, polycystic kidney disease, autosomal dominant polycystic kidney disease (ADPKD), obesity, insulin resistance, Type II diabetes, prediabetes, metabolic syndrome, non-alcoholic fatty liver disease (NAFLD), or non-alcoholic steatohepatitis (NASH).

Subjects that have, or are at risk of developing, proteinuria include those with diabetes, hypertension, or certain family backgrounds. In the United States, diabetes is the leading cause of end-stage renal disease (ESRD). In both type 1 and type 2 diabetes, albumin in the urine is one of the first signs of deteriorating kidney function. As kidney function declines, the amount of albumin in the urine increases. Another risk factor for developing proteinuria is hypertension. Proteinuria in a person with high blood pressure is an indicator of declining kidney function. If the hypertension is not controlled, the person can progress to full kidney failure. African Americans are more likely than Caucasians to have high blood pressure and to develop kidney problems from it, even when their blood pressure is only mildly elevated. Other groups at risk for proteinuria are American Indians, Hispanics/Latinos, Pacific Islander Americans, older adults, and overweight subjects.

In one aspect of the invention, a subject is selected on the basis that they have, or are at risk of developing proteinuria. A subject that has, or is at risk of developing, proteinuria is one having one or more symptoms of the condition. Symptoms of proteinuria are known to those of skill in the art and include, without limitation, large amounts of protein in the urine, which may cause it to look foamy in the toilet. Loss of large amounts of protein may result in edema, where swelling in the hands, feet, abdomen, or face may occur. These are signs of large protein loss and indicate that kidney disease has progressed. Laboratory testing is the only way to find out whether protein is in a subject's urine before extensive kidney damage occurs.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a mammal. In some embodiments, the subject is a human.

EXAMPLES

The invention is further described in the following examples, which do not limit the scope of the invention described in the claims.

All ratios and percentages are presented on a weight basis unless otherwise specified.

Example 1. Excipients and Equipment

Potential excipients for spray dried solid dispersions and tablet development manufacturing were of compendial or USP grade and selected based on prior experience at Patheon. A full list of excipients and equipment utilized for this body of work can be found in Table 1. Throughout this report, percent compositions of solutions or solid dispersions are described on a weight:weight basis, unless otherwise specified.

TABLE 1

| Materials and Equipment | | | |
|---|---|---|---|
| Material and Equipment | Trade Name or Model | Abbreviation or Equipment ID | Manufacturer |
| Methylene Chloride | Methylene Chloride | DCM | Fisher |
| Methanol | Methanol | MeOH | Fisher |
| Hypromellose acetate succinate MG grade | AQOAT-MG | HPMCAS-M | Shin Etsu |
| Hypromellose acetate succinate LG grade | AQOAT-LG | HPMCAS-L | Shin Etsu |
| Microcrystalline Cellulose PH-105 | Avicel PH-105 | Avicel PH-105 | DuPont |
| Microcrystalline Cellulose PH-200 | Avicel PH-200 | Avicel PH-200 | DuPont |
| Mannitol | Pearlitol 100SD | Pearlitol 100SD | Roquette |
| Lactose (spray dried), Monohydrate | Fast Flow #316 | Fast Flow #316 | Foremost |
| Croscarmellose Sodium | Ac-Di-Sol | Ac-Di-Sol | DuPont |
| Crospovidone | Kollidon CL | Kollidon CL | BASF |
| Fumed Silicon Dioxide | Cab-O-Sil | Cab-O-Sil | Cabot |
| Sodium Stearyl Fumarate | PRUV | SSF | JRS Pharma |
| Spray Dryer | B-290 | RD-038 | Buchi |
| Condenser | B-295 | RD-039 | Buchi |
| Tray Dryer | 12083308 | RD-044 | VWR |
| Blender | Turbula | RD-069 | Turbula |
| Bin Blender | Mini Mix Lab | RD-054 | COS.MEC |
| 50 L Bin | 50 L | RD-054-04 | COS.MEC |
| 30 L Bin | 30 L | RD-054-03 | COS.MEC |
| Roller Compactor | Vector TFC-220 | PE-057 | Freund Vector |
| Mill | 197 Comil | PE-147 | Quadro |
| Single Station Tablet Press | NPRD10A | RD-066 | Natoli |
| Rotary Tablet Press | Riva-Piccola | RD-036 | Piccola |
| Tablet Tooling (0.3125" SRC) | NA | HOB: 91300 | Natoli |

TABLE 1-continued

| Materials and Equipment | | | |
|---|---|---|---|
| Material and Equipment | Trade Name or Model | Abbreviation or Equipment ID | Manufacturer |
| Tablet Tooling (0.3543" × 0.6890" Modified Oval) | NA | HOB: 81993 | Natoli |
| Tapped Density Tester | SVM | RD-053 | ERWEKA |
| Hardness Tester | TBH-125 | RD-056 | ERWEKA |
| Disintegration Apparatus | VK-100 | RD-032 | Varian |
| Friability Tester | FT-2 | RD-031 | Pharmatron |
| Sieve Shaker | RX-29-E | RD-035 | WS Tyler |
| Envelope Density Tester | GeoPyc 1360 | RD-057 | Micromeritics |

Example 2. Differential Scanning Calorimetry (DSC)

MDSC was performed using a TA Instruments Discovery DSC2500 differential scanning calorimeter equipped with a TA instruments Refrigerated Cooling System 90. MDSC was used to measure thermodynamic events and character-istics of Compound 1 API and subsequent SDIs. Events observed include the glass transition temperature ($T_g$), cold crystallization ($T_c$, defined as a crystallization event at a temperature lower than the melt temperature) and melting temperature ($T_m$). SDI samples were placed in non-hermetic aluminum pans and heated at a constant rate of 2.0° C./min over a 0-200° C. temperature range. The system was purged by nitrogen flow at 50 mL/min to ensure inert atmosphere through the course of measurement. Amorphous API was obtained by successfully heating Compound 1 above the melting point to 258° C. and rapidly quenching using liquid $N_2$. The resulting amorphous API was analyzed by modu-lated DSC up to 265° C. A summary of MDSC analysis parameters can be found in Table 2.

TABLE 2

| MDSC Analysis Parameters | |
|---|---|
| Parameter | Value |
| Instrument | TA Discovery DSC2500, RCS 90 |
| Sample Pans | Tzero Al, Non-hermetic |
| Temp. Range | 5-200° C. (5-265° C. for API) |
| Heating Rate | 2° C./min |
| Scanning Mode | Modulated |
| Modulation Frequency | 60 s |
| Modulation Amplitude | 1° C. |

Example 3. X-Ray Powder Diffraction (XRPD)

XRPD was performed using a Rigaku Miniflex 6G or Bruker D2 Phaser X-ray diffractometer to evaluate the crystallinity of spray dried materials. Amorphous materials give an "amorphous halo" diffraction pattern, absent of discrete peaks that would be found in a crystalline material. The samples were irradiated with monochromatized Cu Kα radiation and analyzed between 5° and 40° with a continu-ous scanning mode. Samples were rotated during analysis to minimize preferred orientation effects. A summary of XRPD analysis parameters can be found in Table 3 and Table 4 and are different for each instrument in order to achieve similar diffraction patterns.

TABLE 3

| XRPD Analysis Parameters (Rigaku) | |
|---|---|
| Parameter | Value |
| Instrument | Rigaku Miniflex 6G |
| Radiation Source | Cu-Kα (1.5406 Å), Line Focus 0.4 mm × 12 mm |
| Scan Type | Coupled 2θ/θ |
| Scan Range | 5°-40° |
| Step Increment | 0.005° |
| Ramp Rate | 0.9°/min |
| Voltage | 40 kV |
| Current | 15 mA |
| Rotation | 30 r/min |
| Holder | Zero-Background Cup |
| Divergent Slit Width | 0.625 mm |

TABLE 4

| XRPD Analysis Parameters (Bruker) | |
|---|---|
| Parameter | Value |
| Instrument | Bruker D2 Phaser |
| Radiation Source | Cu—Kα (1.5406 A), Line Focus 0.4 mm × 12 mm |
| Scan Type | Coupled 20/0 |
| Scan Range | 5°-40° |
| Step Increment | 0.02° |
| Step Time | 1 s |
| PSD Opening | 5.01° |
| Voltage | 30 kV |
| Current | 10 mA |
| Rotation | 15 r/min |
| Holder | Zero-Background Cup |
| Slit Width | 1.0 mm |
| Knife-Edge Width | 1.0 mm |

Example 4. Particle Morphology by Scanning Electron Microscope (SEM)

SEM samples were prepared by dispersing powder onto an adhesive carbon-coated sample stub a coating with a thin conductive layer of gold-palladium using a Cressington 108 Auto. Samples were analyzed using a FEI Quanta 200 SEM fitted with an Everhart-Thornley (secondary electron) detec-tor, operating in high vacuum mode. Micrographs at various magnifications were captured for qualitative particle mor-phology analysis. Experimental parameters including spot size, working distance, and acceleration voltage were varied from sample to sample to obtain the best imaging conditions, and are documented in the caption of each SEM micrograph.

Example 5. Particle Size Distribution (PSD) by Light Diffraction

The particle size of SDI samples were determined by laser diffraction using a Mastersizer 3000 with an Aero S unit (Malvern Instruments). About 100 mg samples were added to the standard venture disperser with a hopper gap of 1.5 mm and then fed into the dispersion system. The feed rate of 40% was adjusted to keep the laser obscuration level at 0.1-15%. Compressed air at 2 bar was used to transport and suspend the sample particles through the optical cell. A measurement time of 10 seconds was used, and background measurements were made using air for 10 seconds. $D_{V10}$, $D_{V50}$ and $D_{V90}$ diameters were used to characterize the particle size distribution of powders. For instance, the $D_{V50}$ diameter is the diameter at which 50% of a sample's volume is comprised of equal to or smaller particles.

Example 6. Water Content Measurement by Coulometric Karl Fischer (KF) Titration SDI samples were collected after secondary drying and analyzed for water content by a Metrohm 831 Karl Fischer Coulometric Titrator with a Metrohm 874 oven processor. About 100 mg samples were sealed in 6 mL crimp vials followed by measurement of water content with the following parameters: Reagent Hydranal Coulomat AG-Oven, Oven temperature 150° C. and sample extraction time 300 seconds.

Example 7. Dynamic Vapor Sorption (DVS)

The level of water adsorption of crystalline Compound 1 was investigated using dynamic vapor sorption (DVS). Samples were exposed to varying humidity levels from 10-90% in 10% increments, with desorption to 20% relative humidity (RH). Precise weight measurements taken at 2 min intervals indicate the wt % uptake of $H_2O$ as a function of % RH. DVS analysis parameters are displayed below in Table 5.

TABLE 5

DVS Analysis Parameters

| | Parameter | Value |
|---|---|---|
| Drying: | Drying: | On |
| | Temperature: | 60° C. |
| | Equil Criterion: | 0.001 wt % in 5 min |
| | Max Drying Time: | 60 min |
| Adsorption/ | Temperature: | 25° C. |
| Desoprtion | Bypass Sample: | Wait for RH |
| | Equil Criterion: | 0.005 wt % in 5 min |
| | Max Equil Criterion: | 120 min |
| Rel | RH Start: | 10% |
| Humidity | RH End: | 90% |
| | RH Step: | 10% |
| | Des Cutoff: | 20% |
| | Data Logging Interval: | 2 min or 0.001 wt % |

Example 8. Assay and Related Substances Analysis by HPLC

Assay and related substances of SDI samples were evaluated using an experimental HPLC method (Table 6). The HPLC method utilized was based on API manufacturing HPLC method for Compound 1. The method demonstrated a linear response, selectivity, and separation of previously seen impurities.

Example 9. Residual Solvent

The residual solvent content of the SDIs were measured by GC headspace analysis (GC-HS) after secondary drying. Measurements were made using an HP 6890 series GC equipped with an Agilent 7697A headspace sampler. A 30 m×0.32 mm×1.8µ capillary column with 6% cyanopropylphenyl 94% dimethylpolysiloxane GC column was used for the testing. GC samples were prepared by dissolving ~100 mg sample in 4 mL dimethyl sulfoxide (DMSO). A standard GC-HS method (DM-123) was used, without additional verification/validation activities for the drug product at this stage.

Example 10. In Vitro Dissolution Performance

In-vitro drug dissolution performance for each SDI is evaluated by Patheon's two stage 'gastric transfer' non-sink dissolution test (Table 8), which simulates pH and bile salt concentrations for both gastric and intestinal exposure in a simple to perform assay. Pre-weighed SDI powder is briefly suspended in media (e.g. by 10 sec vortex mixing with 4.0 mL media) and transferred to a pre-heated (37° C.) volume of 50 mL of 0.1N $HCl_{(aq)}$ (simulated gastric fluid or SGF, pH~1.0, without pepsin or bile salts), in a USP Type 2 mini-vessel (100 mL total vessel volume) while stirring (paddles) at 100 rpm. After 30 minutes of gastric pH exposure, an equal volume of PBS buffered, 2× concentrated fasted-state simulated intestinal fluid (FaSSIF) is added to the SGF, resulting in a final pH of 6.8 in FaSSIF (100 mM PBS containing 2.24 mg/mL SIF powder (original) (Biorelevant Inc.) in a total volume of 100 mL. Aliquiots (1.0 mL) of dissolution media are taken at selected time-points before and after the simulated gastric transfer, spun-down (13000 rpm) to pellet out undissolved solids, and the supernatant sampled and further diluted in an appropriate diluent to determine API total drug concentration (e.g. free and colloidal/polymer-bound drug in solution) utilizing a suitable HPLC method. Additional centrifugation and filtration was performed using 10K molecular weight cutoff filters to remove polymer bound aggregates and colloids. The resulting filtrate of free drug consists of drug in solution and micelles. The volume of FaSSIF added is adjusted to account for the sampling volume removed prior to gastric transfer (typically 4×1.0 mL). Initial Compound 1 API measurements and SDI dissolution samples were determined utilizing HPLC.

TABLE 6

Non-Sink Dissolution Test Parameters

| Parameter | Value |
|---|---|
| Apparatus | USP Type 2 (100 mL) |
| Gastric Media | 0.1N HCl (aq) |
| Intestinal Media | FaSSIF |
| Temperature | 37 ± 0.5° C. |
| Paddle Speed | 100 RPM |
| Dose | 1.0 → 0.5 mg Compound 1/mL |

Example 11. Sink Dissolution

Compound 1 Tablets, 20 mg & 100 mg were analyzed using USP <711> Apparatus 2 in 50 mM Phosphate Buffer, pH=6.8 w/ 2% SLS (w/v). Samples are filtered at the time of collection and analyzed by reversed-phase High Performance Liquid Chromatography (HPLC) with ultraviolet (UV) detection (Table 7).

TABLE 7

Summary of Dissolution Parameters

| Parameter | Value |
|---|---|
| Apparatus | USP < 711> Apparatus 2 (paddles and 1 L vessels) |
| Dissolution Medium | 50 mM Phosphate buffer, pH = 6.8 w/2% SLS |
| Medium Temperature | 37° C. (±0.5° C.) |
| Medium Volume | 900 mL |
| Stir Rate | 100 rpm (0-60 minutes), 200 rpm (60-75 minutes) |
| Sampling Volume | 10 mL |
| Sample Filtration | 10 µm polyethylene cannula filters, change filter after each timepoint, Centrifuge or PTFE Filter Prior to HPLC analysis |

TABLE 7-continued

Summary of Dissolution Parameters

| Parameter | Value |
|---|---|
| Sampling Time Points | 5, 15, 30, 45, 60 and 75 minutes |
| Sample Stability | 3 days at room temperature |

Example 12. Preparation of Dissolution Media

Simulated Gastric Fluid (SGF): Determine the volume of SGF needed for all dissolution samples. Based on this volume, dilute 1.0N HCl 10× with $H_2O$ in a suitable Class A graduated cylinder or volumetric flask. Mix well, test approximate pH using pH paper. The observed pH should be 1.0-1.1.

PBS buffer (200 mM): Determine the volume of buffer needed for all dissolution samples. Based on this volume, weigh 200 mMol/L NaCl and 200 mMol/L $Na_2HPO_4$ and transfer into an appropriately-sized vessel. To this vessel, add the appropriate volume of $H_2O$. Sonicate the solution until all salts are fully dissolved. If necessary, adjust with phosphoric acid or 1.0N NaOH to pH $8.9\pm0.1$.

FaSSIF Media (4.48 mg/mL): To PBS media above, add 4.48 mg SIF powder per mL of 200 mM PBS. Mix well, stirring with a magnetic stir bar until all SIF is in solution. Let stand two hours at RT before use, and then pre-heat to 37° C. for the dissolution test. If FaSSIF will not be used the day it is prepared, store in refrigerator (2-8° C.) for up to 4 days. Remove from refrigerator at least two hours before use, ensuring that the solution reaches 37° C. prior to use.

50 mM Phosphate buffer, pH=6.8 w/2% SLS (w/v): Combine 6 L of water and 41.4 g sodium phosphate monobasic monohydrate, Adjust to pH=6.8. Add 120 g of sodium lauryl sulfate and stir to dissolve.

Example 13. Disintegration

Disintegration was evaluated per USP <701> "Disintegration" utilizing a Varian VK-100 disintegration apparatus. The apparatus consists of a 1000 mL low-form beaker and basket-rack assembly with six open-ended transparent tubes. The beaker contained 750 mL of RO water and was maintained at a temperature of 37° C. (±2° C.). The basket was fully submerged at a frequency of 29-32 cycles per minute and tablet disintegration time was recorded when the last visible tablet materials passed through the basket.

Example 14. Tablet Friability

Friability was determined by USP <1216> utilizing a Pharmatron FT 2 friability tester. A drum rotation speed of 25 rpms was used at a total rotation time of 4 minutes. Acceptable loss on friability per USP method is ≤1.0 weight percent.

Example 15. Tablet Hardness and Tensile Strength

Tablet breaking force was tested per USP <1217>"Tablet Breaking Force" utilizing a Natoli Hardness Tester (S/N 1403029). Tablet thickness and weight were measured prior to assessing the tablet break force as it is a destructive process. Tablets were placed in the automated breaking apparatus and tablet breaking force was measured in kilogram-force/kilopond (kp). Tablet tensile strength for standard round concave (SRC) and oblong tablets were calculated (in MPa) based on the following equations:

$$\text{Tablet Tensile Strength (SRC)} = \frac{10P}{\pi D^2 \left(2.8 - \frac{t}{D} - 0.126\frac{t}{W} + 3.15\frac{W}{D} + 0.01\right)} \qquad \text{Equation 2}$$

$$\text{Tablet Tensile Strength (Oblong)} = \frac{2}{3}\left(\frac{10P}{\pi D^2 \left(2.84\frac{t}{D} - 0.126\frac{t}{W} + 3.15\frac{W}{D} + 0.01\right)}\right) \qquad \text{Equation 3}$$

where P=fracture load, D=tablet width, t=tablet thickness, W=band thickness (K. G. Pitt and M. G. Heasley. "Determination of the tensile strength of elongated tablets." *Powder Technology*, vol. 238 (2013) pp. 169-175.)

Example 16. Particle Size Distribution by Sieve Analysis

Particle size distribution was determined by an analytical sieving method similar to USP <786>. A RO-TAP RX-29-E sieve shaker (W. S. Tyler) was utilized to evaluate material. Screens utilized and operating parameters can be found below in Table 8:

TABLE 8

Equipment and Parameters for Particle Size
Distribution Analysis via Analytical Sieving Method

| Parameter | Value |
|---|---|
| Equipment Manufacture | W.S. Tyler |
| Sieve Shaker Model | RO-TAP RX-29-E |
| Shaker Mode | Coarse |
| Operating Time | 5 min |
| Screen #1 | 20 mesh (841 μm) |
| Screen #2 | 30 mesh (595 μm) |
| Screen #3 | 40 mesh (420 μm) |
| Screen #4 | 60 mesh (250 μm) |
| Screen #5 | 120 mesh (125 μm) |
| Screen #6 | 200 mesh (74 μm) |

Example 17. Compounds Analysis and Property Assessment

Figure 1B:
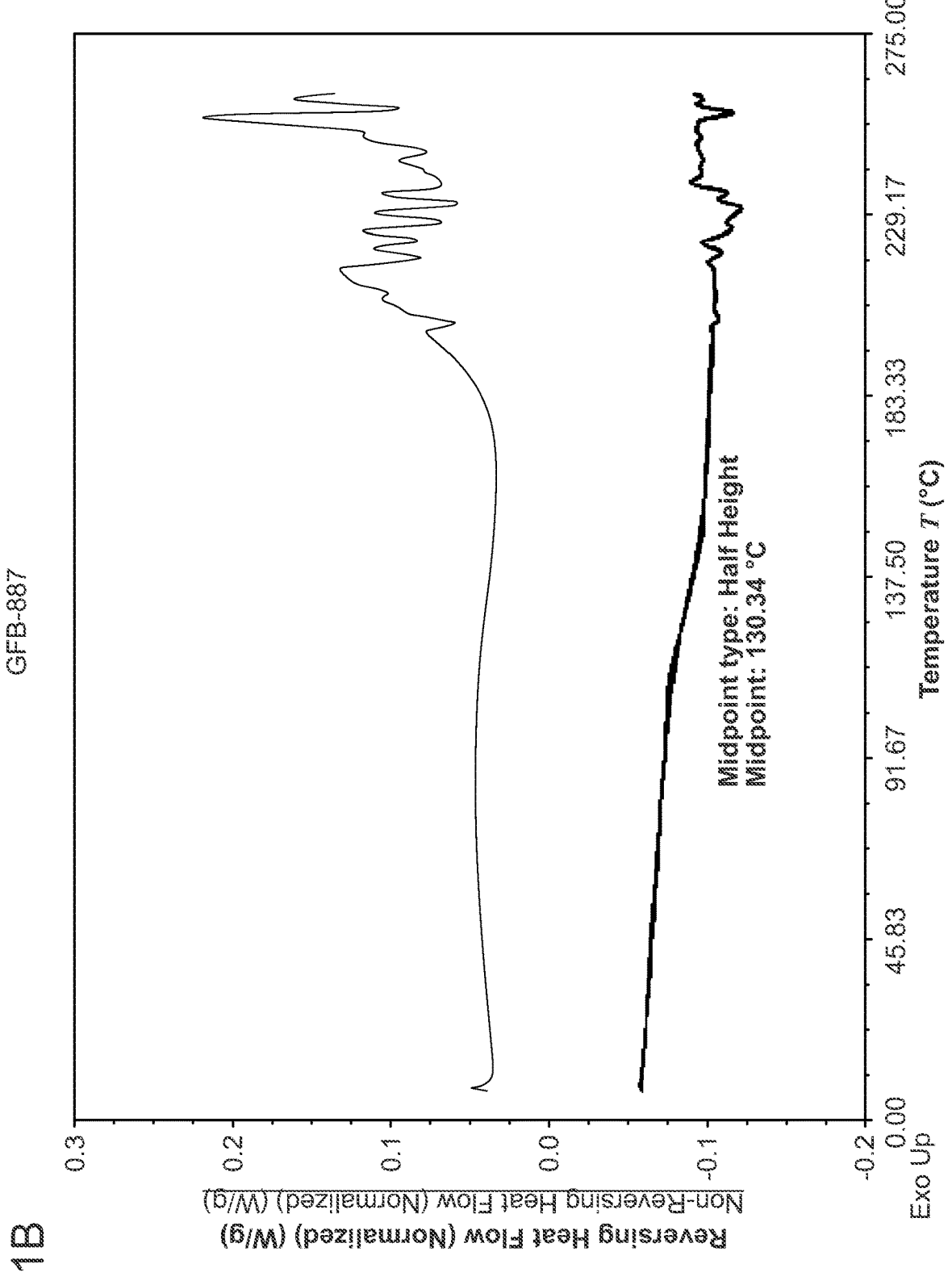
FIG. 1B shows a thermogram for Amorphous Compound 1.

Thermal properties including melting temperature $(T_m)$, glass transition temperature $(T_g)$ and crystallization temperature $(T_c)$ of Compound 1 crystalline Form H (anhydrous/solvate free) were measured by MDSC. The $T_m$ of Compound 1 was initially captured performing a standard heating rate ramp of 10° C./min, and a melt-decomposition was observed with an endothermic melting peak at 257° C. The $T_g$ was measured via a melt-quench technique, heating Compound 1 past its melting temperature and rapidly cooled in liquid nitrogen to trap the molten material in an amorphous state. The resulting sample was analyzed by MDSC and a $T_g$ of 130° C. was observed (FIGS. 1A-B/Table 9) with no observed crystallization peaks or clear melting events in the subsequent amorphous ramp up to 275° C. A $T_m/T_g$ ratio of 1.32 was obtained indicating moderate physical stability. The $T_m/T_g$ ratio coupled with stable amorphous API (up to 200° C.) indicates a possibility of higher drug loading amorphous dispersions with acceptable physical stability.

TABLE 9

| Summary of Thermal Properties of Crystalline Compound 1 Free Base Form H | | | |
| --- | --- | --- | --- |
| Material | Lot | $T_g$ | $T_m$ |
| Compound 1 | A05313-058P1 | 130° C. | 257° C. |

Figure 2:
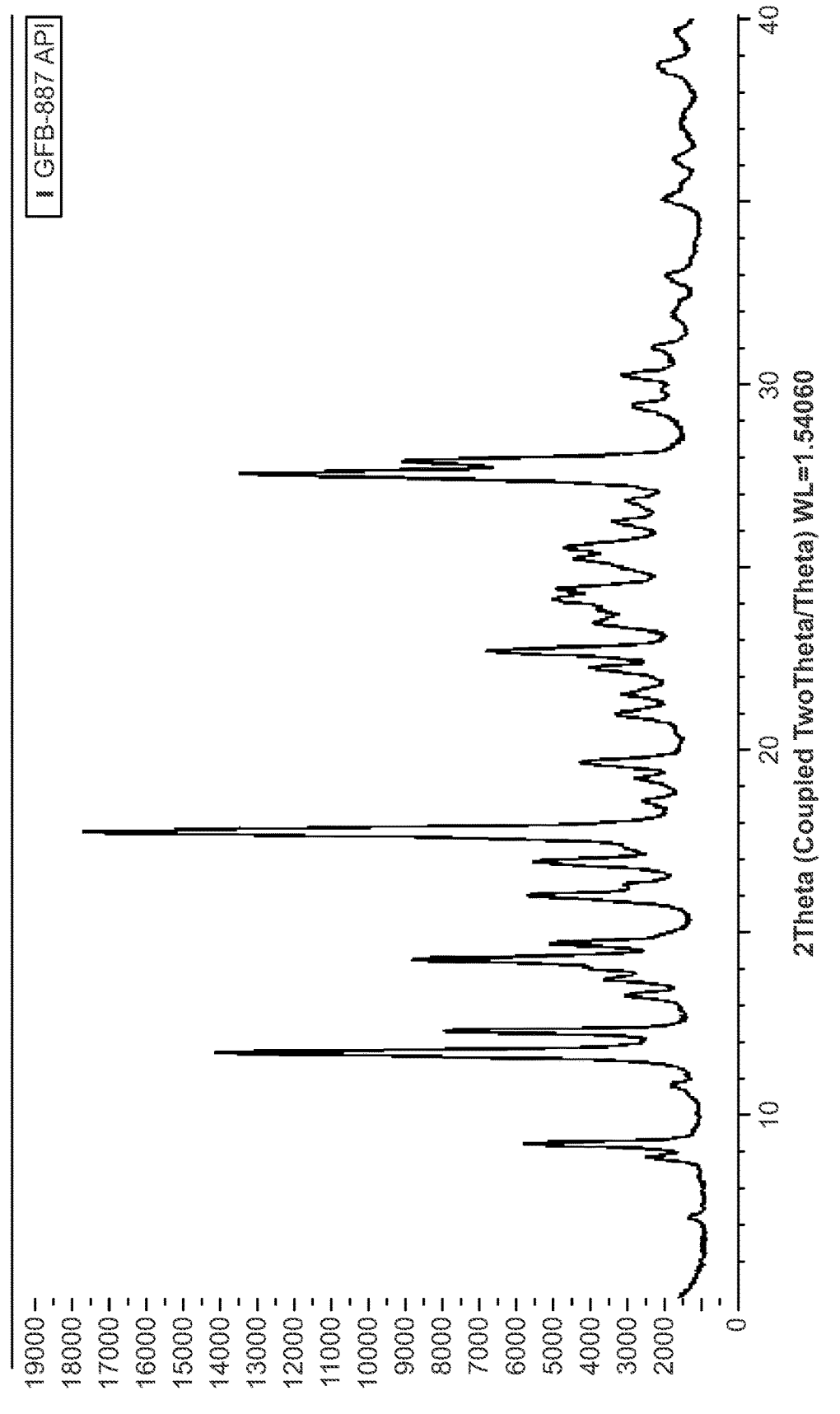
FIG. 2 shows an XRPD Diffractogram of Crystalline Compound 1 Free Base Form H.

A diffraction pattern of crystalline Compound 1 form was performed using XRPD (FIG. 2). The diffraction pattern of the bulk API indicates a crystalline material, consistent with thermal analysis.

Surface morphology of the bulk API particles were characterized using scanning electron microscopy. The SEM image in FIG. 3 shows images of the Compound 1 API at 500×, 1500×, and 5000× magnification. API morphology consists of agglomerates of smaller API particles of varying crystal morphology.

Organic solubility of Compound 1 was determined visually in common spray drying solvents (Table 10) and Compound 1 lot AC5313-058P1 was utilized.

TABLE 10

| Solubility of Bulk Compound 1 Crystalline Form Form H in Organic Solvents Determined Visually | | |
| --- | --- | --- |
| Solvent System | Compound 1 Visual Solubility (wt .%) | Observation |
| Methanol | >1.0 | Insoluble |
| Methlyene Chloride (DCM) | >1.0 | Insoluble |
| Acetone | >1.0 | Insoluble |
| Tetrahydrofuran (THF) | >1.0 | Insoluble |
| Methyl Ethyl Ketone (MEK) | >1.0 | Insoluble |
| 95:5 Acetone:Water | >1.0 | Insoluble |
| 90:10 DCM:Methanol | 1.0-1.5 | Soluble[1] |
| 80:20 DCM:Methanol | 1.0-1.5 | Soluble[1] |
| 50:50 DCM:Methanol | >1.0 | Insoluble |
| 60:40 DCM:Methanol | 2.0-3.0 | Soluble[1] |

[1]Clear solution obtained when heated to 40° C..

3.0% Compound 1 dissolved into 60:40 DCM:Methanol when heated to 40° C. after ~2 hours. When removed from heat API crashes out after 5 minutes. Solution (% w/w) was then prepared at 2.0% Compound 1 and heated to 40° C. where solids dissolved immediately. The 2.0% solution was then removed from heat where API appeared to crash out after ~2 hours. Heated (40° C.) 60:40 DCM:Methanol was nominated as the lead solvent system at a maximum active loading of 2.0% Compound 1 in solution.

Example 18. Focused Screening of Solid Dispersion Polymers: Spray Dried Formulation Manufacturing Feasibility dispersions were manufactured using Compound 1 lot AC5313-058P1. Five Compound 1 SDI formulations were chosen for feasibility screening. These formulations were selected based on previous data provided by Goldfinch Bio where acceptable PK results were obtained using 25:75 Compound 1:HPMCAS-L SDI. The selected feasibility dispersions were designed to determine maximum Compound 1 loading and evaluate the performance of HPMCAS-M based dispersions. A summary of spray drying parameters (Table 11) and recovered SDI dry yields (Table 12) can be found below. Spray solutions appeared amber and transparent after API addition.

TABLE 11

| Summary of spray drying parameters used for Compound 1 feasibility. | |
| --- | --- |
| Parameter | Value |
| Spray Dryer | Buchi B290 |
| Cyclone | High Efficiency |
| Solvent System | 60:40 DCM:Methanol |
| Solution Temperature | 40° C. |
| Batch Size, Active | 9 g Compound 1 |
| Solution Composition | 3-7% |
| Atomization Pressure | 25 psi |
| Solution Feed Rate | 15 mL/min |
| Inlet Temperature | 77-105° C. |
| Outlet Temperature | 45° C. |
| Secondary Drying | 24 hr at 40° C. |

TABLE 12

| Summary of spray drying formulation yields. | | |
| --- | --- | --- |
| Formulations | Lot# | Dry Yield (%) |
| 25:75 Compound 1:HPMCAS-M | G8-854-4 | 80 |
| 50:50 Compound 1:HPMCAS-M | G8-854-5 | 66 |
| 66:34 Compound 1:HPMCAS-M | G8-854-6 | 76 |
| 25:75 Compound 1:HPMCAS-L | G8-854-7 | 60 |
| 50:50 Compound 1:HPMCAS-L | G8-854-8 | 66 |

Example 19. Focused Screening of Solid Dispersion Polymers: Spray Dried Formulation Characterization Initial SDI formulations were characterized by powder X-ray diffraction (XRPD), scanning electron microscopy (SEM), modulated differential scanning calorimetry (MSDC), headspace gas chromatography (GC-HS), and in vitro non-sink dissolution tests.

A secondary tray drying process was used to remove residual solvent after spray drying. In this operation, the "wet" SDI was heated to 40° C. and stored in a convection tray oven for 24 hours. Gas chromatograph (GC) headspace analysis was used to measure the residual solvents remaining in the Compound 1 SDI material after secondary drying. The residual solvent in all formulations was below the DCM (600 ppm) and MeOH (3000 ppm) limit set forth by the International Conference on Harmonization (ICH). Table 13 shows the residual solvent results for the feasibility formulations.

TABLE 13

| Summary of GC headspace results for Compound 1 SDIs after secondary drying. | | |
| --- | --- | --- |
| Formulations | Lot# | Residual Solvent (ppm) |
| 25:75 Compound 1:HPMCAS-M | G8-854-4 | MeOH: <400; DCM: Not Detected |
| 50:50 Compound 1:HPMCAS-M | G8-854-5 | MeOH: <400; DCM: Not Detected |
| 66:34 Compound 1:HPMCAS-M | G8-854-6 | MeOH: <400; DCM: Not Detected |

TABLE 13-continued

Summary of GC headspace results for Compound 1
SDIs after secondary drying.

| Formulations | Lot# | Residual Solvent (ppm) |
|---|---|---|
| 25:75 Compound 1:HPMCAS-L | G8-854-7 | MeOH: <400;<br>DCM: Not Detected |
| 50:50 Compound 1:HPMCAS-L | G8-854-8 | MeOH: <400;<br>DCM: Not Detected |

Figure 4:
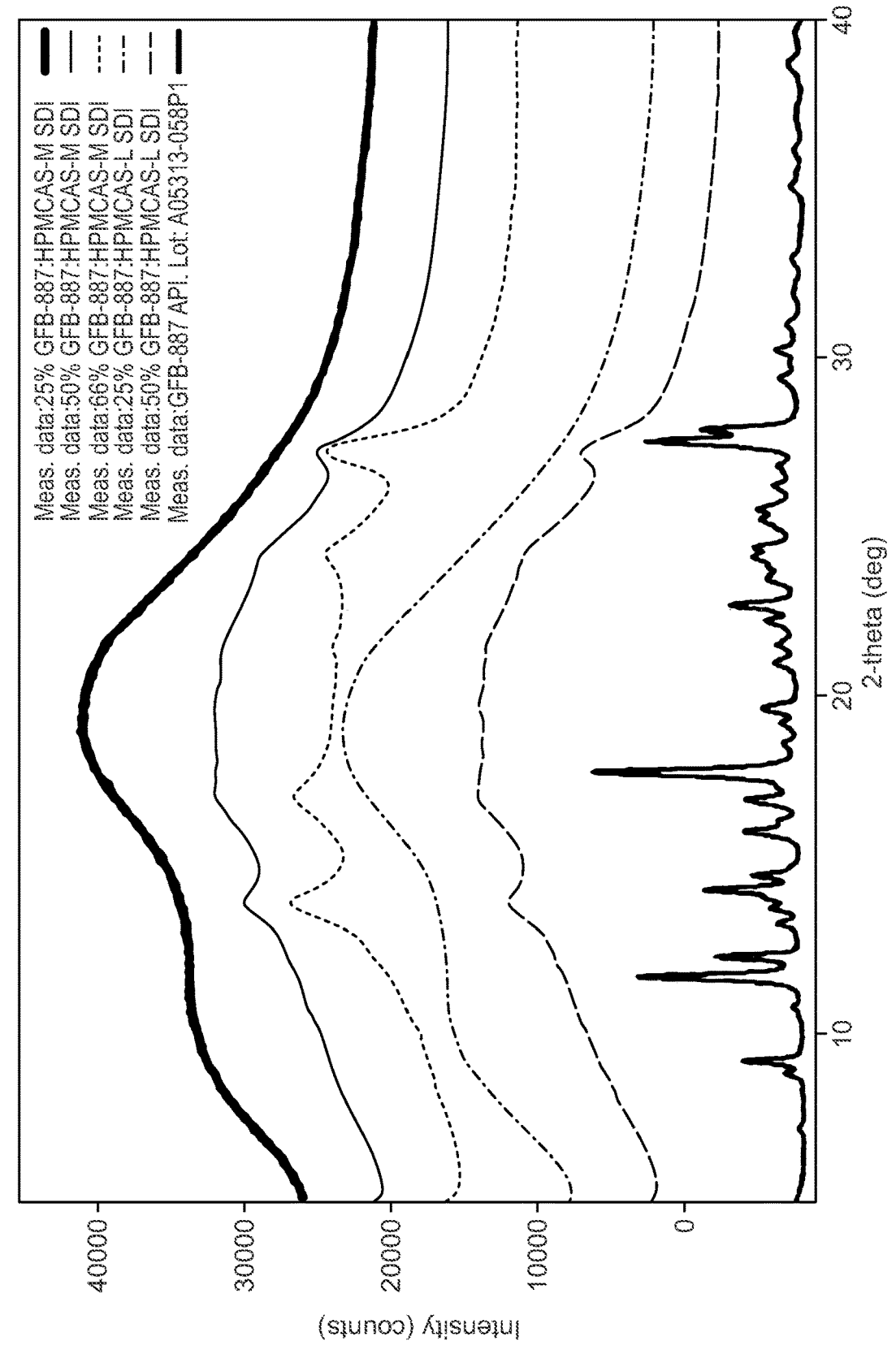
FIG. 4 shows XRPD diffractograms of Compound 1 feasibility dispersions.

Initial characterization by XRPD indicates that 50 and 66% Compound 1 SDIs showed crystalline peaks and all 25% SDIs were amorphous (FIG. 4).

Figure 5A:
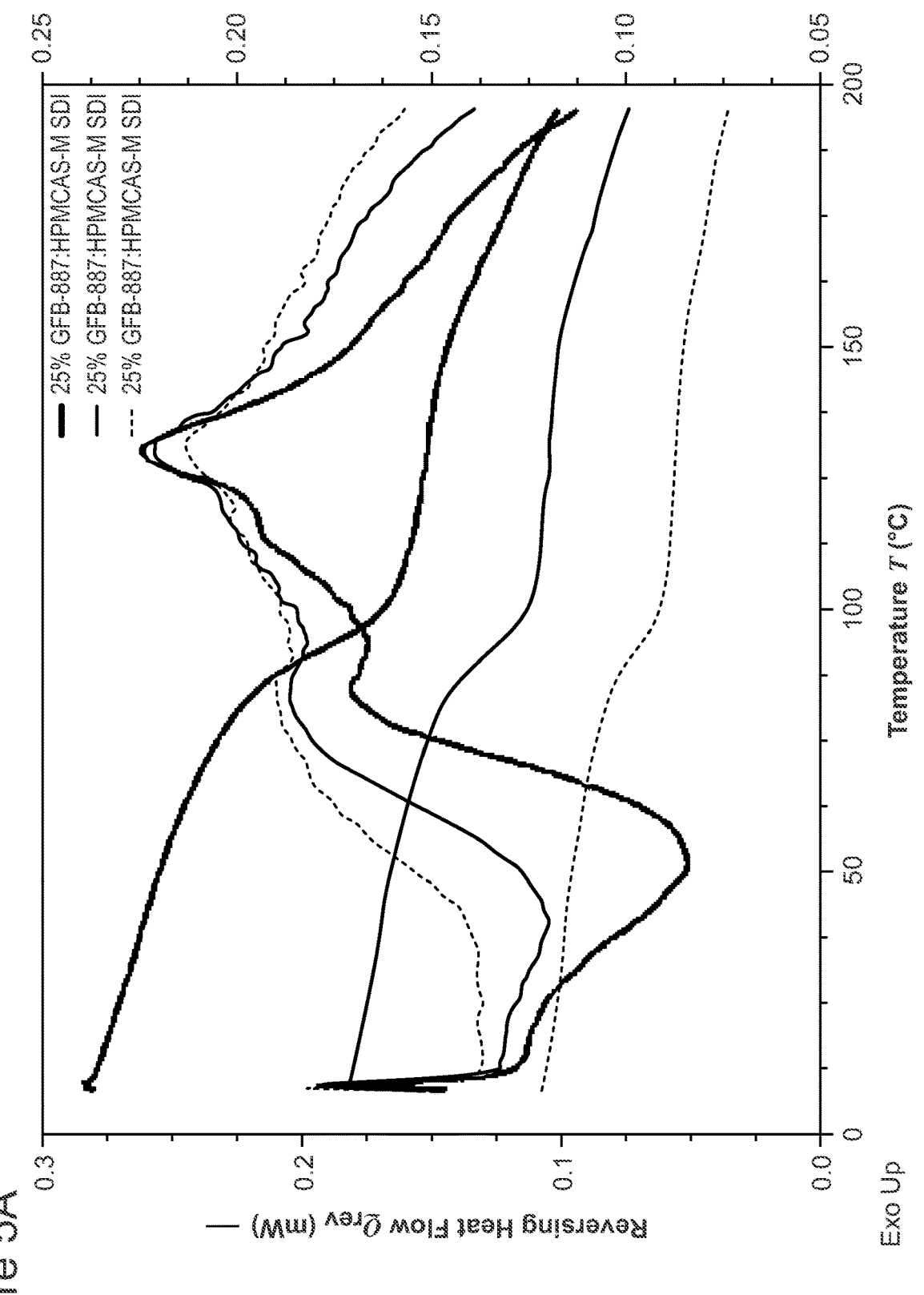
FIG. 5A is a MDSC thermogram showing the Tg of amorphous 25% Compound 1 dispersions in HPMCAS-M.
Figure 5B:
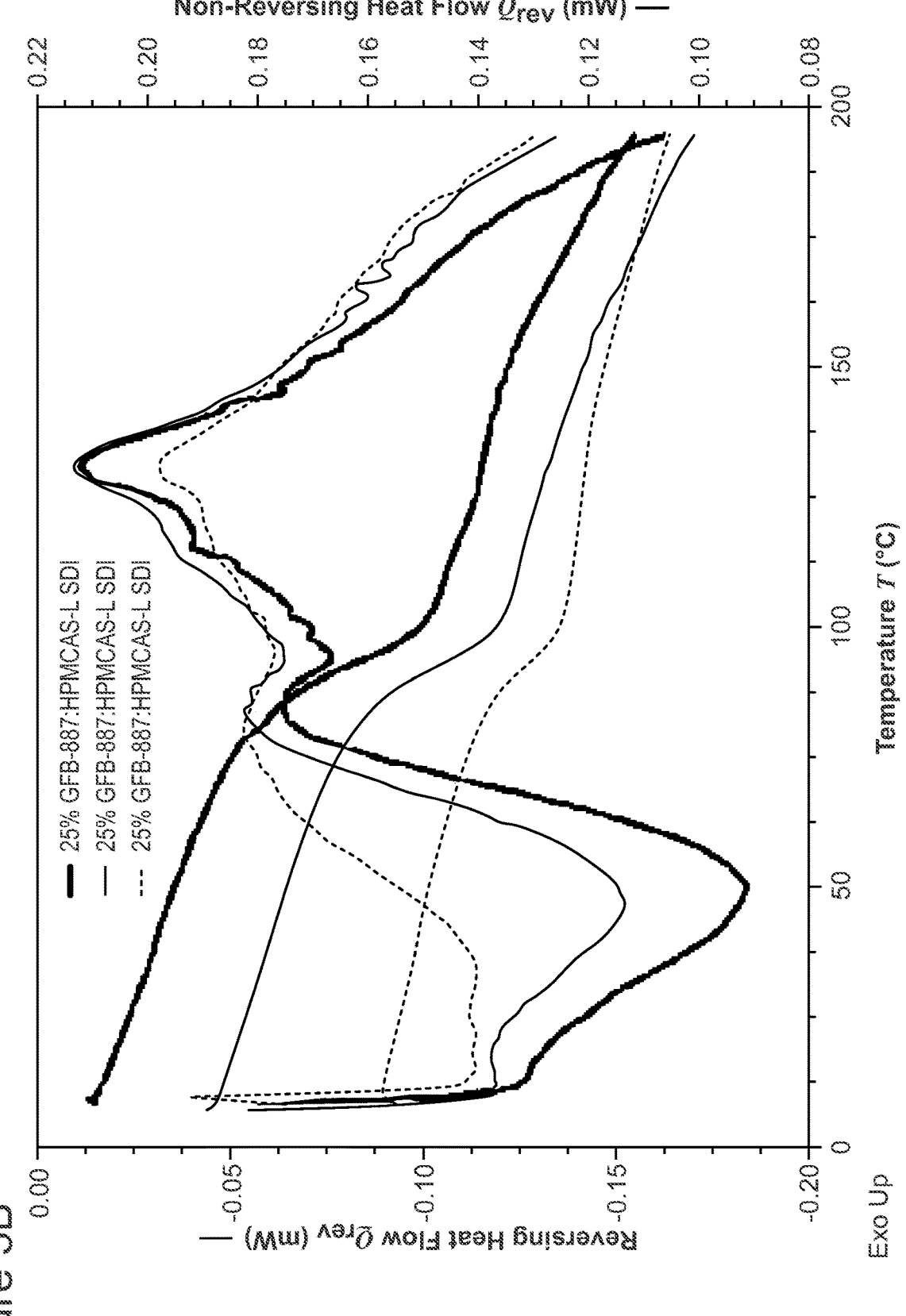
FIG. 5B is a MDSC thermogram showing the Tg of amorphous 25% Compound 1 dispersions in HPMCAS-L.

Thermal analysis done by MDSC was performed on the two amorphous 25% Compound 1 dispersions. DSC showed that both dispersions had a single $T_g$ (FIGS. 5A-B) indicating an intimately mixed amorphous solid dispersion with good homogeneity (Table 14). To ensure long-term physical stability, an SDI should be stored well below the $T_g$ at a given storage condition so that mobility of the drug in the glass dispersion is low.

TABLE 14

MDSC data for amorphous 25% Compound 1 dispersions in
HPMCAS-M and HPMCAS-L

| Formulations | Lot# | Measured Tg (° C.) |
|---|---|---|
| 25:75 Compound 1:HPMCAS-M | G8-854-4 | 91 |
| 25:75 Compound 1:HPMCAS-L | G8-854-8 | 91 |

Figure 6:
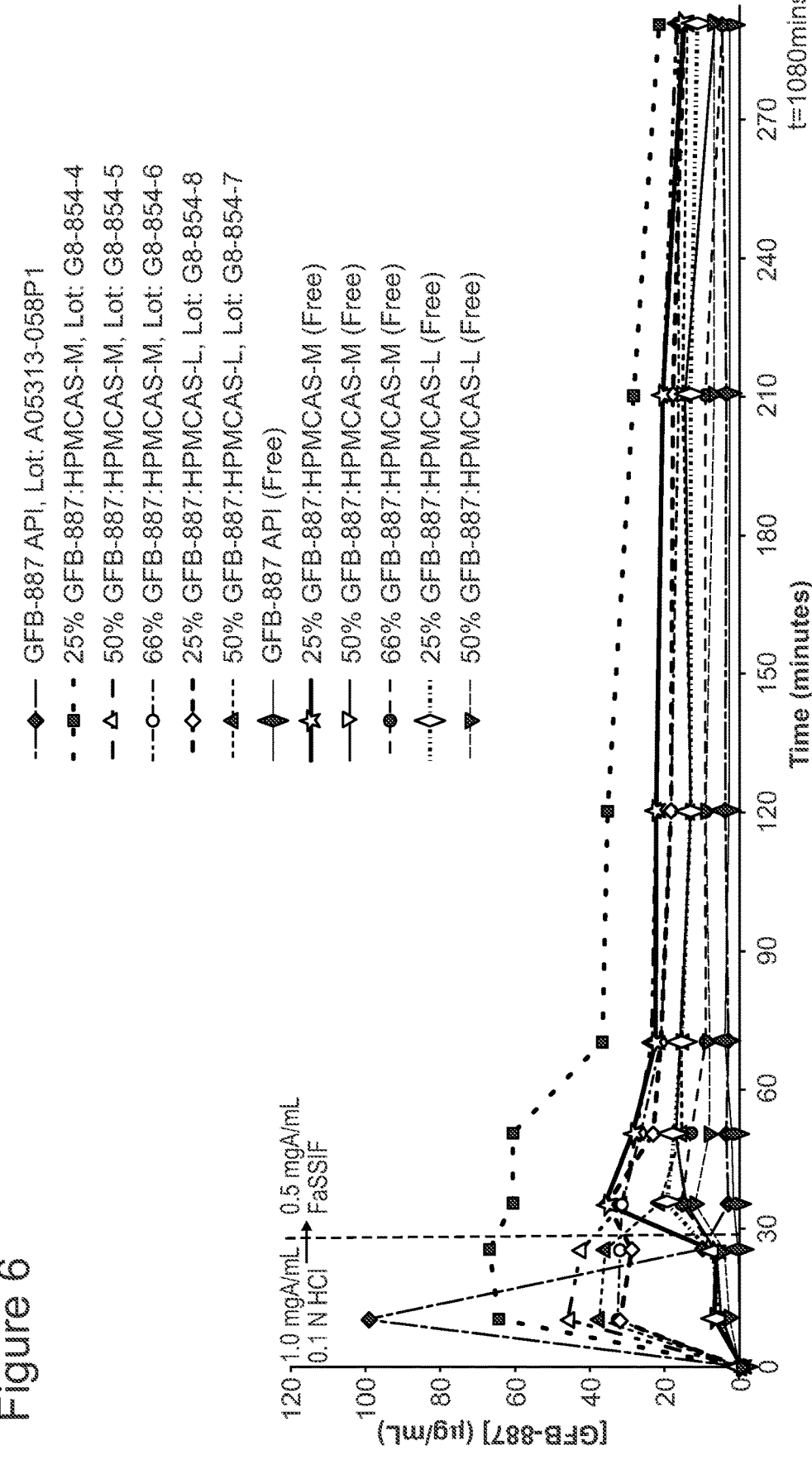
FIG. 6 shows 0.1 N HCl/FaSSIF non-sink dissolution test for Compound 1 feasibility SDI compared to neat crystalline Compound 1

The dissolution performance of the SDI material and crystalline Compound 1 was tested in Patheon's non-sink dissolution test (FIG. 6 and Table 15). The dissolution test is used to measure the supersaturation of drug above the bulk crystalline Compound 1 solubility in biorelevant intestinal media (FaSSIF) after 30 minutes exposure to a low-pH environment. During the test, samples are transitioned from 0.1 N HCl [theoretical $C_{max}$=1000 µA/mL] to FaSSIF [theoretical $C_{max}$=500 µA/mL]. The design of this experiment is to rank order and select lead formulations.

All SDI formulations provided increase in AUC when compared to crystalline API where 25% in HPMCAS-M showed best performance. Free drug concentrations were lower than total drug counterparts, as expected. Free drug levels were consistently lower than total drug samples and were constant across formulations in terms of percentage of total drug. Selected lead formulations were 25% and 50%/drug loads in HPMCAS-M and 25% drug load in HPMCAS-L.

TABLE 15

0.1N HCl/FaSSIF non-sink dissolution test for Compound 1 feasibility SDI compared
to neat crystalline Compound 1 Form H

| Sample | Lot # | Total Drug $C_{max\,GB}$ (µgA/mL) | Total Drug $C_{max\,FaSSIF}$ (µgA/mL)[a] | Total Drug $AUC_{35\text{-}210\,FaSSIF}$ (min * µgA/mL)[c] | Total Drug $C_{210}$ (µgA/mL)[b] | Increase in AUC over API AUC |
|---|---|---|---|---|---|---|
| Compound 1 API | A05313-058P1 | 99 | 3.6 | 600 | 3.5 | 0.4 |
| 25% Compound 1:HPMCAS-M | G8-854-4 | 66 | 60.6 | 6500 | 28.1 | 4.6 |
| 50% Compound 1:HPMCAS-M | G8-854-5 | 46 | 30.9 | 3900 | 20.0 | 2.8 |
| 66% Compound 1:HPMCAS-M | G8-854-6 | 32 | 30.9 | 3400 | 15.8 | 2.4 |
| 25% Compound 1:HPMCAS-L | G8-854-8 | 32 | 34.8 | 3400 | 17.1 | 2.4 |
| 50% Compound 1:HPMCAS-L | G8-854-7 | 37 | 21.1 | 2600 | 14.9 | 1.9 |

Figure 7:
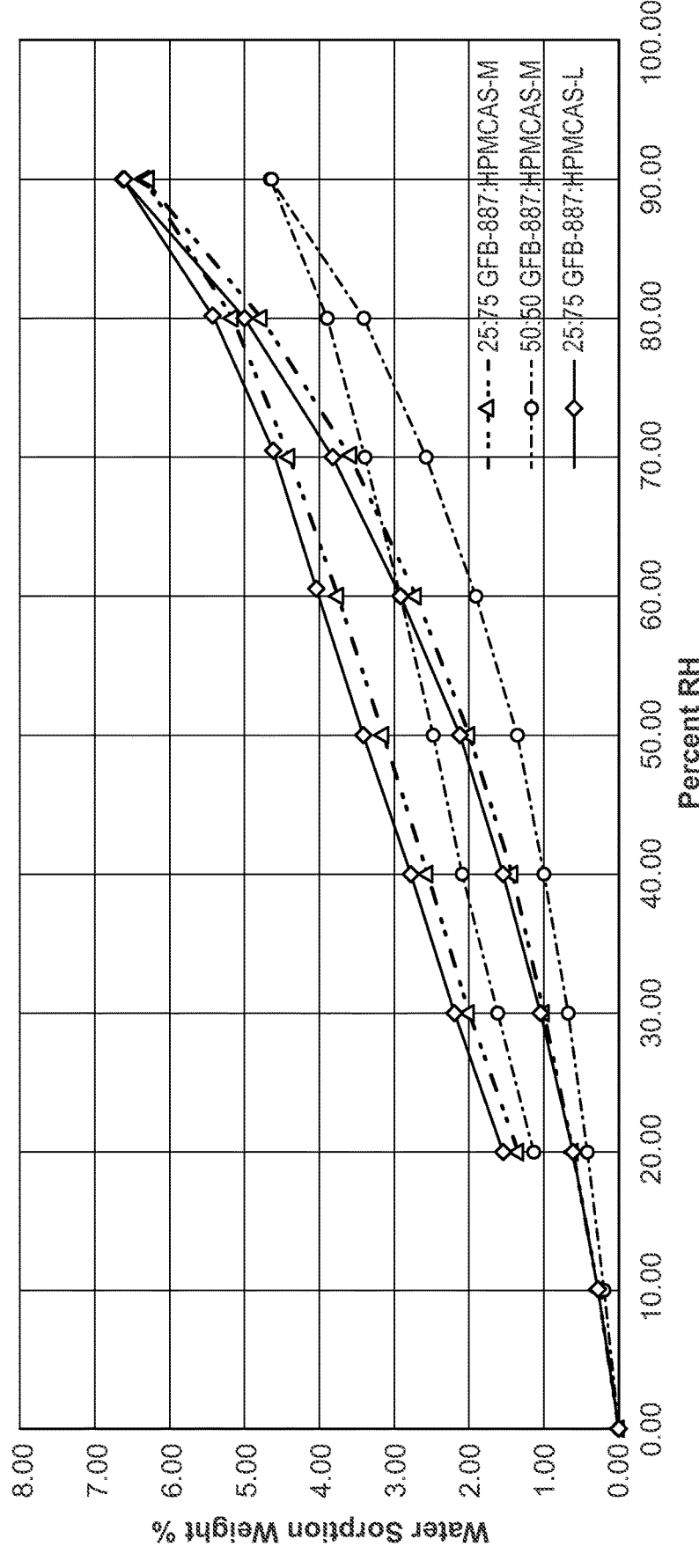
FIG. 7 shows dynamic vapor sorption of Compound 1 SDIs.

[a]$C_{max\,FaSSIF}$ = maximum drug concentration after transfer to FaSSIF
[b]$C_{210}$ = drug concentration at 180 minutes after transfer to FaSSIF
[c]$AUC_{35\text{-}210\,FaSSIF}$ = area under the curve after transfer to FaSSIF from 35 to 210 minutes Lead SDI formulations were tested by dynamic vapor sorption where 50:50 Compound 1:HPMCAS-M dispersion shows least water adsorption, due to lower polymer concentration. All samples show minor hysteresis on desorption (FIG. 7).

Example 20. Focused Screening of Solid Dispersion Polymers: Feasibility Re-Sprays Compound 1 lot used for re-sprays was TJ-GDF-9815-0-A-1. Due to the minor crystallinity observed by XRPD of the 50% and 66% Compound 1 loading dispersions, three additional feasibility formulations were manufactured. Re-spray formulations can be seen in Table 16.

TABLE 16

Summary of feasibility re-spray formulation yields and assigned lot numbers

| Formulations | Lot# | Dry Yield (%) |
|---|---|---|
| 25:75 Compound 1:HPMCAS-M | G8-854-13 | 85 |
| 50:50 Compound 1:HPMCAS-M | G8-854-14 | 56 |
| 50:40:10 Compound 1:HPMCAS-M:Vitamin E TPSG | G8-854-15 | 59 |

Figure 8:
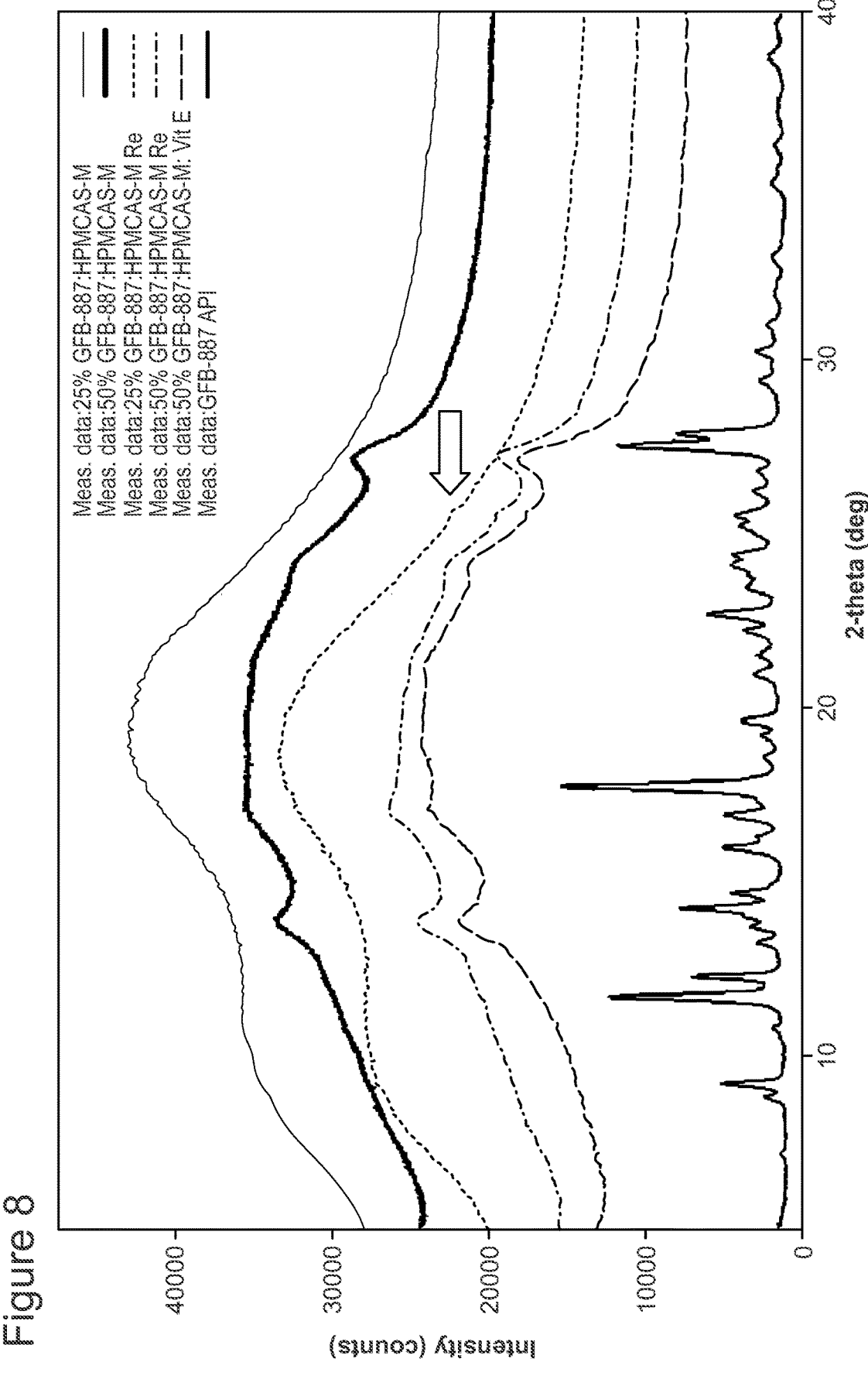
FIG. 8 shows XRPD diffractograms of Compound 1 feasibility re-sprays.

Spray solutions appeared brown and opaque after addition of API, which indicated difference in solubility of API lot from first round of feasibility sprays. Lots G8-854-13 and 14 were sprayed at increased outlet temperature (60° C.) in order to mitigate API rich areas in SDI particles. Lot G8-854-10 included Vitamin E TPGS to help mitigate crystallinity and was sprayed at 40° C. outlet temperature due to the low melting point of TPGS (wax at room temperature). XPRD traces of resprays and original 25:75 Compound 1:HPMCAS-M dispersion can be seen in FIG. 8. Both 50% re-sprays appear to have crystalline peaks similar to original SDIs, where the re-sprayed 25% dispersion appears to have very slight crystalline peak around 26° 2-theta. This data supports observation that the new API lot may not have been fully dissolved in spray solution.

Example 21. Focused Screening of Solid Dispersion Polymers: SDI Accelerated Stability To rapidly assess the physical and chemical stability of the Compound 1 SDI formulations, the lead dispersions (25:75 Compound 1:HPMCAS-M and 25:75 Compound 1:HPMCAS-L) were aged for 4 weeks at 40° C./75% RH and 50° C./75% RH in open and in closed plus desiccant packaging configurations (stability protocol RD-ST-18-940). The SDIs were evaluated for changes in:

Amorphous physical state by XRPD

Chemical stability by HPLC

Figure 9:
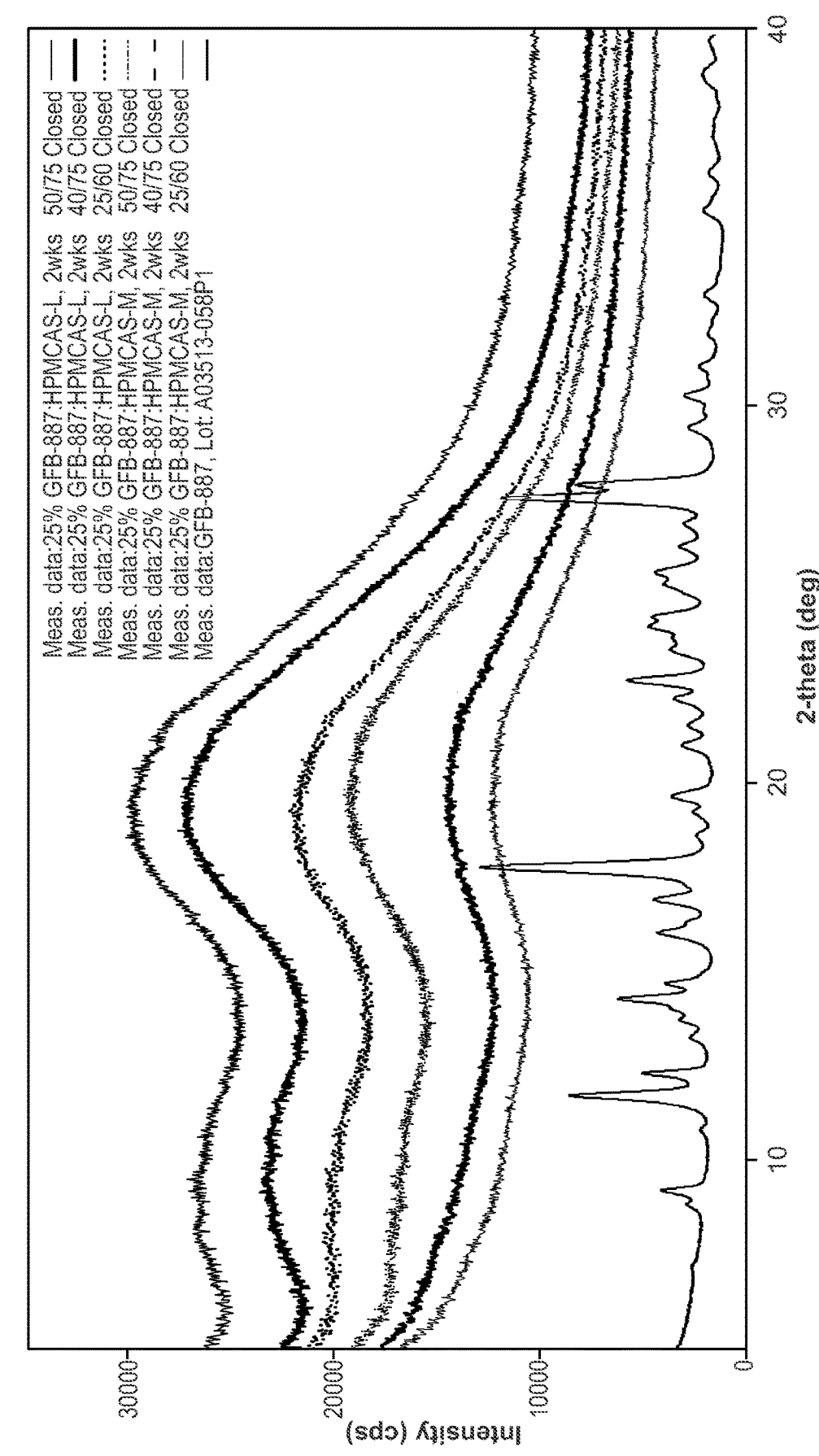
FIG. 9 shows a XRPD diffractogram of aged SDIs after 2 weeks stability. SDIs in closed condition appear to have remained amorphous at 40° C./75% RH and 50° C./75% RH.
Figure 10:
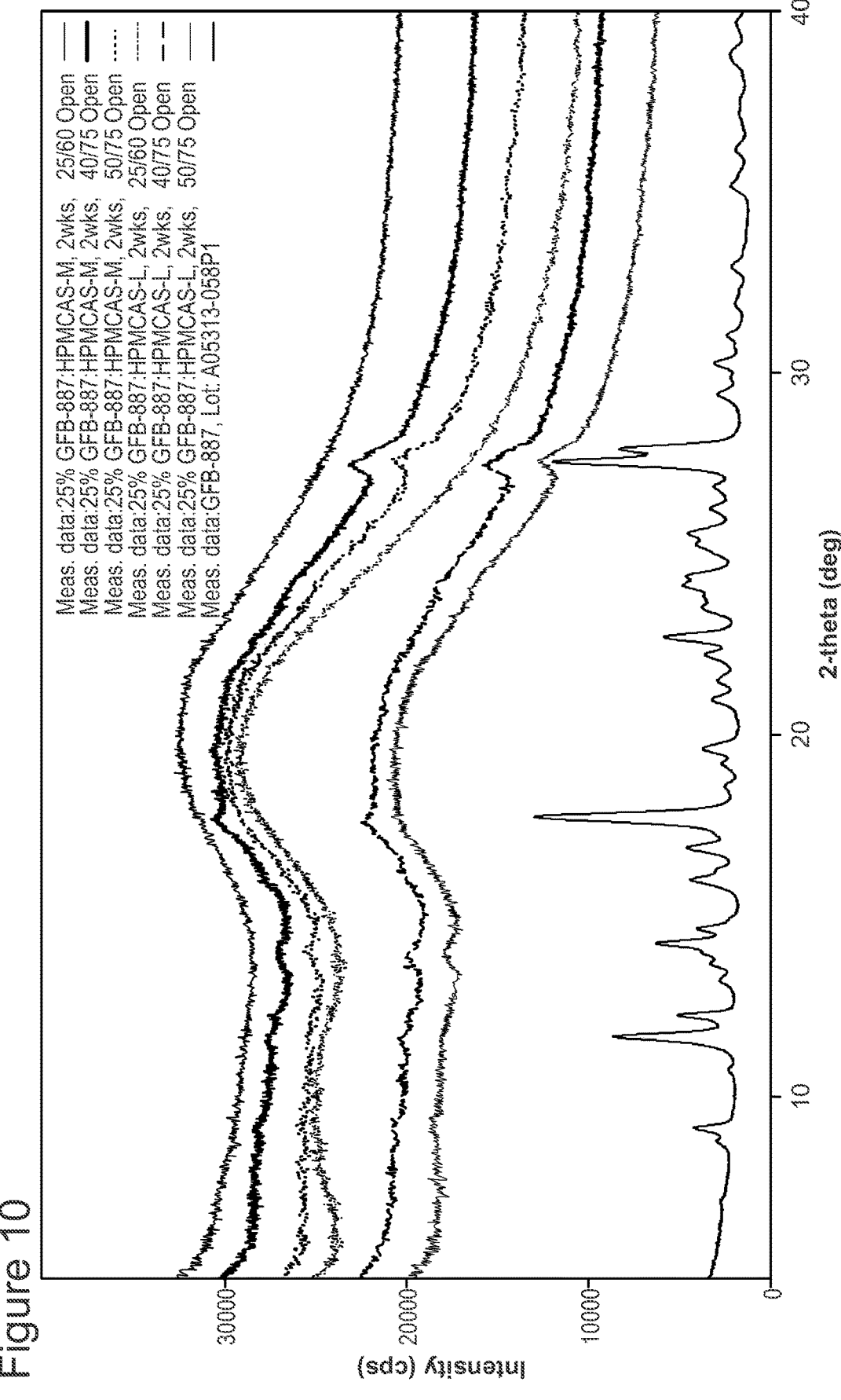
FIG. 10 shows XRPD diffractograms of aged SDIs after 2 weeks stability. SDIs in open condition show crystalline growth at 40° C./75% RH and 50° C./75% RH.

Initial XRPD analysis at 2 weeks of the aged SDI samples shows that all SDI formulations in closed condition with desiccant remained amorphous while open condition showed crystalline growth in the 50% dispersions at 40° C./75% RH and 50° C./75% RH (FIGS. 9-10).

Figure 11:
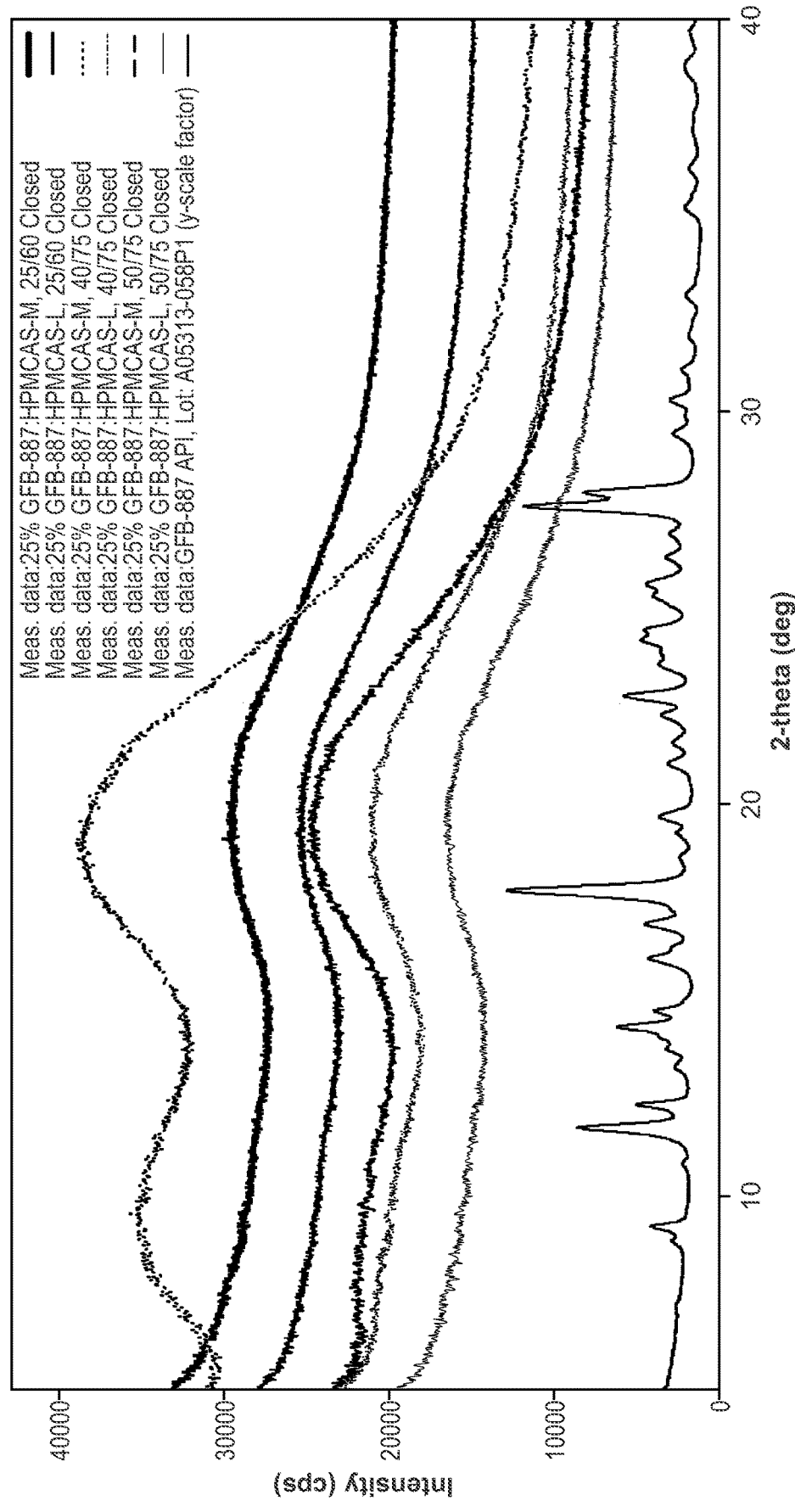
FIG. 11 shows XRPD diffractograms of aged SDIs after 4 weeks stability (closed conditions).
Figure 12:
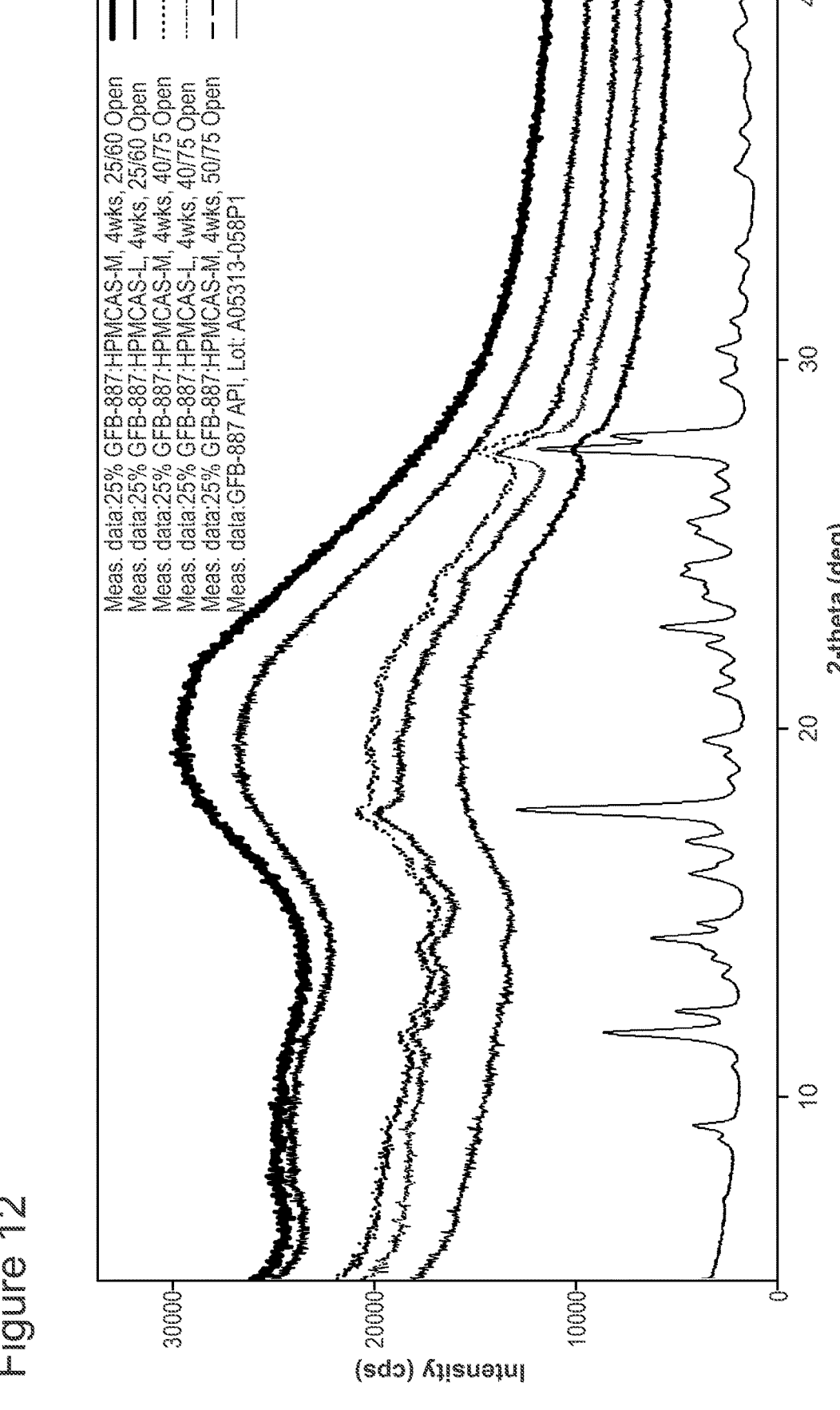
FIG. 12 shows XRPD diffractograms of aged SDIs after 4 weeks stability (open conditions).

Additional XRPD testing was performed on the SDIs at 4 weeks and all closed condition samples remained amorphous. Aggressive 40 and 50° C. open conditions showed crystalline peaks but did not appear to have any further crystalline growth. SDIs at 25° C./60% RH open condition were amorphous after 4 weeks (FIGS. 11-12).

Purity analysis of 25:75 Compound 1:HPMCAS-M after 4 weeks showed no impurity growth in closed condition and the impurity profile matches starting API. Open condition showed significant impurity growth in RRT 0.34, 0.82, 0.91, and 0.96 (Tables 17 and 18), indicating protective packaging would be recommended to protect long-term storage of SDIs.

TABLE 17

Purity results of 25:75 Compound 1:HPMCAS-M SDI after 4 weeks accelerated stabiilty.

| RRT | Compound 1 API, Lot: A05313-058P1 | 25% Compound 1:HPMCAS-M SDI, Lot: G8-854-4 | | | |
|---|---|---|---|---|---|
| | | t = 4 wks, Ambient Closed | t = 4 wks, 25/60 Closed | t = 4 wks, 40/75 Closed | t = 4 wks, 50/75 Closed |
| 0.34 | 0.22% | 0.21% | 0.21% | 0.21% | 0.21% |
| 0.36 | 0.09% | 0.09% | 0.09% | 0.09% | 0.09% |
| 0.37 | Detected, <0.05% | Detected, <0.05% | Detected, <0.05% | Detected, <0.05% | Detected, <0.05% |
| 0.39 | Detected, <0.05% | Detected, <0.05% | Detected, <0.05% | Detected, <0.05% | Detected, <0.05% |
| 0.44 | | | | Detected, <0.05% | |
| 0.48 | | | | | Detected, <0.05% |
| 0.56 | Detected, <0.05% | 0.05% | 0.06% | Detected, <0.05% | Detected, <0.05% |
| 0.66 | 0.05% | 0.06% | 0.07% | 0.06% | 0.06% |
| 0.68 | Detected, <0.05% | 0.05% | Detected, <0.05% | Detected, <0.05% | |
| 0.72 | | | | Detected, <0.05% | |
| 0.80 | Detected, <0.05% | Detected, <0.05% | Detected, <0.05% | Detected, <0.05% | Detected, <0.05% |
| 0.85 | 0.65% | 0.65% | 0.65% | 0.65% | 0.65% |
| 0.88 | | Detected, <0.05% | Detected, <0.05% | Detected, <0.05% | Detected, <0.05% |
| 0.91 | 0.07% | 0.06% | 0.06% | 0.07% | 0.06% |
| 1.02 | 0.32% | 0.32% | 0.33% | 0.33% | 0.32% |
| 1.04 | | Detected, <0.05% | Detected, <0.05% | Detected, <0.05% | Detected, <0.05% |
| 1.10 | 0.07% | 0.06% | 0.06% | 0.06% | 0.06% |
| 1.13 | Detected, <0.05% | Detected, <0.05% | | Detected, <0.05% | Detected, <0.05% |
| 1.25 | | Detected, <0.05% | | | Detected, <0.05% |
| Total | 1.47% | 1.49% | 1.57% | 1.47% | 1.45% |
| Assay (wt %) | 100.0 | 22.0 | 24.8 | 24.1 | 24.1 |

TABLE 18

Purity results of 25:75 Compound 1:HPMCAS-M SDI after 4 weeks accelerated stability.

| RRT | Compound 1 API, Lot: A05313-058P1 | 25% Compound 1:HPMCAS-M SDI, Lot: G8-854-4 | | | |
|---|---|---|---|---|---|
| | | t = 4 wks, Ambient Closed | t = 4 wks, 25/60 Open | t = 4 wks, 40/75 Open | t = 4 wks, 50/75 Open |
| 0.34 | 0.22% | 0.21% | 0.22% | 0.25% | 0.42% |
| 0.36 | 0.09% | 0.09% | 0.09% | 0.11% | 0.18% |
| 0.37 | Detected, <0.05% | Detected, <0.05% | Detected, <0.05% | Detected, <0.05% | Detected, <0.05% |
| 0.39 | Detected, <0.05% | Detected, <0.05% | Detected, <0.05% | Detected, <0.05% | Detected, <0.05% |
| 0.56 | Detected, <0.05% | 0.05% | Detected, <0.05% | Detected, <0.05% | Detected, <0.05% |
| 0.66 | 0.05% | 0.06% | 0.06% | 0.06% | 0.06% |
| 0.68 | | Detected, <0.05% | Detected, <0.05% | Detected, <0.05% | Detected, <0.05% |
| 0.78 | | | | Detected, <0.05% | Detected, <0.05% |
| 0.80 | Detected, <0.05% | Detected, <0.05% | Detected, <0.05% | Detected, <0.05% | Detected, <0.05% |
| 0.82 | | | Detected, <0.05% | 0.08% | 0.49% |
| 0.84 | | | | Detected, <0.05% | 0.06% |

TABLE 18-continued

Purity results of 25:75 Compound 1:HPMCAS-M SDI after 4 weeks accelerated stability.

| | Compound 1 | 25% Compound 1:HPMCAS-M SDI, Lot: G8-854-4 | | | |
|---|---|---|---|---|---|
| RRT | API, Lot: A05313-058P1 | t = 4 wks, Ambient Closed | t = 4 wks, 25/60 Open | t = 4 wks, 40/75 Open | t = 4 wks, 50/75 Open |
| 0.85 | 0.65% | 0.65% | 0.62% | 0.58% | 0.49% |
| 0.86 | | Detected, <0.05% | 0.07% | 0.23% | |
| 0.88 | | Detected, <0.05% | Detected, <0.05% | Detected, <0.05% | |
| 0.89 | | | Detected, <0.05% | Detected, <0.05% | |
| 0.91 | 0.07% | 0.06% | 0.18% | 0.39% | 1.09% |
| 0.95 | | | Detected, <0.05% | Detected, <0.05% | 0.11% |
| 0.96 | | 0.05% | 0.13% | 0.21% | |
| 1.02 | 0.32% | 0.32% | 0.31% | 0.32% | 0.31% |
| 1.04 | | Detected, <0.05% | Detected, <0.05% | Detected, <0.05% | Detected, <0.05% |
| 1.10 | 0.07% | 0.06% | 0.07% | 0.08% | 0.13% |
| 1.13 | Detected, <0.05% | Detected, <0.05% | Detected, <0.05% | Detected, <0.05% | |
| 1.21 | | | | | Detected, <0.05% |
| 1.25 | | Detected, <0.05% | Detected, <0.05% | Detected, <0.05% | |
| Total | 1.47% | 1.49% | 1.61% | 2.08% | 3.77% |
| Assay (wt %) | 100.0 | 22.0 | 23.6 | 23.0 | 21.1 |

Similar results were observed with purity analysis of 25:75 Compound 1:HPMCAS-L SDI after 4 weeks. No impurity growth observed in any closed condition and a significant amount in all open conditions with growth was occurring in RRT 0.82, 0.91, and 0.96. (Tables 19 and 20).

TABLE 19

Purity results of 25:75 Compound 1:HPMCAS-L SDI after 4 weeks accelerated stability.

| | Compound 1 API, | 25% Compound 1:HPMCAS-L SDI, Lot: G8-854-8 | | | |
|---|---|---|---|---|---|
| RRT | Lot: A05313-058P1 | t = 4 wks, Ambient Closed | t = 4 wks, 25/60 Closed | t = 4 wks, 40/75 Closed | t = 4 wks, 50/75 Closed |
| 0.34 | 0.22% | 0.22% | | 0.21% | |
| 0.36 | 0.09% | 0.09% | 0.07% | 0.09% | 0.07% |
| 0.37 | Detected, <0.05% | Detected, <0.05% | | Detected, <0.05% | |
| 0.39 | Detected, <0.05% | Detected, <0.05% | Detected, <0.05% | Detected, <0.05% | Detected, <0.05% |
| 0.44 | | Detected, <0.05% | | | Detected, <0.05% |
| 0.56 | Detected, <0.05% | Detected, <0.05% | Detected, <0.05% | Detected, <0.05% | Detected, <0.05% |
| 0.66 | 0.05% | 0.07% | 0.07% | 0.07% | 0.06% |
| 0.68 | | Detected, <0.05% | Detected, <0.05% | Detected, <0.05% | Detected, <0.05% |
| 0.80 | Detected, <0.05% | Detected, <0.05% | Detected, <0.05% | Detected, <0.05% | Detected, <0.05% |
| 0.85 | 0.65% | 0.65% | 0.65% | 0.65% | 0.65% |
| 0.88 | | Detected, <0.05% | Detected, <0.05% | Detected, <0.05% | Detected, <0.05% |
| 0.91 | 0.07% | 0.06% | 0.05% | 0.06% | 0.06% |
| 1.02 | 0.32% | 0.31% | 0.31% | 0.32% | 0.31% |
| 1.04 | | Detected, <0.05% | Detected, <0.05% | Detected, <0.05% | Detected, <0.05% |

TABLE 19-continued

Purity results of 25:75 Compound 1:HPMCAS-L SDI after 4 weeks accelerated stability.

| | Compound 1 API, | 25% Compound 1:HPMCAS-L SDI, Lot: G8-854-8 | | | |
|---|---|---|---|---|---|
| RRT | Lot: A05313-058P1 | t = 4 wks, Ambient Closed | t = 4 wks, 25/60 Closed | t = 4 wks, 40/75 Closed | t = 4 wks, 50/75 Closed |
| 1.10 | 0.07% | 0.06% | 0.06% | 0.06% | 0.07% |
| 1.13 | Detected, <0.05% | Detected, <0.05% | | Detected, <0.05% | Detected, <0.05% |
| 1.25 | | Detected, <0.05% | Detected, <0.05% | | |
| Total | 1.47% | 1.44% | 1.21% | 1.45% | 1.21% |
| Assay (wt %) | 100.0 | 25.0 | 24.2 | 24.2 | 21.9* |

TABLE 20

Purity results of 25:75 Compound 1:HPMCAS-L SDI after 4 weeks accelerated stability.

| | | 25% Compound 1:HPMCAS-L SDI, Lot: G8-854-8 | | |
|---|---|---|---|---|
| RRT | Compound 1 API, Lot: A05313-058P1 | t = 4 wks, Ambient Closed | t = 4 wks, 25/60 Open | t = 4 wks, 40/75 Open |
| 0.34 | 0.22% | 0.22% | 0.22% | 0.26% |
| 0.36 | 0.09% | 0.09% | 0.09% | 0.12% |
| 0.37 | Detected, <0.05% | Detected, <0.05% | Detected, <0.05% | Detected, <0.05% |
| 0.39 | Detected, <0.05% | Detected, <0.05% | Detected, <0.05% | Detected, <0.05% |
| 0.44 | | Detected, <0.05% | | |
| 0.48 | | | Detected, <0.05% | |
| 0.56 | Detected, <0.05% | Detected, <0.05% | Detected, <0.05% | Detected, <0.05% |
| 0.66 | 0.05% | 0.07% | 0.06% | 0.07% |
| 0.68 | | Detected, <0.05% | Detected, <0.05% | Detected, <0.05% |
| 0.80 | Detected, <0.05% | Detected, <0.05% | Detected, <0.05% | Detected, <0.05% |
| 0.82 | | | Detected, <0.05% | 0.08% |
| 0.85 | 0.65% | 0.65% | 0.62% | 0.58% |
| 0.86 | | | Detected, <0.05% | 0.08% |
| 0.88 | | Detected, <0.05% | Detected, <0.05% | Detected, <0.05% |
| 0.89 | | | Detected, <0.05% | |
| 0.91 | 0.07% | 0.06% | 0.22% | 0.41% |
| 0.95 | | | Detected, <0.05% | Detected, <0.05% |
| 0.96 | | | 0.06% | 0.12% |
| 1.02 | 0.32% | 0.31% | 0.31% | 0.32% |
| 1.04 | | Detected, <0.05% | Detected, <0.05% | Detected, <0.05% |
| 1.10 | 0.07% | 0.06% | 0.07% | 0.09% |
| 1.13 | Detected, <0.05% | Detected, <0.05% | | Detected, <0.05% |
| 1.25 | | Detected, <0.05% | Detected, <0.05% | |
| Total | 1.47% | 1.44% | 1.66% | 2.12% |
| Assay (wt %) | 100.0 | 25.0 | 22.0 | 23.0 |

Accelerated stability data indicates Compound 1 impurity growth is driven at least in part by moisture exposure. The impurity profile has no significant differences, so 25:75

Compound 1:HPMCAS-M SDI was selected as the lead to progress into tablet development due to its performance in the non-sink dissolution test.

Example 22. Spray Dried Intermediate Demonstration Batch

Lot Compound 1 used; TJ-GDF-9815-0-A-1 (crystalline Form H). The nominated SDI formulation was scaled to the MS-150 pilot scale spray dryer and Ekato vacuum dryer for secondary drying. Master formula can be seen in Table 21. Batch size was 14 kg SDI, 200 kg solution.

TABLE 21

Master formula of 25:75 Compound 1:HPMCAS-M SDI

| Component, Grade | Unit Composition | | |
|---|---|---|---|
| | Solid/Solvent wt. % | Solution wt. % | Quantity (kg) |
| Compound 1, NA | 25.00 | 1.75 | 3.50 |
| HPMCAS-MG | 75.00 | 5.25 | 10.50 |
| Solids Total: | 100.00 | 7.00 | 14.00 |
| DCM, NF | 60.00 | 55.80 | 111.60 |
| Methanol, HPLC | 40.00 | 37.20 | 74.40 |
| Solution Total: | 100.00 | 100.00 | 200.00 |

Demonstration batch parameters can be seen in Table 22.

TABLE 22

Spray drying processing parameters on the MS-150 spray dryer for Compound 1 SDI Demonstration Batch

| Parameter | Value |
|---|---|
| Solution Temperature (° C.) | 37.5 ± 2.5 |
| Drying Gas Flow Rate (kg/hr) | 170 |
| Atomization Pressure (bar) | 3.4 |
| Solution Flow Rate (kg/hr) | 9.0 |
| Inlet Temperature (° C.) | 105 |
| Outlet Temperature (° C.) | 60 |
| Condenser Temperature (° C.) | −17 |

Final process yield was 81% and 85% accountability. Recommend processing conditions for GMP processing can be seen in Table 23.

TABLE 23

Recommended spray drying process parameters for 25:75 Compound 1:HPMCAS-M SDI

| Parameter | Value |
|---|---|
| Spray Dryer | Anhydro MS-150 |
| Atomizer | Spray Systems 40100AB/120 (Anti-Bearding Nozzle Tip) |
| SDI Formulation | 25:75 Compound 1:HPMCAS-M |
| Solvent System (wt. %) | 60:40 DCM:Methanol |
| Solids Loading (wt. %) | 7.00 |
| Solution Temperature (° C.) | 37.5 ± 2.5 |
| Inlet Temperature, $T_{in}$ (° C.) | 105.0 ± 20.0 |
| Outlet Temperature, $T_{out}$ (° C.) | 60.0 ± 5.0 |
| Condenser Set Point (° C.) | −35.0 |
| Solution Feed Rate (kg/hr) | 10.0 |
| Drying Gas Flow Rate (kg/hr) | 170.0 |
| Atomization Pressure (Bar) | 3.0 ± 1.0 |
| Ekato Temperature (° C.) | 40° C. |
| Ekato Vacuum Setting (mBar) | −900 |
| Ekato Agitator Speed (rpm) | 20 |

TABLE 23-continued

Recommended spray drying process parameters for 25:75 Compound 1:HPMCAS-M SDI

| Parameter | Value |
|---|---|
| Ekato Drying Time (° C.) | ≥8 hours |
| Target Residual Solvent Level, per ICH | DCM: <600 ppm; Methanol: <3000 ppm |

The use of an anti-bearding nozzle tip is recommended for GMP manufacturing.

Example 23. Compound 1 SDI Demonstration Batch Analytical Testing

Demonstration batch Compound 1 SDI was tested for appearance, potency/related substances, water content, residual solvent, $T_g$, amorphous character, particle size distribution, particle morphology, and bulk/tapped density. All results were captured in a Certificate of Testing (CoT) and can be seen in FIG. 13.

Example 24. Demonstration Batch Solution and Wet SDI Stability

Spray solution sample from lot D-18-078 was collected prior to spray drying to determine maximum solution hold time. Solution sample was held at 40° C. and tested at t=0, 1, 5, 9, and 15 days for assay/related substances and appearance. Spray solution was stable for 5 days and degradation was observed at the 9 and 15 day time points. Degradation was observed at RRT=0.85, 0.86, 0.92, 0.94, 0.96, 1.47, 1.52, and 1.56. Solution remained "transparent orange" in color through the 15 day time point. Spray solution stability was re-performed with duplicate measurements to confirm the results FIG. 14).

The degradation profile on retest was similar to the initial spray solution testing. Based on the spray solution re-test data, a conservative 3 day stability for spray solution at 40° C. was assigned.

Figure 15B:
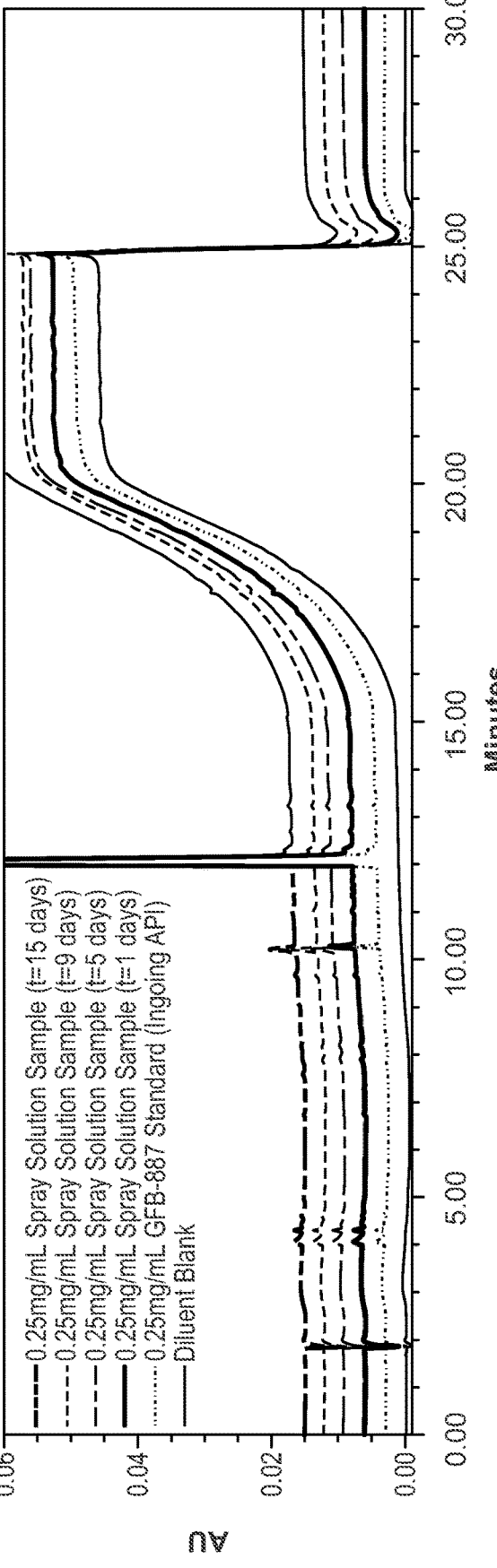
FIG. 15B shows a chromatogram of Compound 1 wet SDI stability through 15 days at room temperature.

Wet SDI was tested for appearance, assay/related substances, particle morphology and amorphous character at t=0, 1, 5, 9, and 15 days at room temperature. Testing was necessary to determine the maximum hold time of wet SDI prior to secondary drying in the Ekato vacuum dryer. Appearance remained "off-white tannish powder" throughout testing. Assay/related substance results of wet SDI can be seen in FIG. 15A and FIG. 15B.

Figure 16:
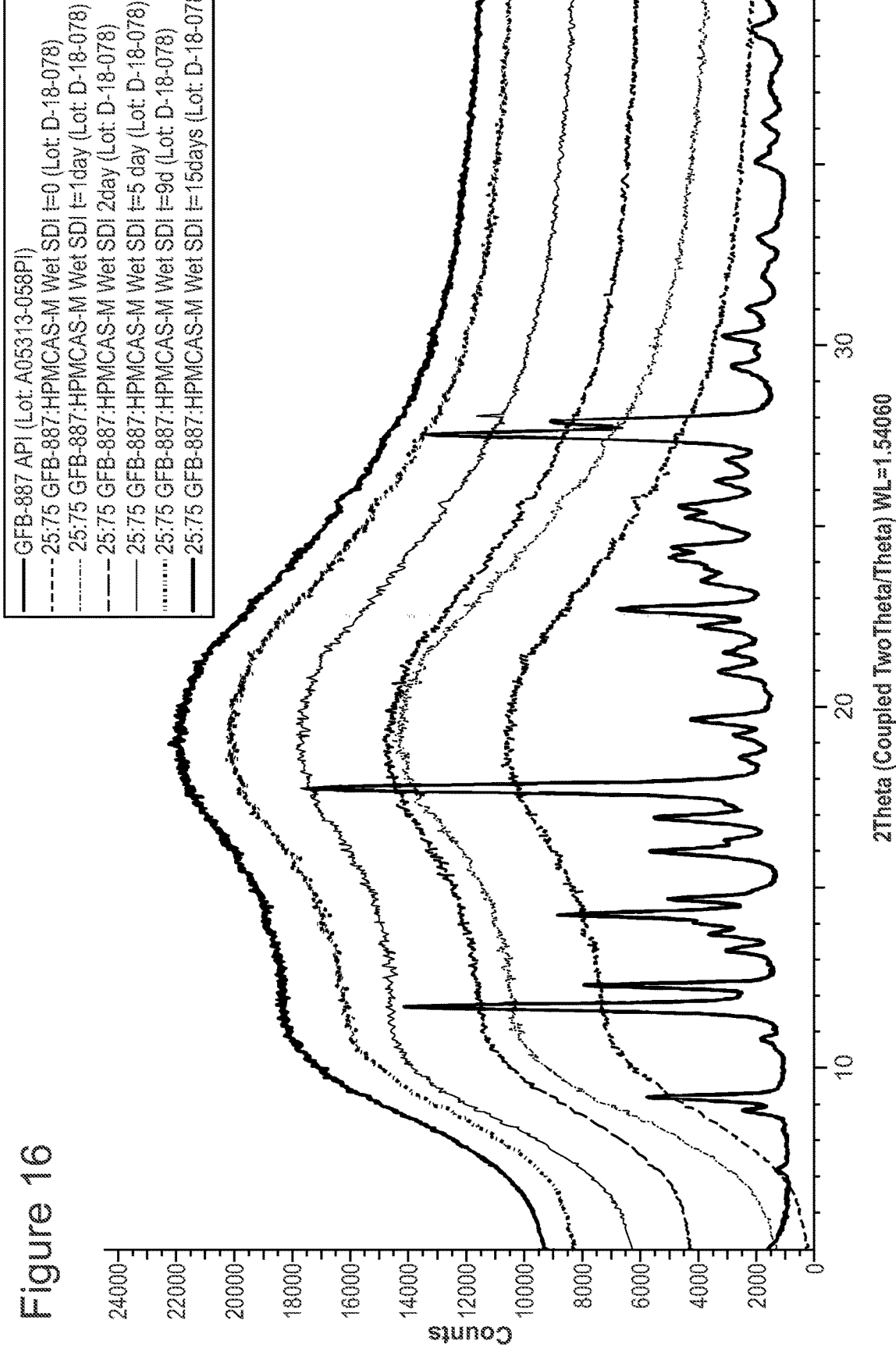
FIG. 16 shows a diffractogram of Compound 1 wet SDI stability through 15 days at room temperature.
Figure 17:
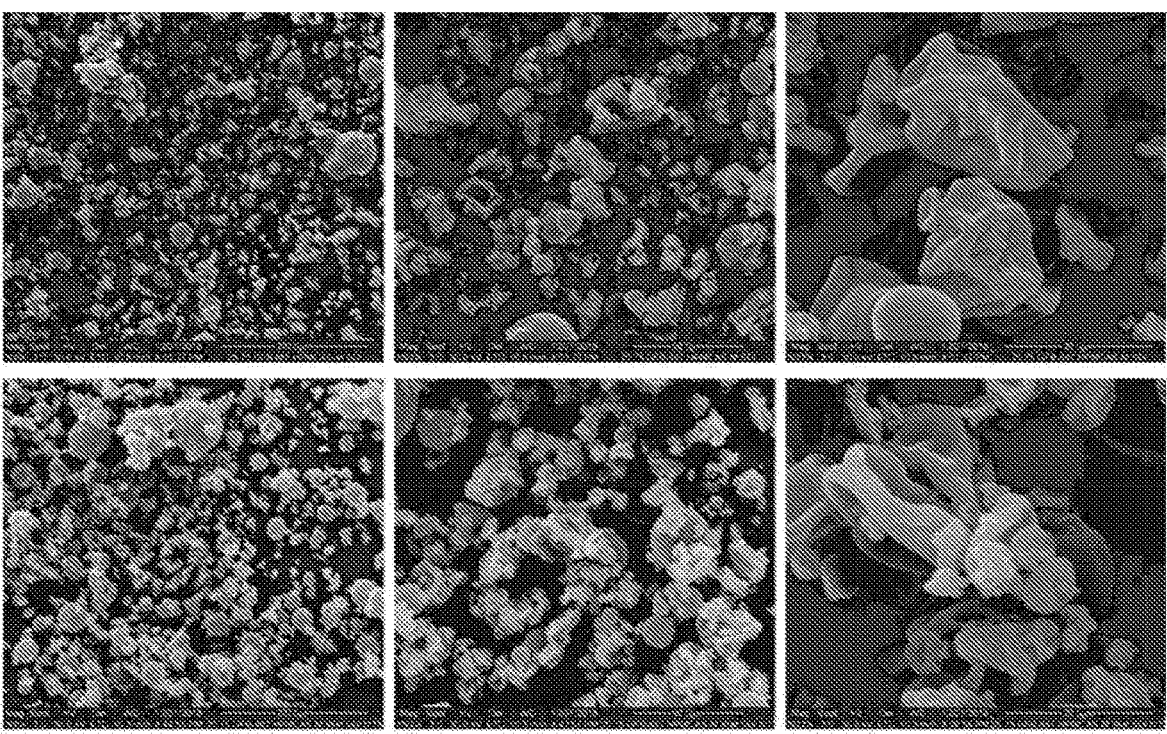
FIG. 17 shows SEM images of t=0 (top row) and t=15 days (bottom row) of Compound 1 wet SDI held at room temperature.

Wet SDI was chemically stable for at least 15 days at room temperature. Wet SDI remained amorphous by XRPD and particle morphology did not appear to change after 15 days (FIGS. 16 and 17).

Crystallinity observed at ~26° 2-theta throughout stability and initial wet SDI. Peak at 26° 2-theta did not appear to grow.

SDI is of typical collapsed sphere morphology with no crystallinity observed. Fifteen day wet SDI morphology is equivalent to dried SDI morphology with no observed changes on stability.

Example 25. Prototype Compound 1 Tablet Development

Four tablet formulations were selected to evaluate excipient compatibility and tablet physical properties. Filler (mannitol or lactose) and super disintegrant (croscarmellose sodium or crospovidone) were altered to find the best combination. Formulations can be seen in Table 24.

TABLE 24

| Component | % w/w | | | |
|---|---|---|---|---|
| 25:75 Compound 1:HPMCAS-M (SDI) | 50.00 | 50.00 | 50.00 | 50.00 |
| Avicel PH-101 (Microcrystalline Cellulose) | 21.00 | 21.00 | 21.00 | 21.00 |
| Fast Flo #316 ( Lactose) | 21.00 | 21.00 | — | — |
| Pearlitol 100SD (Mannitol) | — | — | 21.00 | 21.00 |
| Kollidon CL (Crospovidone) | — | 6.00 | — | 6.00 |
| Ac-Di-Sol (Croscarmellose Sodium) | 6.00 | — | 6.00 | — |
| Cab-O-Sil (Silicon Dioxide) | 1.00 | 1.00 | 1.00 | 1.00 |
| PRUV (Sodium Stearyl Fumarate) | 1.00 | 1.00 | 1.00 | 1.00 |
| Total: | 100.00 | 100.00 | 100.00 | 100.00 |
| Lot Number | G8-854-16-1 | G8-854-16-2 | G8-854-17-1 | G8-854-17-2 |

Compound 1 prototype tablet formulations to evaluate excipient compatibility and tablet physical properties.

Tablet strength is 50 mg Compound 1 with a 400 mg total tablet weight.

Figure 18:
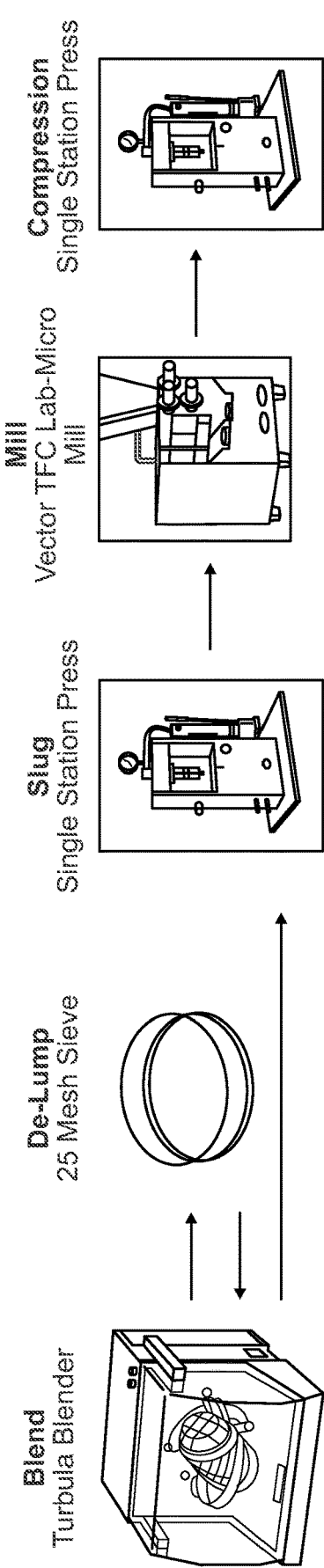
FIG. 18. Process flow diagram for the manufacture of Compound 1 prototype tablets.

Tablets were made at 50 mg Compound 1 strength and 400 mg total tablet weight. Prototype formulations were manufactured via slug and mill to simulate a dry granulation process. Process flow chart can be seen in FIG. 18.

Intra-granular blend was slugged to a solid fraction of ~0.70 using 0.875" flat faced tooling. (True densities of prototype blends assumed to be 1.35 g/cc). Compacts were then milled using a Vector TFC-Micro mill with a 20 mesh screen. Prototype tablets were manufactured on the Natoli Single Station manual press. Tabletability, compressibility, compatibility, and disintegration profiles were generated for all formulations using 0.2505"×0.5385" modified oval tooling over the compression range 50-300 MPa (FIG. 19). (See FIGS. 31-32 for applicable tooling drawings.)

All formulations have similar compression profiles which are likely being dictated by the high level of SDI. Tablet formulations achieve high tensile strength at relatively low compression pressure. Ac-Di-Sol is much more effective disintegrant than Kollidon CL. Formulations containing Kollidon CL have much steeper slope on disintegration profile. Fluctuations in compression pressure can cause large difference in disintegration time and potentially impact dissolution. Formulations containing Ac-Di-Sol were selected for accelerated stability studies and based on dissolution and cyno PK study with a single 50 mg tablet in fasted animals. The slower rate of dissolution for the crospovidone containing tablets was also seen with a ~50% decrease in AUC versus tablets containing Ac-Di-Sol. There was no difference observed between tablets containing lactose versus mannitol.

Example 26. Prototype Compound 1 Tablet Accelerated Stability

Selected prototype tablets (Lactose/Ac-Di-Sol and Mannitol/Ac-Di-Sol) were placed on accelerated stability and stored at 40 C/75% RH and 25 C/60% RH, open and closed conditions. Tablets were tested for assay/related substances, non-sink dissolution, and disintegration after 4 weeks. Assay/related substances data for both tablets can be seen in Tables 25 and 26.

TABLE 25

Assay and related substances of Compound 1 prototype tablets containing Lactose/Ac-Di-Sol after 4 week accelerated stability.

| Material | Compound 1 API | 50 mgA Compound 1 Tablet/lactose/Ac-Di-Sol, 400 mg | | | |
|---|---|---|---|---|---|
| Lot# | TJ-GDF-9815-0-A-1 | G8-854-16-1 | | | |
| Storage Condition | Room Temp | 4 weeks/25° C./ 60% RH/Closed | 4 weeks/40° C./ 75% RH/Closed | 4 weeks/25° C./ 60% RH/OPEN | 4 weeks/40° C./ 75% RH/OPEN |
| Packaging Configuration | Sealed LDPE bag | Tablets in induction heat-sealed 75 cc HDPE bottle w/ 1 g silica gel desiccant | | Tablets in 75 cc HDPE bottle without cap | |
| RRT | | | | | |
| 0.34 | 0.23% | 0.23% | 0.22% | 0.23% | 0.27% |
| 0.36 | 0.11% | 0.11% | 0.11% | 0.11% | 0.14% |
| 0.37 | Detected, <0.05% | Detected, <0.05% | Detected, <0.05% | Detected, <0.05% | Detected, <0.05% |
| 0.38 | Detected, <0.05% | Detected, <0.05% | Detected, <0.05% | Detected, <0.05% | Detected, <0.05% |
| 0.56 | Detected, <0.05% | Detected, <0.05% | Detected, <0.05% | | Detected, <0.05% |
| 0.65 | Detected, <0.05% | Detected, <0.05% | Detected, <0.05% | Detected, <0.05% | |
| 0.68 | Detected, <0.05% | Detected, <0.05% | | Detected, <0.05% | Detected, <0.05% |
| 0.80 | 0.06% | Detected, <0.05% | Detected, <0.05% | Detected, <0.05% | Detected, <0.05% |
| 0.85 | 0.40% | 0.38% | 0.42% | 0.39% | 0.38% |
| 0.88 | | Detected, <0.05% | | | |

TABLE 25-continued

Assay and related substances of Compound 1 prototype
tablets containing Lactose/Ac-Di-Sol after 4 week accelerated stability.

| RRT | API | | | | |
|---|---|---|---|---|---|
| 0.91 | Detected, <0.05% | 0.07% | 0.07% | 0.07% | 0.10% |
| 0.96 | | | | Detected, <0.05% | Detected, <0.05% |
| 1.02 | 0.07% | 0.07% | 0.06% | 0.06% | 0.06% |
| 1.10 | Detected, <0.05% | Detected, <0.05% | Detected, <0.05% | | Detected, <0.05% |
| 1.44 | Detected, <0.05% | Detected, <0.05% | | Detected, <0.05% | Detected, <0.05% |
| 1.47 | 0.07% | 0.07% | 0.06% | 0.07% | 0.07% |
| 1.50 | Detected, <0.05% | | | | Detected, <0.05% |
| 1.58 | Detected, <0.05% | Detected, <0.05% | Detected, <0.05% | Detected, <0.05% | 0.05% |
| Total Impurities | 0.93% | 0.92% | 0.96% | 0 93% | 1.07% |
| Potency (% or mgA/TAB) | 97.70% | 48.4 ± 0.1 | 48.5 ± 0.0 | 47.8 ± 0.1 | 49.0 ± 0.3 |

Lactose/Ac-Di-Sol tablets showed small amounts of degradant growth at RRT=0.34, 0.36, and 0.91 compared with bulk API in 40 C/75% RH open only. Other conditions showed similar impurity profiles compared with API.

TABLE 26

Assay and related substances of
Compound 1 prototype tablets containing Mannitol/Ac-Di-Sol after 4 week accelerated stability.

| Material | Compound 1 API | 50 mgA Compound 1 Tablet/mannitol/Ac-Di-Sol, 400 mg | | | |
|---|---|---|---|---|---|
| Lot# | TJ-GDF-9815-0-A-1 | G8-854-17-1 | | | |
| Storage Condition | Room Temp | 4 weeks/25° C./ 60% RH/Closed | 4 weeks/40° C./ 75% RH/Closed | 4 weeks/25° C./ 60% RH/OPEN | 4 weeks/40° C./ 75% RH/OPEN |
| Packaging Configuration | Sealed LDPE bag | Tablets in induction heat-sealed 75 cc HDPE bottle w/ 1 g silica gel desiccant | | Tablets in 75 cc HDPE bottle without cap | |
| RRT | | | | | |
| 0.34 | 0.23% | 0.22% | 0.23% | 0.25% | 0.27% |
| 0.36 | 0.11% | 0.11% | 0.11% | 0.12% | 0.14% |
| 0.37 | Detected, <0.05% | Detected, <0.05% | Detected, <0.05% | Detected, <0.05% | Detected, <0.05% |
| 0.38 | Detected, <0.05% | Detected, <0.05% | Detected, <0.05% | Detected, <0.05% | Detected, <0.05% |
| 0.56 | Detected, <0.05% | | | 0.08% | |
| 0.65 | Detected, <0.05% | Detected, <0.05% | | Detected, <0.05% | Detected, <0.05% |
| 0.68 | Detected, <0.05% | | Detected, <0.05% | Detected, <0.05% | Detected, <0.05% |
| 0.80 | 0.06% | 0.05% | Detected, <0.05% | Detected, <0.05% | Detected, <0.05% |
| 0.85 | 0.40% | 0.42% | 0.45% | 0.40% | 0.38% |
| 0.91 | Detected, <0.05% | 0.06% | 0.06% | 0.07% | 0.10% |
| 0.96 | | | | Detected, <0.05% | Detected, <0.05% |
| 1.02 | 0.07% | 0.06% | 0.06% | 0.06% | 0.06% |
| 1.10 | Detected, <0.05% | Detected, <0.05% | | Detected, <0.05% | |
| 1.44 | Detected, <0.05% | Detected, <0.05% | | Detected, <0.05% | Detected, <0.05% |
| 1.47 | 0.07% | 0.07% | 0.07% | 0.07% | 0.07% |
| 1.50 | Detected, <0.05% | | | | |
| 1.58 | Detected, <0.05% | Detected, <0.05% | Detected, <0.05% | Detected, <0.05% | 0.05% |
| Total Impurities | 0.93% | 0.98% | 0.98% | 1.04% | 1.07% |
| Potency (% or mgA/TAB) | 97.70% | 48.4 ± 0.1 | 48.5 ± 0.0 | 47.8 ± 0.1 | 49.0 ± 0.3 |

Mannitol/Ac-Di-Sol tablets stored at 40 C/75% RH open showed small amounts of degradant growth, similar to Lactose/Ac-Di-Sol tablets. Other conditions showed similar profiles to bulk API. All tablets from both formulations matched target potency values.

Figure 20:
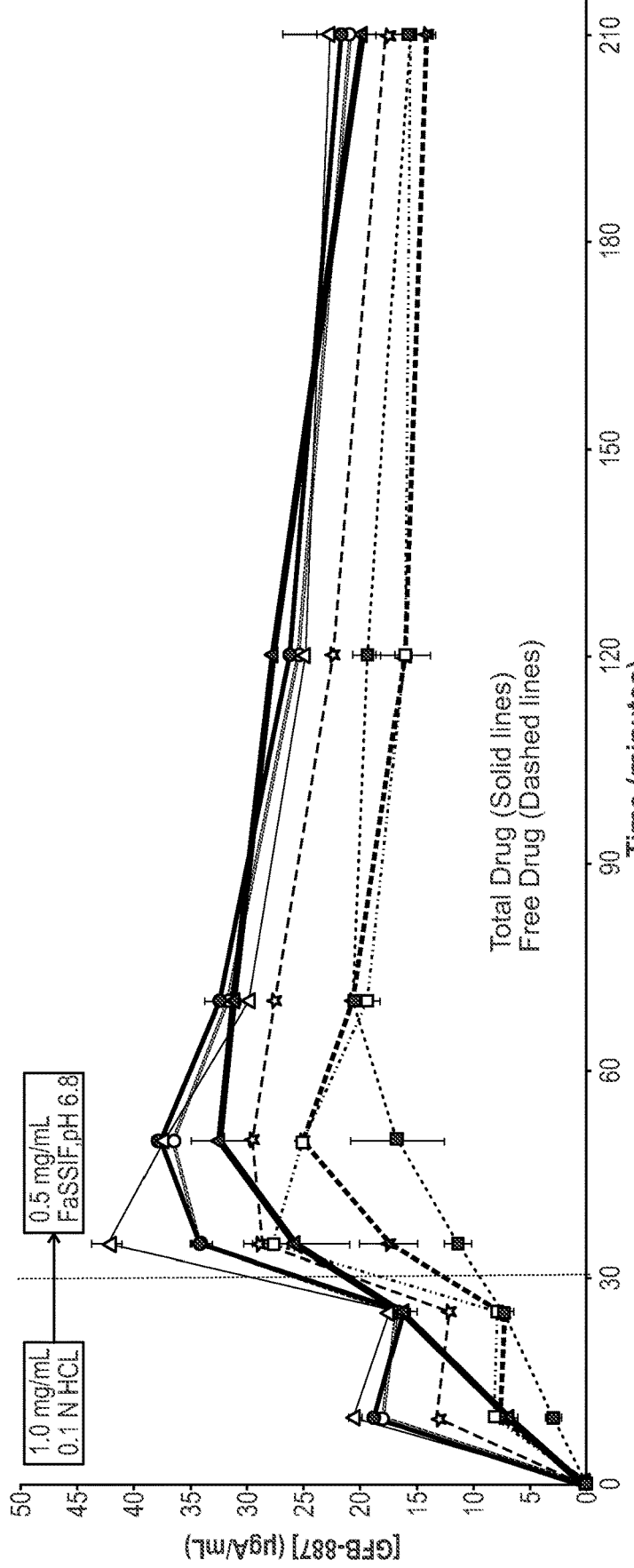
FIG. 20. Non-sink dissolution of 50 mg Compound 1 prototype tablets containing Lactose and Ac-Di-Sol after 4 weeks accelerated stability.
Figure 21:
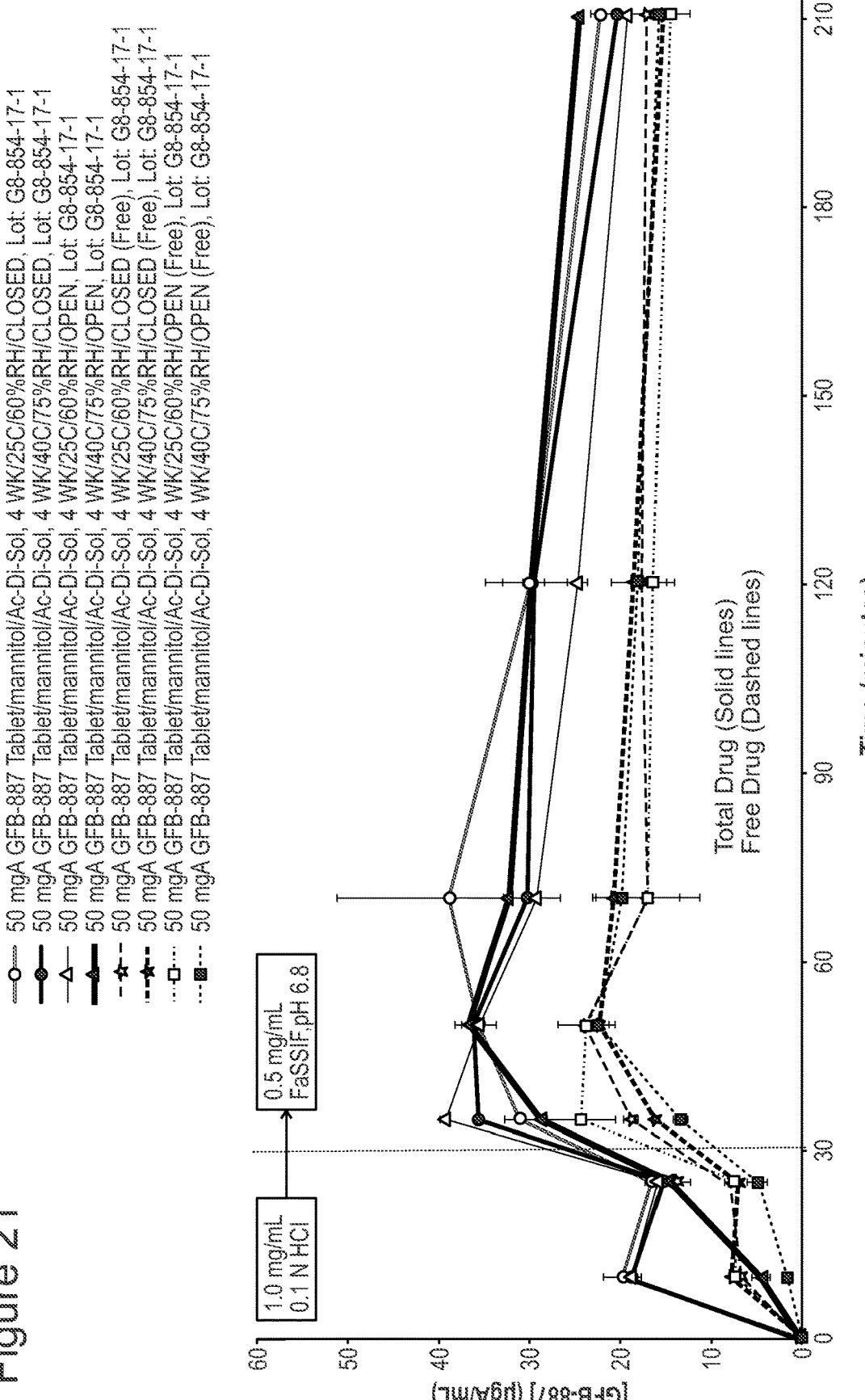
FIG. 21. Non-sink dissolution of 50 mg Compound 1 prototype tablets containing Mannitol and Ac-Di-Sol after 4 weeks accelerated stability.

Both tablet formulations at all conditions were tested for non-sink dissolution and were found to show similar performance for total drug and free drug (FIGS. 20 and 21).

Tablets showed similar disintegration times except for 40° C./75% RH open condition, which was significantly longer. This is likely due to the Ac-Di-Sol and Avicel in the formulations absorbing moisture and swelling during stability, which means all the disintegrant has already been activated. When these tablets are placed in the disintegration bath there is no force that will swell and break the tablets apart. Table 27 shows disintegration times and appearance data.

Figure 23:
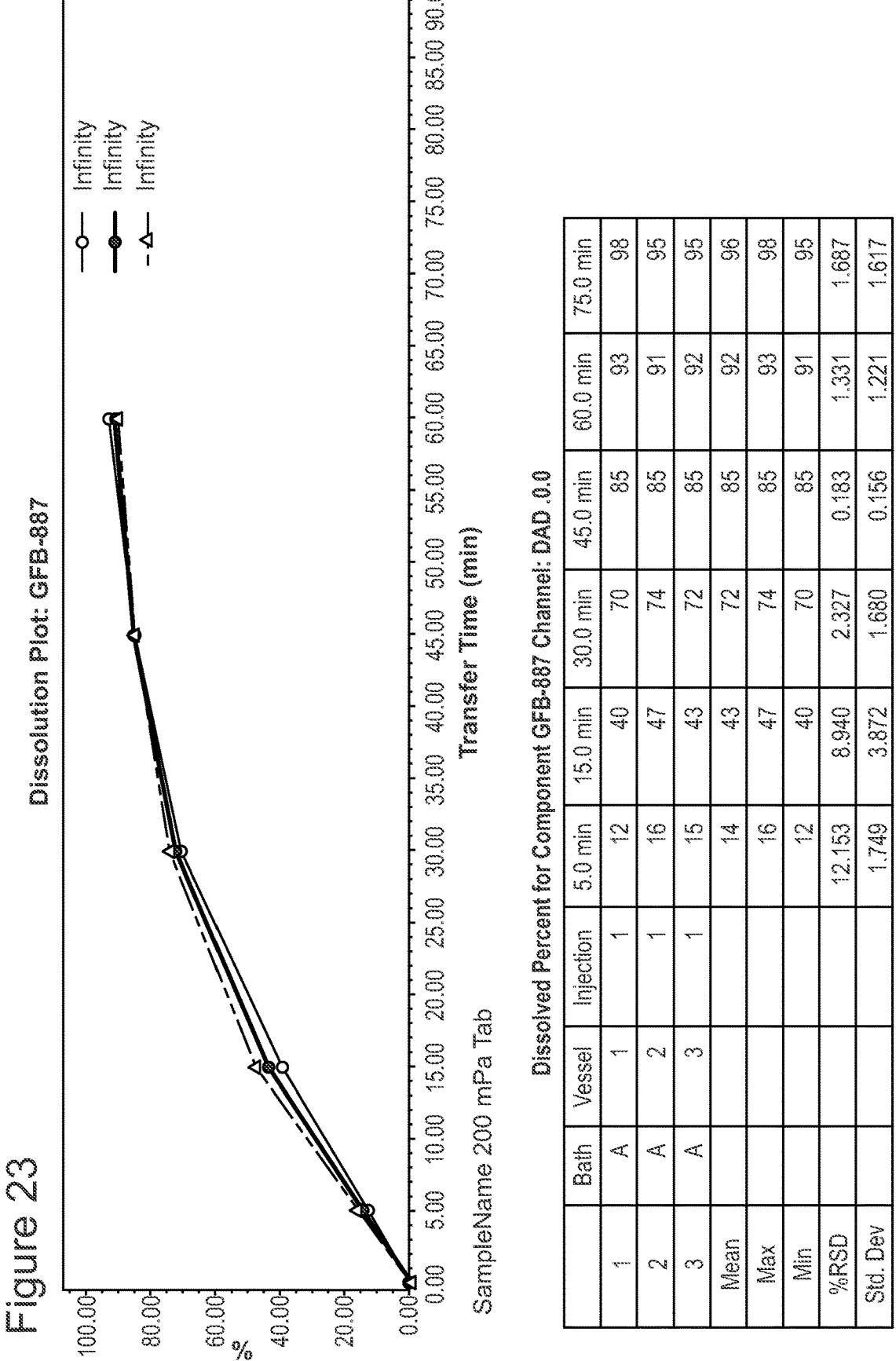
FIG. 23. Dissolution of Compound 1 tablets, 100 mg compressed at 200 MPa.
Figure 24:
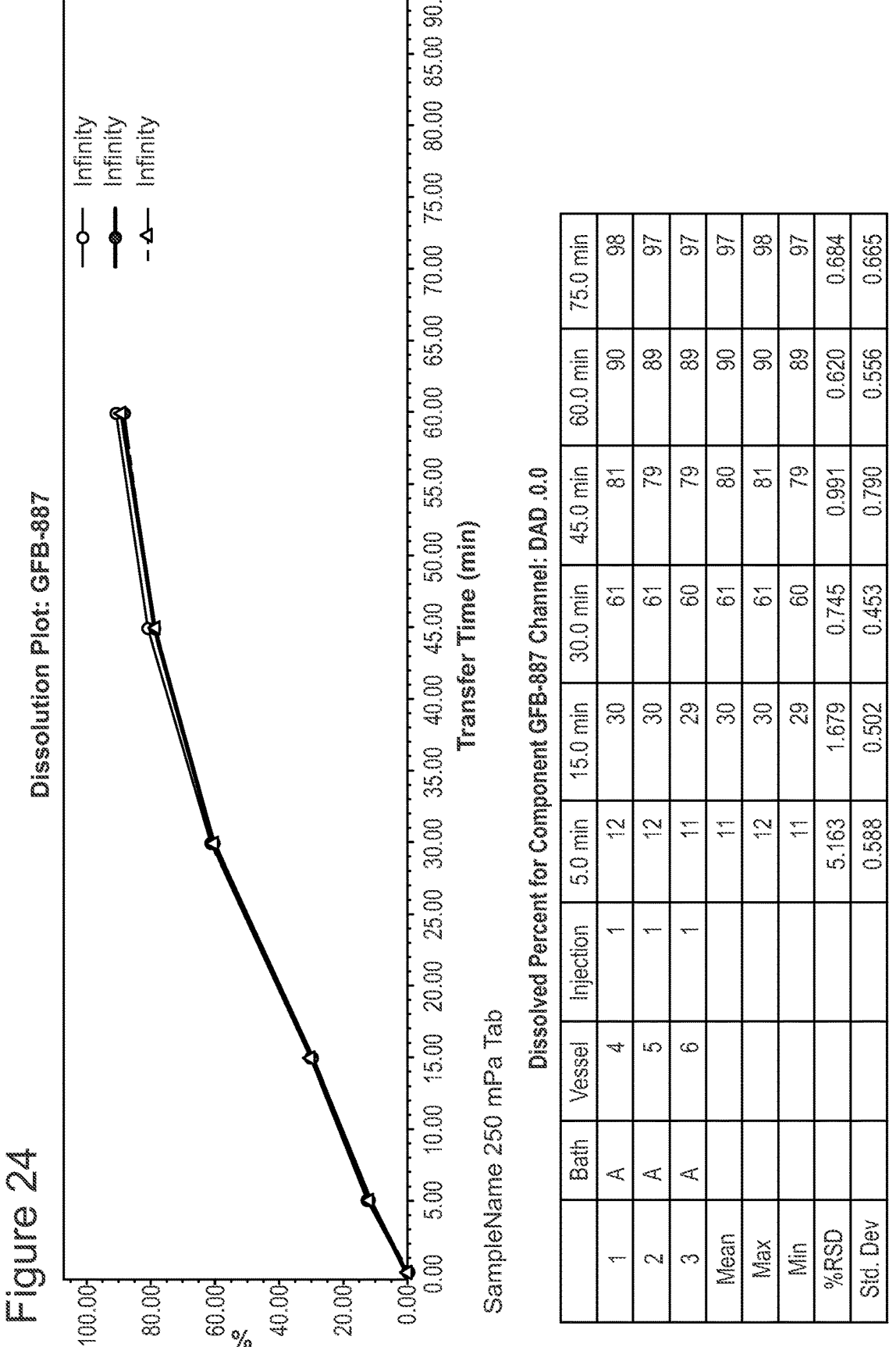
FIG. 24. Dissolution of Compound 1 tablets, 100 mg compressed at 250 MPa.
Figure 25:
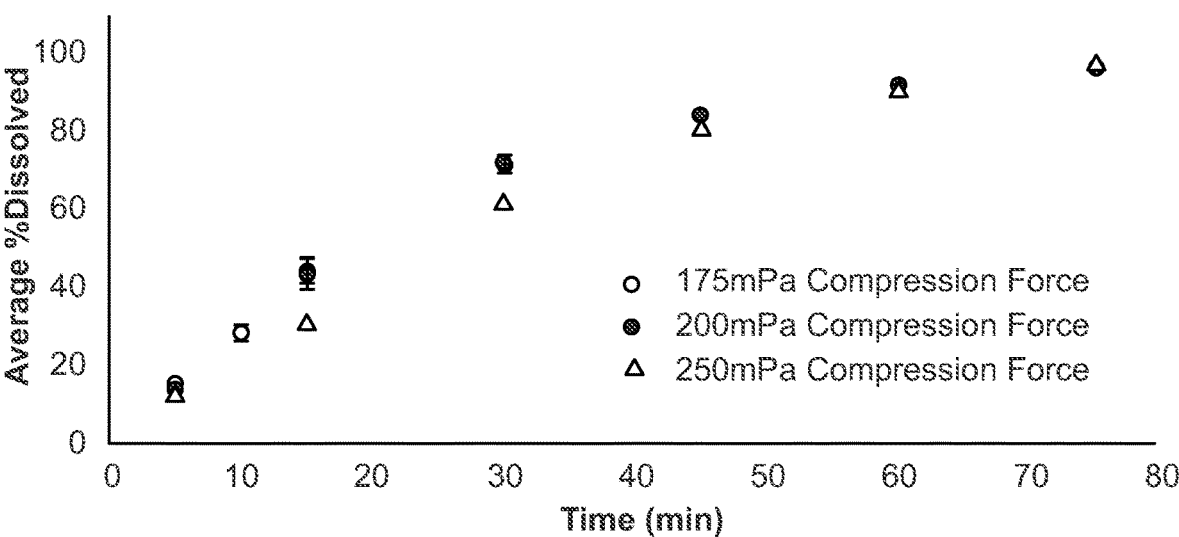
FIG. 25. Dissolution of Compound 1 tablets, 100 mg; an overlay of all tablet compression forces to evaluate formulation robustness.

Tabletability, compressibility, and compactability graphs show prototype tablets are stronger than demonstration batch tablets. This is due to the difference in dwell time between the two processes (rotary tablet press has significantly less dwell time). Disintegration profiles of the 50 mg prototypes and 100 mg Demonstration batch tablets appear to overlap where sharp increase is observed from 150-200 MPa compression pressure. The 20 mg Compound 1 tablets do not show sharp increase over compression range tested and has a more robust operating window. Additional dissolution testing was performed on 100 mg Compound 1 tablets at 200 and 250 MPa (FIGS. 23-25) to determine whether the sharp increase in disintegration time would impact release.

The extent of release between the 200 and 250 MPa tablets was the same, however, the initial rate was slightly faster with the 200 MPa compression tablets. Release profiles are similar to that of bulk demonstration batch material

TABLE 27

Disintegration and appearance of prototype
Compound 1 tablets after 4 weeks accelerated stability.

| Sample | Lot No. | Storage Condition | Appearance | Disintegration time (mm:ss) |
|---|---|---|---|---|
| 50 mg Compound 1 Tablet/lactose/ Ac-Di-Sol, 400 mg | G8-854-16-1 | 4 weeks/25° C./60% RH/CLOSED | Off-White Tablets | 2:50-3:50 |
| | | 4 weeks/40° C./75% RH/CLOSED | Off-White Tablets | 1:30-2:29 |
| | | 4 weeks/25° C./60% RH/OPEN | Off-White Tablets | 0:45-0.52 |
| | | 4 weeks/40° C./75% RH/OPEN | Off-White Tablets | 12:50-13:38 |
| | | t = 0 | Off-White Tablets | 1:51 |
| 50 mg Compound 1 Tablet/mannitol/ Ac-Di-Sol, 400 mg | G8-854-17-1 | 4 weeks/25° C./60% RH/CLOSED | Off-White Tablets | 5:52-6:01 |
| | | 4 weeks/40° C./75% RH/CLOSED | Off-White Tablets | 2:17-2:40 |
| | | 4 weeks/25° C./60% RH/OPEN | Off-White Tablets | 1:13-1:27 |
| | | 4 weeks/40° C./75% RH/OPEN | Off-White Tablets | 14:50-16:00 |
| | | t = 0 | Off-White Tablets | 1:58 |

Both tablet formulations seem to be equivalent in terms of stability and in vitro performance. PK testing determined Mannitol/Ac-Di-Sol provided better exposure and was nominated for scale up. Lactose and mannitol tablet formulations were equivalent in exposure to the 25:75 SDD suspension. Stability studies indicate packaging will require desiccant to protect the tablets from moisture as demonstrated by the differences in chemical stability at 40C/75% RH in the open vs. closed with desiccant HDPE bottle configurations.

Figure 26:
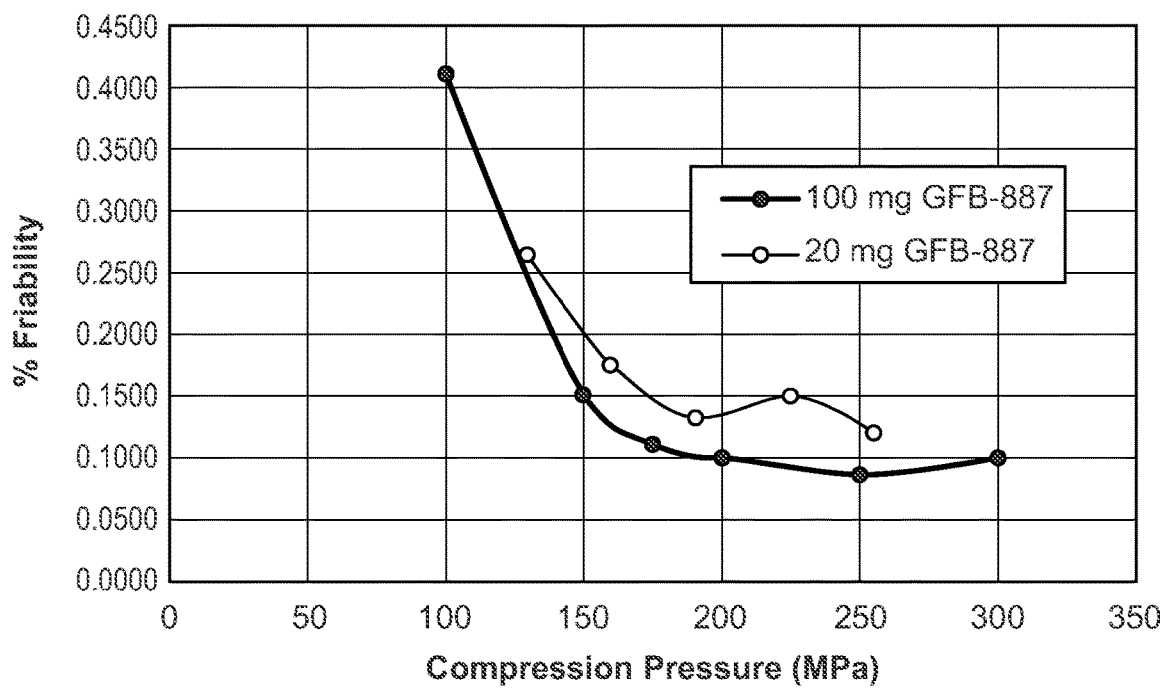
FIG. 26. Friability profiles 20- and 100-mg Compound 1 Demonstration Batch tablets.

Example 27. Compound 1 Tablet Demonstration Batch: Compound 1 Demonstration Batch Tablet Compression Demonstration batch Compound 1 tablets were manufactured on the Piccola 10 station rotary press at 20 rpm turret speed. Compression and disintegration profiles were generated and compared to feasibility Compound 1 tablets (FIG. 22).

on the CoT (Appendix E). Cyno PK was also performed where no difference in Cmax of AUC was observed when compared to the nominated 175 MPa compression pressure. Demonstration batch tablet friability profiles show low friability values above 100 MPa compression pressure (FIG. 26).

Figure 27:
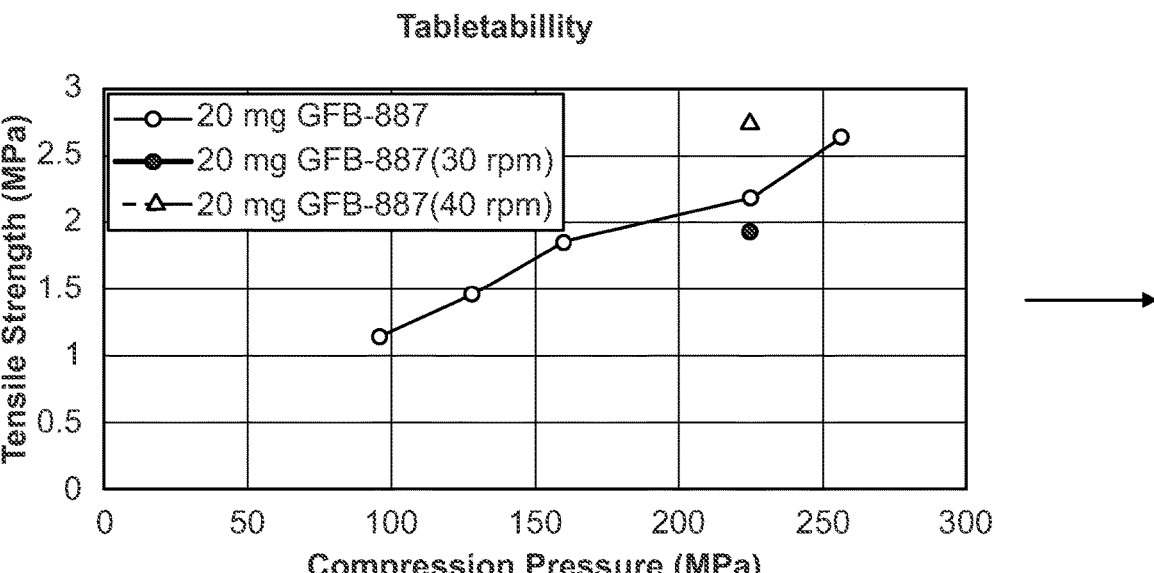
FIG. 27. Tabletability of 20-mg Compound 1 Demonstration Batch tablets.
Figure 28:
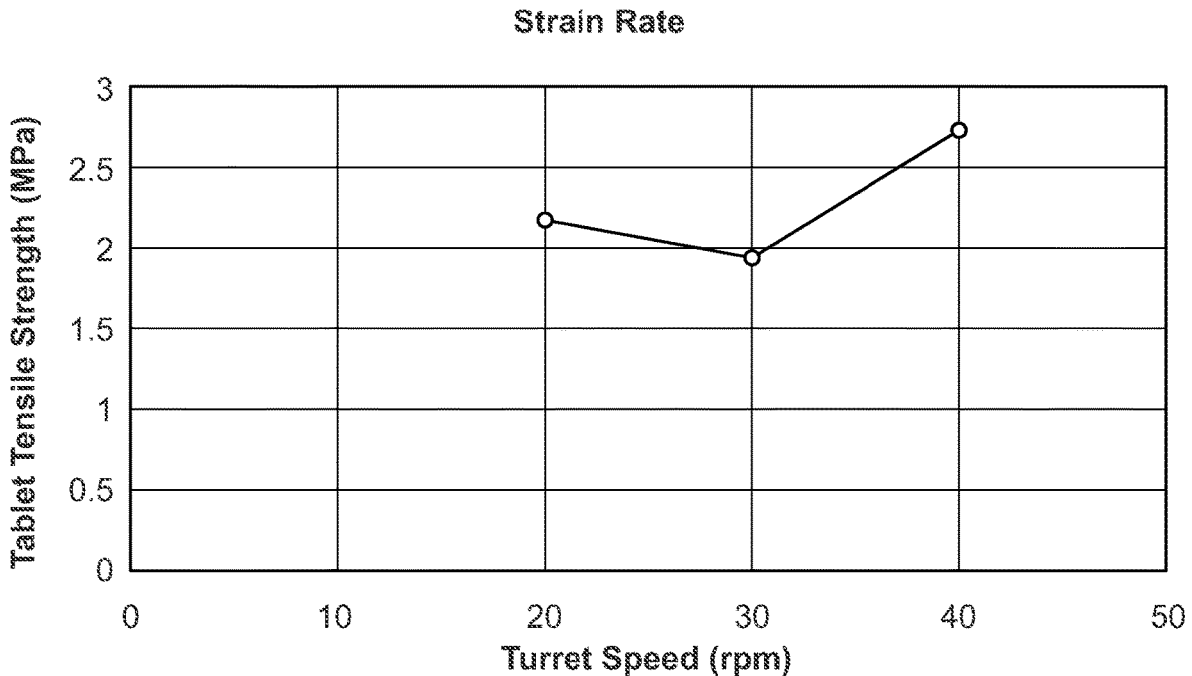
FIG. 28. Strain rate of 20-mg Compound 1 Demonstration Batch tablets. The formulation does not appear to be strain rate sensitive.

Strain rate was tested on the 20 mg Compound 1 tablets at speeds of 30 and 40 rpm table speed. Tablet tensile strength remained consistent at all speeds tested. Formulation does not appear to be strain rate sensitive on the 10 station Piccola rotary press at speeds of 20-40 rpm (FIGS. 27-28).

Target compression of 20 mg Compound 1 tablets was 225±25 MPa, and 175±25 MPa for 100 mg tablets. Beginning/Middle/End samples were gathered throughout compression and were tested for weight, thickness, breaking force, disintegration, and friability. Consistent values were observed over all samples. Friability and disintegration data can be seen in Tables 28 and 29.

TABLE 28

Disintegration times of
beginning, middle, and end samples for 20 and 100 mg
Compound 1 Demonstration Batch tablets

| Tablet Strength | Sample | Time First (m:s) | Time Last (m:s) |
|---|---|---|---|
| 20 mg Compound 1 | Beginning | 02:39.0 | 03:41.0 |
| | Middle | 01:26.0 | 03:17.0 |
| | End | 01:28.0 | 04:08.0 |
| 100 mg Compound 1 | Beginning | 02:23.0 | 02:50.0 |
| | Middle | 02:17.0 | 03:21.0 |
| | End | 02:21.0 | 02:43.0 |

TABLE 29

Friability of beginning, middle, and end samples
for 20 and 100 mg Compound 1 Demonstration Batch tablets.

| Tablet Strength | Sample | Initial Weight (g) | Final Weight (g) | % Loss |
|---|---|---|---|---|
| 20 mg Compound 1 | Beginning | 6.4790 | 6.473 | 0.0926 |
| | Middle | 6.5010 | 6.492 | 0.1384 |
| | End | 6.4850 | 6.478 | 0.1079 |
| 100 mg Compound 1 | Beginning | 8.0400 | 8.035 | 0.0622 |
| | Middle | 8.0090 | 8.005 | 0.0499 |
| | End | 7.7400 | 7.735 | 0.0646 |

Figure 29:
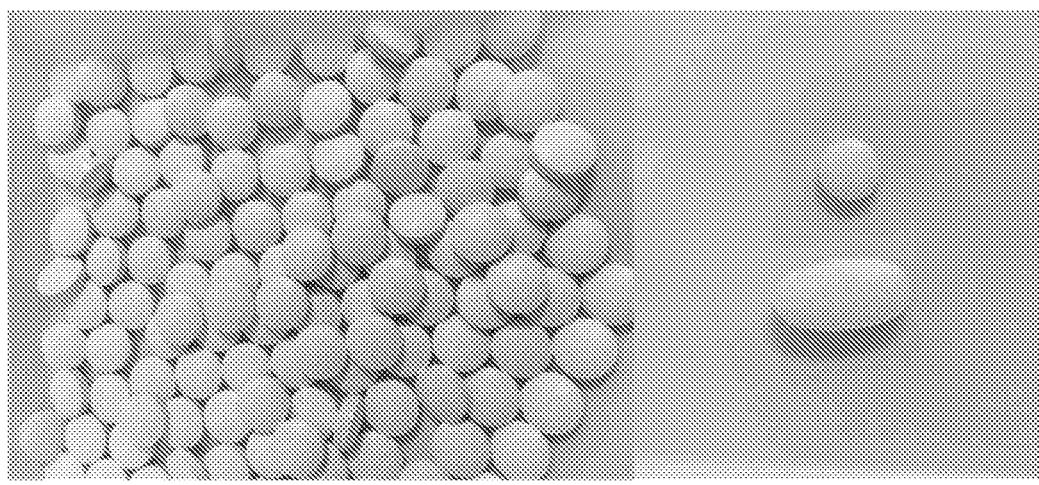
FIG. 29. Image of 20- and-100 mg Compound 1 Demonstration Batch tablets where mottling can be seen.

Tablets have a mottled appearance due to the off-white color of the SDI which has contrasts the white color of extra-granular components (FIG. 29). Mottling also may be mitigated by roller compacting ribbons to a lower solid fraction.

All tablet samples disintegrated within ~1-4 minutes and passed friability. Tablet weight remained consistent and no powder flow issues were observed during compression of both tablet strengths. A composite sample of each tablet batch (n=50) was analyzed for weight where tight distributions were found. Average tablet weight was on target and only two tablets were outside of 5% weight variation (both 20 mg Compound 1) (FIG. 30).

Summary of both batches can be seen in Table 30.

TABLE 30

20 and 100 mg Compound 1 Tablet Demonstration Batch Summary.

| Tablet Strength | 20 mg Compound 1 | 100 mg Compound 1 |
|---|---|---|
| Tablet Lot No. | G8-854-34 | G8-854-36 |
| # of Stations | 10 | 10 |
| Tooling Shape[4] | 0.3125" SRC | 0.3543" × 0.6980" Modified Oval |
| Target Tablet Weight (mg) | 160 ± 8 mg | 800 ± 40 mg |
| Fill Cam (mm) | 0-12 | 0-12 |
| Batch Size (g) | 1000.0 | 5078.2 |
| Batch Run Time (min) | 25 | 25 |
| Turret Speed (rpm) | 20 | 20 |
| Feed Frame (rpm) | 19 | 19 |
| Pre-Compression (N) | 150-250 | 500-600 |
| Compression Pressure (MPa) | 225 | 175 |
| Ejection Force (N) | 60 | 160 |
| Tablet Breaking Force (kP) | 8.0 | 24.0 |
| Tablet Thickness (mm) | 3.60 | 6.35 |
| Ave Tablet Weight (mg) | 158 | 801 |
| Standard Deviation (mg) | 3.4 | 11.1 |
| % RSD | 2.15 | 1.39 |
| Disintegration Time (min:sec) | 1:30-4:00 | 2:20-3:20 |

TABLE 30-continued 20 and 100 mg Compound 1 Tablet Demonstration Batch Summary.

| Tablet Strength | 20 mg Compound 1 | 100 mg Compound 1 |
|---|---|---|
| Friability (% Loss) | 0.113 | 0.0589 |
| % Yield[5] | 53.8 | 73.2 |
| % Accountability | 94.5 | 94.3 |

Figure 32:
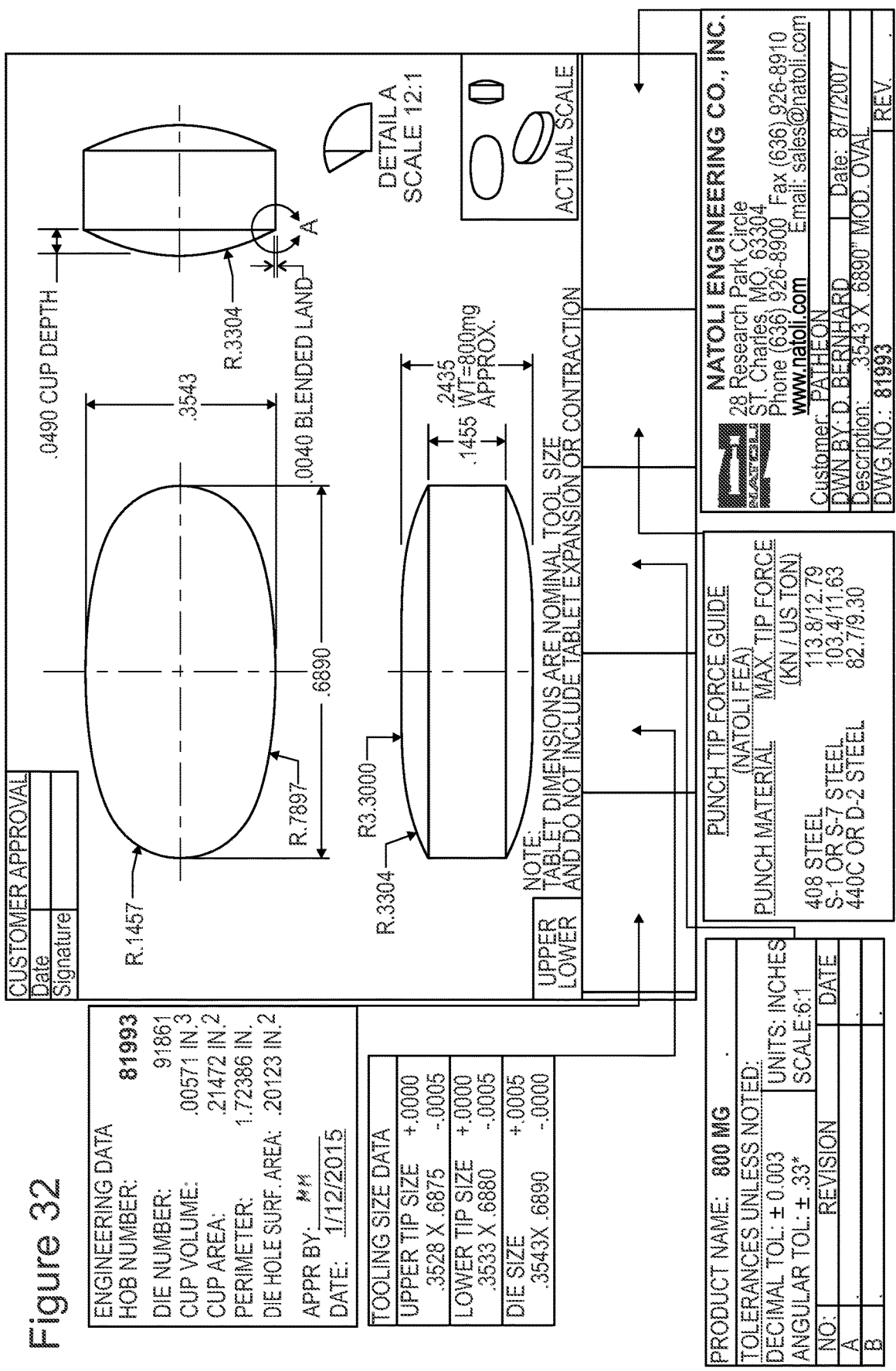
FIG. 32 shows a 0.3543"×0.6890" modified oval tablet tooling drawing according to some embodiments of the invention.

[4]See FIGS. 31-32 for tooling drawings.
[5]Low yield due to material consumption during range finding activities.

Example 28. Compound 1 Tablet Demonstration Batch: Compound 1 Demonstration Batch Tablet Analytical Testing 20 and 100 mg Compound 1 Demonstration batch tablets were tested for appearance, water content, assay/related substances, stratified content uniformity (Table 31), and dissolution. All analytical results have been compiled in Certificates of Testing which can be viewed in FIGS. 33-34.

TABLE 31

Stratified CU data for beginning, middle, and end samples
for 20 and 100 mg Compound 1 Demonstration Batch tablets

| Tablet Strength | Sample | Mean % LC | AV |
|---|---|---|---|
| 20 mg Compound 1 | Beginning | 98.0 | 5.7 |
| | Middle | 96.9 | 5.5 |
| | End | 93.3 | 14.5 |
| 100 mg Compound 1 | Beginning | 98.9 | 2.0 |
| | Middle | 98.8 | 3.7 |
| | End | 95.4 | 7.1 |

Example 29. Conclusions

SDI feasibility found that amorphous dispersions could be manufactured at 25% Compound 1, while 50 and 66% Compound 1 remained partially crystalline after the spray drying process. SDI formulations that showed best in vitro improvement over crystalline Compound 1 were 25% Compound 1 in HPMCAS-M and HPMCAS-L. Accelerated stability testing of amorphous dispersions reviled that crystalline growth was found in 40° C./75% RH and 50° C./75% RH open conditions, where closed conditions with desiccant remained fully amorphous, indicating moisture exposure has a significant impact on physical stability of the dispersions. Based on PK testing performed by Goldfinch, 25:75 Compound 1:HPMCAS-M was the nominated SDI and was successfully manufactured on the pilot scale MS-150 and residual solvent was removed using an Ekato vacuum dryer. The nominated prototype tablet formulation was successfully scaled up to the Vector TFC-220 roller compactor and Piccola 10 station rotary press. Due to high level of fines and flow issues observed during discharge of Final Blend, it is recommended to do further development on the granulation process. Improving flow will be critical for higher throughput manufacturing. Milling ribbons with a lower energy mill may remedy this issue. GMP manufacturing will use identical equipment for spray drying and tableting, and is expected to have a high likelihood of success.

Example 30. Sample Formulations

1-mg tablet

| Component; Quality Standard | Function | Weight Percent per Unit | Amount per Unit (1 mg strength) |
|---|---|---|---|
| Intragranular Excipients | | | |
| 25% Active, drug product intermediate (Compound 1:75% HPMCAS-M (% w/w)[a], in-house | Active Ingredient | 3.33 | 4.0 mg |
| Mannitol[b] USP, EP | Filler | 39.33 | 47.2 mg |
| Microcrystalline cellulose; NF, EP | Filler | 39.33 | 47.2 mg |
| Croscarmellose sodium; NF, EP | Disintegrant | 3 | 3.6 mg |
| Stearyl fumarate sodium; NF, EP | Lubricant | 0.7 | 0.8 mg |
| Colloidal silicon dioxide; NF, EP | Glidant | 1 | 1.2 mg |
| Extragranular Excipients | | | |
| Microcrystalline cellulose; NF, EP | Filler | 10 | 12.0 mg |
| Croscarmellose sodium; NF, EP | Disintegrant | 3 | 3.6 mg |
| Stearyl fumarate sodium; NF, EP | Lubricant | 0.25 | 0.3 mg |
| Total | | 100 | 120.0 mg |

[a]The Compound 1 Active for the tablets is supplied as a Compound 1 SDD.
[b]The amount of mannitol used is adjusted to compensate for the measured potency of the SDD.

5-mg tablet

| Component; Quality Standard | Function | Weight Percent per Unit | Amount per Unit (5 mg Strength) |
|---|---|---|---|
| Intragranular Excipients | | | |
| 25% Active, drug product intermediate (Compound 1:75% HPMCAS-M (% w/w)[a], in-house | Active Ingredient | 16.67 | 20.0 mg |
| Mannitol[b] USP, EP | Filler | 32.69 | 39.2 mg |
| Microcrystalline cellulose; NF, EP | Filler | 32.69 | 39.2 mg |
| Croscarmellose sodium; NF, EP | Disintegrant | 3 | 3.6 mg |
| Stearyl fumarate sodium; NF/EP | Lubricant | 0.7 | 0.8 mg |
| Colloidal silicon dioxide; NF, EP | Glidant | 1 | 1.2 mg |
| Extragranular Excipients | | | |
| Microcrystalline cellulose; NF, EP | Filler | 10 | 12.0 mg |
| Croscarmellose sodium; NF, EP | Disintegrant | 3 | 3.6 mg |
| Stearyl fumarate sodium; NF, EP | Lubricant | 0.25 | 0.3 mg |
| Total | | 100 | 120.0 mg |

[a]The Compound 1 Active for the tablets is supplied as a Compound 1 SDD.
[b]The amount of mannitol used is adjusted to compensate for the measured potency of the SDD.

20- and 100-mg tablets

| Component | wt. % | Compound 1 Tablets, 20 mg (mg/tablet) | Compound 1 Tablets, 100 mg (mg/tablet) |
|---|---|---|---|
| 25:75 Compound 1:HPMCAS-M (SDI) | 50 | 80 | 400 |
| Avicel PH-105 (Microcrystalline cellulose) | 16 | 25.6 | 128 |
| Pearlitol 100SD (mannitol) | 21 | 33.6 | 168 |
| Ac-Di-Sol (Croscarmellose Sodium) | 3 | 4.8 | 24 |

-continued

20- and 100-mg tablets

| Component | wt. % | Compound 1 Tablets, 20 mg (mg/tablet) | Compound 1 Tablets, 100 mg (mg/tablet) |
|---|---|---|---|
| Cab-O-Sil (Silicon Dioxide) | 1 | 1.6 | 8 |
| Sodium Stearyl Fumarate | 0.75 | 1.2 | 6 |
| Intra-Granular Total: | 91.75 | 146.8 | 734 |
| Avicel PH-200 (microcrystalline cellulose) | 5 | 8 | 40 |
| Ac-Di-Sol (Croscarmellose Sodium) | 3 | 4.8 | 24 |
| Sodium Stearyl Fumarate | 0.25 | 0.4 | 2 |
| Total: | 100 | 160 | 800 |

INCORPORATION BY REFERENCE

All of the U.S. patents and U.S. and PCT published patent applications cited herein are hereby incorporated by reference.

EQUIVALENTS

The foregoing written specification is sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A composition for manufacturing a spray-dried dispersion, the composition comprising 4-chloro-5-(4-(4-fluoro-2-(trifluoromethyl)phenoxy)-5,8-dihydropyrido[3,4-d]pyrimidin-7(6H)-yl)pyridazin-3(2H)-one; a solvent; and a polymer; wherein the polymer is dissolved in the solvent; and wherein the polymer is selected from the group consisting of hypromellose acetate succinate, a polymethacrylate copolymer Eudragit, and a combination thereof.

2. The composition of claim 1, wherein the 4-chloro-5-(4-(4-fluoro-2-(trifluoromethyl)phenoxy)-5,8-dihydropyrido[3,4-d]pyrimidin-7(6H)-yl)pyridazin-3(2H)-one is in an amorphous form.

3. The composition of claim 1, wherein the polymer is hypromellose acetate succinate.

4. The composition of claims 1, wherein the solvent is acetone, methyl ethlyketone, ethyl acetate, isopropyl alcohol, dioxane, acetonitrile, ethanol, water, methanol, dichloromethane, tetrahydrofuran, or a combination of any of them.

5. A method of manufacturing a spray-dried dispersion, comprising the step of spray-drying the composition of claim 1.

6. A spray-dried dispersion comprising 4-chloro-5-(4-(4-fluoro-2-(trifluoromethyl)phenoxy)-5,8-dihydropyrido[3,4-d]pyrimidin-7(6H)-yl)pyridazin-3(2H)-one; and a polymer; wherein the polymer is selected from the group consisting of hypromellose acetate succinate, a polymethacrylate copolymer, and a combination thereof.

7. The spray-dried dispersion of claim 6, wherein the 4-chloro-5-(4-(4-fluoro-2-(trifluoromethyl)phenoxy)-5,8-dihydropyrido[3,4-d]pyrimidin-7(6H)-yl)pyridazin-3(2H)-one is in an amorphous form.

8. The spray-dried dispersion of claim 6, wherein the polymer is hypromellose acetate succinate.

9. A solid dosage form comprising the spray-dried dispersion of claim 6, and one or more of a filler, a disintegrant, a lubricant, a glidant, and a stabilizer.

10. The solid dosage form of claim 9, wherein the spray-dried dispersion is present at between about 3% to about 60% w/w.

11. The solid dosage form of claim 10, wherein the spray-dried dispersion is present at about 50% w/w, about 16.7% w/w, or about 3.33% w/w.

12. The solid dosage form of claim 9, wherein the 4-chloro-5-(4-(4-fluoro-2-(trifluoromethyl)phenoxy)-5,8-dihydropyrido[3,4-d]pyrimidin-7(6H)-yl)pyridazin-3(2H)-one is present at about 0.75%-15% w/w.

13. The solid dosage form of claim 9, consisting essentially of:
 a. 4-chloro-5-(4-(4-fluoro-2-(trifluoromethyl)phenoxy)-5,8-dihydropyrido[3,4-d]pyrimidin-7(6H)-yl)pyridazin-3(2H)-one;
 b. hypromellose acetate succinate;
 c. mannitol;
 d. microcrystalline cellulose;
 e. croscarmellose sodium;
 f. stearyl fumarate sodium; and
 g. colloidal silicon dioxide.

14. The solid dosage form of claim 9, consisting essentially of:
 a. 20 mg of 4-chloro-5-(4-(4-fluoro-2-(trifluoromethyl)phenoxy)-5,8-dihydropyrido[3,4-d]pyrimidin-7(6H)-yl)pyridazin-3(2H)-one;
 b. 60 mg of hypromellose acetate succinate;
 c. 33.6 mg of mannitol;
 d. 33.6 mg of microcrystalline cellulose;
 e. 9.6 mg of croscarmellose sodium;
 f. 1.6 mg stearyl fumarate sodium; and
 g. 1.6 mg colloidal silicon dioxide;
 or consisting essentially of:
 h. 100 mg of 4-chloro-5-(4-(4-fluoro-2-(trifluoromethyl)phenoxy)-5,8-dihydropyrido[3,4-d]pyrimidin-7(6H)-yl)pyridazin-3(2H)-one;
 i. 300 mg of hypromellose acetate succinate;
 j. 168 mg of mannitol;
 k. 168 mg of microcrystalline cellulose;
 l. 48 mg of croscarmellose sodium;
 m. 8 mg stearyl fumarate sodium; and
 n. 8 mg colloidal silicon dioxide;
 or consisting essentially of:
 o. 0.5 mg of 4-chloro-5-(4-(4-fluoro-2-(trifluoromethyl)phenoxy)-5,8-dihydropyrido[3,4-d]pyrimidin-7(6H)-yl)pyridazin-3(2H)-one;
 p. 15 mg of hypromellose acetate succinate;
 q. 39.2 mg of mannitol;
 r. 51.2 mg of microcrystalline cellulose;
 s. 7.2 mg of croscarmellose sodium;
 t. 1.1 mg of stearyl fumarate sodium; and
 u. 1.2 mg of colloidal silicon dioxide;
 or consisting essentially of:
 v. 1 mg of 4-chloro-5-(4-(4-fluoro-2-(trifluoromethyl)phenoxy)-5,8-dihydropyrido[3,4-d]pyrimidin-7(6H)-yl)pyridazin-3(2H)-one;

w. 3 mg of hypromellose acetate succinate;
 x. 47.2 mg of mannitol;
 y. 59.2 mg of microcrystalline cellulose;
 z. 7.2 mg of croscarmellose sodium;
 aa. 1.1 mg of stearyl fumarate sodium; and
 ab. 1.2 mg of colloidal silicon dioxide.

15. The solid dosage form of claim 9, wherein the solid dosage form is a tablet.

16. The solid dosage form of claim 15, wherein the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 1-200 mg.

17. The solid dosage form of claim 16, wherein the amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in the tablet or capsule is about 1 mg, about 5 mg, about 20 mg, or about 100 mg.

18. A method of manufacturing a solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of:
 a. blending a spray-dried dispersion of claim 6 with one or more of: a first filler, a first disintegrant, a first lubricant, a first glidant, and a first stabilizer to form a first solid mixture;
 b. roller compacting and milling the first solid mixture; and
 c. optionally blending the roller compacted and milled first solid mixture with one or more of a second filler, a second disintegrant, a second lubricant, a second glidant, and a second stabilizer to form a second solid mixture; and
 d. converting the first or the second solid mixture into the solid dosage form of 4-chloro-5-(4-(4-fluoro-2-(trifluoromethyl)phenoxy)-5,8-dihydropyrido[3,4-d]pyrimidin-7(6H)-yl)pyridazin-3(2H)-one.

19. The method of claim 18, wherein the solid dosage form is (a) a tablet formed by compressing the first solid mixture or the second solid mixture, or (b) a filled capsule formed by filling a capsule with the first solid mixture or the second solid mixture.

20. A method of treating a kidney disease or a nephropathy associated with a disease or condition, comprising administering to a subject in need thereof a solid dosage form of claim 9.

21. The method of claim 20, wherein the kidney disease or the nephropathy associated with a disease or condition is Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), clq nephropathy, rapidly progressive GN, anti-GBM disease, C3 glomerulonephritis, hypertensive nephrosclerosis, IgA nephropathy, IgG4 nephropathy, proteinuric kidney disease, microalbuminuria, macroalbuminuria kidney disease, transplant-related FSGS, transplant-related nephrotic syndrome, transplant-related proteinuria, nodular glomerulonephritis, NASR disease (proliferative glomerulonephritis with monoclonal IgG deposits), polycystic kidney disease, autosomal dominant polycystic kidney disease (ADPKD), or an nephropathy associated with any one of obesity, insulin resistance, Type II diabetes, prediabetes, metabolic syndrome, dyslipidemia, pulmonary arterial hypertension, cancer, cholestatic liver disease, non-alcoholic fatty liver disease (NAFLD), non-alcoholic steatohepatitis (NASH) or Fabry's disease).

22. The method of claim 21, wherein the kidney disease is diabetic nephropathy, FSGS, or minimal change disease.

23. A method of treating pain, anxiety, or depression, comprising administering to a subject in need thereof a solid dosage form of claim 9.

24. The composition of claim 1, wherein the polymer is an anionic copolymer comprising methacrylic acid and methyl methacrylic acid that dissolves at pH above 6.

25. The composition of claim 1, wherein the polymer comprises hypromellose acetate succinate and an anionic copolymer comprising methacrylic acid and methyl methacrylic acid that dissolves at pH above 6.

26. The spray-dried dispersion of claim 6, wherein the polymer is an anionic copolymer comprising methacrylic acid and methyl methacrylic acid that dissolves at pH above 6.

27. The spray-dried dispersion of claim 6, wherein the polymer comprises hypromellose acetate succinate and an anionic copolymer comprising methacrylic acid and methyl methacrylic acid that dissolves at pH above 6.

28. The solid dosage form of claim 9, comprising:
a. 4-chloro-5-(4-(4-fluoro-2-(trifluoromethyl)phenoxy)-5,8-dihydropyrido[3,4-d]pyrimidin-7(6H)-yl) pyridazin-3(2H)-one;
b. hypromellose acetate succinate;
c. an anionic copolymer comprising methacrylic acid and methyl methacrylic acid that dissolves at pH above 6;
d. lactose;

58 e. microcrystalline cellulose;
f. croscarmellose sodium;
g magnesium stearate; and
h. colloidal silicon dioxide.

29. The solid dosage form of claim 28, comprising:
a. 0.75%-40.0% (w/w) 4-chloro-5-(4-(4-fluoro-2-(trifluoromethyl) phenoxy)-5,8-dihydropyrido[3,4-d]pyrimidin-7(6H)-yl) ypromello-3(2H)-one;
b. 2.0%-54.0% (w/w) hypromellose acetate succinate;
c. 3.75%-42.3% (w/w) lactose;
d. 3.75%-50.0% (w/w) microcrystalline cellulose;
e. 3.0%-15% (w/w) croscarmellose sodium;
f. 0.5%-5.0% (w/w) magnesium stearate;
g. 0.1%-5.0% (w/w) colloidal silicon dioxide; and
h. an anionic copolymer comprising methacrylic acid and methyl methacrylic acid that dissolves at pH above 6,
wherein:
the ratio of 4-chloro-5-(4-(4-fluoro-2-(trifluoromethyl) phenoxy)-5,8-dihydropyrido[3,4-d]pyrimidin-7(6H)-yl)hypromello-3(2H)-one to hypromellose acetate succinate is between 1:9 and 2:1;
the sum of the amounts of 4-chloro-5-(4-(4-fluoro-2-(trifluoromethyl) phenoxy)-5,8-dihydropyrido[3,4-d]pyrimidin-7(6H)-yl)pyridazin-3(2H)-one and hypromellose acetate succinate is between 3% and 60% w/w of the solid dosage form;
the ratio of lactose to microcrystalline cellulose is between 1:3 and 3:1; and
the sum of the amounts of lactose and microcrystalline cellulose is between 15.0 and 90% w/w of the solid dosage form.

* * * * *